United States Patent
Zhang et al.

(10) Patent No.: US 11,939,387 B2
(45) Date of Patent: Mar. 26, 2024

(54) ANTI-HUMAN INTERLEUKIN-4 RECEPTOR ALPHA ANTIBODY AND PREPARATION METHOD AND APPLICATION THEREOF

(71) Applicant: SHANGHAI MABGEEK BIOTECH. CO., LTD., Shanghai (CN)

(72) Inventors: Chenghai Zhang, Shanghai (CN); Jinlin Guo, Shanghai (CN); Yujing Yuan, Shanghai (CN)

(73) Assignee: SHANGHAI MABGEEK BIOTECH. CO., LTD, Shanghai (CN)

( * ) Notice: Subject to any disclaimer, the term of this patent is extended or adjusted under 35 U.S.C. 154(b) by 0 days.

(21) Appl. No.: 18/047,039

(22) Filed: Oct. 17, 2022

(65) Prior Publication Data

US 2023/0203172 A1 Jun. 29, 2023

Related U.S. Application Data

(63) Continuation of application No. PCT/CN2021/086806, filed on Apr. 13, 2021.

(30) Foreign Application Priority Data

Apr. 17, 2020 (CN) .......................... 202010309238.8

(51) Int. Cl.
| | | |
|---|---|---|
| C07K 16/28 | (2006.01) | |
| A61K 39/395 | (2006.01) | |
| A61P 11/06 | (2006.01) | |
| C12N 5/16 | (2006.01) | |
| A61K 39/00 | (2006.01) | |
| C07K 14/705 | (2006.01) | |

(52) U.S. Cl.
CPC ...... C07K 16/2866 (2013.01); A61K 39/3955 (2013.01); A61P 11/06 (2018.01); C07K 16/2896 (2013.01); C12N 5/16 (2013.01); *A61K 39/00* (2013.01); *A61K 2039/505* (2013.01); *C07K 2317/24* (2013.01); *C07K 2317/565* (2013.01); *C07K 2317/76* (2013.01); *C07K 2317/92* (2013.01); *C12N 2510/02* (2013.01)

(58) Field of Classification Search
CPC ............ C07K 2317/76; C07K 16/2866; C07K 2317/565; C07K 2317/56; C07K 2317/92; C07K 16/2896; A61K 39/3955; A61K 2039/505
See application file for complete search history.

(56) References Cited

U.S. PATENT DOCUMENTS

| | | | |
|---|---|---|---|
| 4,816,567 | A | 3/1989 | Cabilly et al. |
| 7,186,809 | B2 | 3/2007 | Pluenneke |
| 7,605,237 | B2 | 10/2009 | Stevens et al. |
| 7,638,606 | B2 | 12/2009 | Carter et al. |
| 8,092,804 | B2* | 1/2012 | Eriksson .................. A61P 29/00 424/139.1 |
| 8,980,273 | B1* | 3/2015 | Clube ................. C07K 16/2866 424/143.1 |
| 2014/0056920 | A1* | 2/2014 | Ardeleanu ......... G01N 33/6893 424/173.1 |
| 2014/0356372 | A1 | 12/2014 | Stahl et al. |
| 2015/0150963 | A1 | 6/2015 | Jackson et al. |
| 2015/0320022 | A1 | 11/2015 | Wang et al. |
| 2017/0281769 | A1 | 10/2017 | Eriksson et al. |
| 2021/0087284 | A1 | 3/2021 | Xu et al. |
| 2021/0206861 | A1 | 7/2021 | Zhao et al. |
| 2022/0056143 | A1 | 2/2022 | Morsey et al. |
| 2022/0073631 | A1 | 3/2022 | Qiu et al. |
| 2022/0081485 | A1 | 3/2022 | Liu et al. |

FOREIGN PATENT DOCUMENTS

| | | |
|---|---|---|
| CN | 1886426 A | 12/2006 |
| CN | 102046658 A | 5/2011 |
| CN | 105377894 A | 3/2016 |
| CN | 107474134 A | 12/2017 |
| CN | 108373505 A | 8/2018 |
| CN | 108409860 A | 8/2018 |
| CN | 110105451 A | 8/2019 |
| CN | 110746507 A | 2/2020 |
| CN | 110872349 A | 3/2020 |
| CN | 111647082 A | 9/2020 |
| JP | 2000515016 A | 11/2000 |
| JP | 2015520175 A | 7/2015 |
| JP | 2017514501 A | 6/2017 |
| JP | 2017527560 A | 9/2017 |
| JP | 2019506146 A | 3/2019 |
| RU | 2490278 C2 | 8/2013 |
| WO | 9803654 A2 | 1/1998 |
| WO | 2009081201 A2 | 7/2009 |
| WO | 2019200787 A1 | 10/2019 |
| WO | 2019228405 A1 | 12/2019 |
| WO | 2022135441 A1 | 6/2022 |

OTHER PUBLICATIONS

Brorson et al. Mutational analysis of avidity and fine specificity of anti-levan antibodies. J Immunol 163: 6694-6701, 1999.*
Brummell et al. Probing the combining site of an anti-carbohydrate antibody by saturation-mutagenesis: role of the heavy-chain CDR3 residues. Biochem 32(4): 1180-1187, 1993 (abstract).*
Burks et al. In vitro scanning saturation mutagenesis of an antibody binding pocket. Proc Natl Acad Sci USA 94: 412-417, 1997.*
Cassett et al. A peptide mimetic of an anti-CD4 monoclonal antibody by rationale design. Biochem Biophys Res Comm 307: 198-205, 2003.*

(Continued)

*Primary Examiner* — Bridget E Bunner
(74) *Attorney, Agent, or Firm* — Sheppard Mullin Richter & Hampton LLP

(57) ABSTRACT

The present invention discloses an antibody capable of binding to human interleukin 4 receptor alpha (hIL-4R alpha) and a preparation method and application thereof. The anti-hIL-4R alpha antibody can specifically bind to hIL-4R alpha, has good effects for inhibiting IL-4 and IL-13-induced cell line proliferation and the like, and can be applied to treatment of IL-4R alpha related diseases, such as immune-mediated inflammatory diseases.

10 Claims, 5 Drawing Sheets

Specification includes a Sequence Listing.

(56) References Cited

OTHER PUBLICATIONS

Chen et al. J Mol Biol 293: 865-881, 1999.*
Colman Research in Immunol. 145:33-36, 1994.*
De Pascalis et al. Grafting and "abbreviated" complementarity-determining regions containing specificity-determining residues essential for ligand contact to engineer a less immunogenic humanized monoclonal antibody. J Immunol 169: 3076-3084, 2002.*
Edwards et al. The remarkable flexibility of the human antibody repertoire; isolation of over one thousand different antibodies to a single protein, Blys. J Mol Biol 334: 103-118, 2003.*
Holm et al. Functional mapping and single chain construction of the anti-cytokeratin 8 monoclonal antibody TS1. Mol Immunol 44: 1075-1084, 2007.*
Jang et al. The structural basis for DNA binding by an anti-DNA autobody. Mol Immunol 35: 1207-1217, 1998.*
Kobayashi et al. Tryptophan H33 plays an important role in pyrimidine (6-4) pyrimidone photoproduct binding by a high-affinity antibody. Protein Engineering 12(10): 879-884, 1999.*
Le Floc'h et al. Dual blockade of IL-4 and IL-13 with dupilumab, an IL-4Ralpha antibody, is required to broadly inhibt type 2 inflammation. Allergy 75: 1188-1204, 2020.*
Lloyd et al. Modelling the human immune response: performance of a 10×11 human antibody repertoire against a broad panel of therapeutically relevant antigens. Protein Eng Design Selection 22(3): 159-168, 2009.*
MacCallum et al. Antibody-antigen interactions: contact analysis and binding site topography. J Mol Biol 262: 732-745, 1996.*
Massey et al. Recent advances in the inhibition of the IL-4 cytokine pathway for the treatment of allergen-induced asthma. Int J Mol Sci 22: 13655, 2021 (11 total pages).*
Paul, William E., Fundamental Immunology, 3rd Edition, Raven Press, New York, Chapt. 8, pp. 292-295 (1993).*
Rudikoff et al. Single amino acid substitution altering antigen-binding specificity. Proc Natl Acad Sci USA 79: 1979-1983, 1982.*
Sela-Culang et al. The structural basis of antibody-antigen recognition. Front Immunol 4: 302, 2013 (13 total pages).*
Vajdos et al. Comprehensive functional maps of the antigen-binding site of an anti-ErbB2 antibody obtained with shotgun scanning mutagenesis. J Mol Biol 320: 415-428, 2002.*
Vasudevan et al. A single amino acid change in the binding pocket alters specificity of an anti-integrin antibody AP7.4 as revealed by its crystal structure. Blood Cell Mol Dis 32: 176-181, 2004.*
Wu et al. Humanization of a murine monoclonal antibody by simultaneous optimization of framework and CDR residues. J Mol Biol 294: 151-162, 1999.*
Zhang et al. Comprehensive optimization of a single-chain variable domain antibody fragment as a targeting ligand for a cytotoxic nanoparticle. mAbs 7(1): 42-52, 2015.*

Al-Lazikani et al., "Standard Conformations for the Canonical Structures of Immunoglobulins," J.Mol.Biol, vol. 273, pp. 927-948, Nov. 7, 1997.
Kabat et al., "Sequences of Proteins of Immunological Interest," National Institutes of Health, 1983, p. 323.
Martin et al., "Modeling antibody hypervariable loops: A combined algorithm," Proceedings of the National Academy of Sciences, vol. 86, pp. 9268-9272, Dec. 1989.
Morrison et al., "Chimeric human antibody molecules: Mouse antigen-binding domains with human constant region domains," Proceedings of the National Academy of Sciences, vol. 81, pp. 6851-6855, Nov. 1984.
International Search Report issued in International Patent Application No. PCT/CN2021/086806, dated Jul. 9, 2021, 14 pages.
Written Opinion of the International Search Authority issued in International Patent Application No. PCT/CN2021/086806, dated Jul. 9, 2021, 9 pages.
Kim, J.E. et al., "Engineering of anti-human interleukin-4 receptor alpha antibo-dies with potent antagonistic activity" Scientific Reports, vol. 9, May 23, 2019, Document No. 7772.
First Office Action issued in Japanese Patent Application No. 2022-563020, dated Feb. 21, 2023, 9 pages.
First Office Action issued in Russian Patent Application No. 2022129484, dated Apr. 26, 2023, 20 pages.
Second Office Action issued in Japanese Patent Application No. 2022-563020, dated Jun. 27, 2023, 4 pages.
Pakula et al., "Genetic analysis of protein stability and function," Annu. Rev. Genet. 1989, v. 23, pp. 289-310, see pp. 305-306.
Dirks, "Brain Tumor Stem Cells: Bringing Order to the Chaos of Brain Cancer," Journal of Clinical Oncology, vol. 26, No. 17, Jun. 10, 2008, pp. 2916-2924.
Tran et al., "Survival comparison between glioblastoma multiforme and other incurable cancers," Journal of Clinical Neuroscience, vol. 17, Is. 4, 2010, pp. 417-421.
Mabey, "Epidemiology of sexually transmitted infections: worldwide," Medicine, vol. 42, No. 6, 2014, pp. 287-290.
Wang et al., "Silence of MCL-1 upstream signaling by shRNA abrogates multiple myeloma growth," Experimental Hematology & Oncology., vol. 3, No. 1,2014, pp. 1-7.
López-Lázaro, "The migration ability of stem cells can explain the existence of cancer of unknown primary site. Rethinking metastasis," Oncoscience, vol. 2, No. 5, 2015, pp. 467-475.
Oct. 3, 2023 Third Office Action issued in Japanese Patent Application No. 2022-563020.
Nov. 20, 2023 1st Examination Report issued in Saudi Patent Application No. 522440925.
Jan. 2, 2024 First Office Action issued in Chilean Patent Application No. 202202863.

* cited by examiner

Note: **$P<0.01$, vs PBS

Note: *$P<0.001$, **$P<0.0001$, vs PBS

Note: *$P<0.05$, *$P<0.001$, **$P<0.0001$, vs PBS

ANTI-HUMAN INTERLEUKIN-4 RECEPTOR ALPHA ANTIBODY AND PREPARATION METHOD AND APPLICATION THEREOF

CROSS-REFERENCE TO RELATED APPLICATIONS

This application is continuation application of PCT/CN2021/086806, filed Apr. 13, 2021, which claims priority from Chinese patent application 202010309238.8 filed on Apr. 17, 2020, the entire contents of which are hereby incorporated by reference.

REFERENCE TO AN ELECTRONIC SEQUENCE LISTING

The contents of the electronic sequence listing (364718.xml; Size: 203,451 bytes; and Date of Creation: Oct. 13, 2023) is herein incorporated by reference in its entirety.

TECHNICAL FIELD

The present invention relates to the field of antibodies, in particular to an anti-interleukin receptor antibody and a preparation method and application thereof.

BACKGROUND

Under the stimulation of an antigen, antigen-specific lymphocytes in human bodies will identify the antigen, respond with activation, proliferation, differentiation and the like, and finally clear the invaded antigen. T cells and B cells are primary effector cells. In terms of different types of antigens, T cells can expand and strengthen immune responses by killing target cells directly and secreting different types of cytokines, thereby achieving an immunological effect. Studies have shown that Th2 cytokines such as interleukin (IL)-4, IL-5, IL-9 and IL-13 mediate major pathological development in allergic diseases such as allergic asthma.

Asthma is a common respiratory disease, which is usually characterized by airway inflammation, bronchial hyperreactivity, and structural changes in bronchial walls (airway remodeling). Genetic backgrounds and stimulation of environmental factors including allergens and respiratory viruses induce the occurrence of asthma, with major pathological manifestations of recurrent wheezing, shortness of breath, chest tightness and coughs. There are 2.3 million patients with asthma worldwide, and the prevalence is expected to continue to rise in the coming decades. Currently, asthma is treated progressively to alleviate symptoms and control risks. Inhaled corticosteroids are a standard therapy for moderate asthma; patients suffering from severe asthma are treated in combination of a long-acting beta antagonist; and for patients suffering from the most severe asthma, an additional drug may be required. These treatments can cause immune system disorders and other serious side effects. Nevertheless, there is still no drug available for 5-10% of patients.

In allergic asthma, an abnormally high expression of Th2 cytokines in bronchi has been found, and meanwhile, it has been confirmed that the Th2 cytokines mediate the occurrence and development of inflammatory responses, and promote pathological changes and the like in a respiratory tract. These cytokines promote the activation of eosinophils, mast cells and other inflammatory cells, and the chemotaxis to inflammatory sites. IL-4 and IL-13 target B cells, transforming an antibody secreted thereby from IgM to IgE, and meanwhile, induce bronchial remodeling by induction of goblet cell hyperplasia, transformation of bronchial fibroblasts into myofibroblasts, collagen deposition, and proliferation of smooth muscle cells of the respiratory tract.

Both IL-4 and IL-13 can activate a corresponding signaling pathway by binding to interleukin-4 receptor alpha (IL-4R-alpha), therefore, an antagonist to IL-4R alpha can block pathological reactions of the IL-4 and the IL-13, and is expected to be used for the treatment of IL-4R alpha related diseases, including asthma.

SUMMARY

The inventors of the present invention, after having conducted a large number of experiments, obtained a group of monoclonal antibodies that can block the signal transduction of IL-4 and IL-13 by specifically blocking the binding of IL-4 and IL-13 to IL-4 receptor alpha (IL-4R alpha) on cell surfaces. The monoclonal antibodies can block IL-4/IL-13 mediated bioactivities.

According to a first aspect, this application provides an antibody specifically binding to IL-4 receptor alpha or an antigen-binding fragment thereof, including a heavy chain variable region, where the heavy chain variable region includes an HCDR3 sequence, and optionally further includes an HCDR1 and/or an HCDR2 sequence. In some embodiments, the HCDR3 sequence includes an amino acid sequence selected from the group consisting of SEQ ID NO: 107, 113, 119, 125, 131, 137, 143, 149, 155, 161, 167, 173, 179, 185, 191, 197 and 203. In some embodiments, the HCDR1 sequence includes an amino acid sequence selected from the group consisting of SEQ ID NO: 105, 111, 117, 123, 129, 135, 141, 147, 153, 159, 165, 171, 177, 183, 189, 195 and 201. In some embodiments, the HCDR2 sequence includes an amino acid sequence selected from the group consisting of SEQ ID NO: 106, 112, 118, 124, 130, 136, 142, 148, 154, 160, 166, 172, 178, 184, 190, 196 and 202. In an optional embodiment, the antigen-binding fragment is selected from the group consisting of an Fab fragment, an Fab' fragment, an F(ab')2 fragment, an Fv fragment, an scFv fragment, an Fd fragment and a single domain antibody.

In some embodiments, the heavy chain variable region includes an amino acid sequence having at least 80% homology with an amino acid sequence selected from the group consisting of SEQ ID NO: 2, 6, 10, 14, 18, 22, 26, 30, 34, 38, 42, 46, 50, 54, 58, 62, 66, 70, 76, 82, 88, 94 and 100, or the heavy chain variable region includes the amino acid sequence selected from the group consisting of SEQ ID NO: 2, 6, 10, 14, 18, 22, 26, 30, 34, 38, 42, 46, 50, 54, 58, 62, 66, 70, 76, 82, 88, 94 and 100.

In some embodiments, the antibody specifically binding to IL-4 receptor alpha or the antigen-binding fragment thereof further includes a light chain variable region, where the light chain variable region includes an LCDR1, LCDR2 and/or LCDR3 sequence. In some embodiments, the LCDR1 sequence includes an amino acid sequence selected from the group consisting of SEQ ID NO: 108, 114, 120, 126, 132, 138, 144, 150, 156, 162, 168, 174, 180, 186, 192, 198 and 204. In some embodiments, the LCDR2 sequence includes an amino acid sequence selected from the group consisting of SEQ ID NO: 109, 115, 121, 127, 133, 139, 145, 151, 157, 163, 169, 175, 181, 187, 193, 199 and 205. In some embodiments, the LCDR3 sequence includes an amino acid sequence selected from the group consisting of SEQ ID NO: 110, 116, 122, 128, 134, 140, 146, 152, 158, 164, 170, 176, 182, 188, 194, 200 and 206.

In some embodiments, the light chain variable region includes an amino acid sequence having at least 80% homology with an amino acid sequence selected from the group consisting of SEQ ID NO: 4, 8, 12, 16, 20, 24, 28, 32, 36, 40, 44, 48, 52, 56, 60, 64, 68, 73, 79, 85, 91, 97 and 103; or the light chain variable region includes s an amino acid sequence selected from the group consisting of SEQ ID NO: 4, 8, 12, 16, 20, 24, 28, 32, 36, 40, 44, 48, 52, 56, 60, 64, 68, 73, 79, 85, 91, 97 and 103.

In some embodiments, the antibody specifically binding to IL-4 receptor alpha or the antigen-binding fragment thereof includes a heavy chain including an amino acid sequence selected from a group consisting of SEQ ID NO: 71, 77, 83, 89, 95 and 101 or an amino acid sequence having at least 80% homology with the sequence. Optionally, the antibody or the antigen-binding fragment thereof includes a light chain including an amino acid sequence selected from the group consisting of SEQ ID NO: 74, 80, 86, 92, 98 and 104 or an amino acid sequence having at least 80% homology with the sequence.

In some embodiments, the antibody specifically binding to IL-4 receptor alpha according to the first aspect is a monoclonal antibody.

In some embodiments, the antibody specifically binding to IL-4 receptor alpha according to the first aspect is a humanized antibody.

In some embodiments, the antibody specifically binding to IL-4 receptor alpha or the antigen-binding fragment thereof disclosed herein binds to the same epitope on IL-4 receptor alpha with an antibody 131-Hu, 136-Hu or 236-Hu, or competes with the antibody 131-Hu, 136-Hu or 236-Hu to bind to IL-4 receptor alpha, where the antibody 131-Hu has a heavy chain sequence as shown in SEQ ID NO: 83, and a light chain sequence as shown in SEQ ID NO: 86; the antibody 136-Hu has a heavy chain sequence as shown in SEQ ID NO: 89, and a light chain sequence as shown in SEQ ID NO: 92; and the antibody 236-Hu has a heavy chain sequence as shown in SEQ ID NO: 101, and a light chain sequence as shown in SEQ ID NO: 104.

In some embodiments, the antibody or the antigen-binding fragment thereof disclosed herein can inhibit IgE secretion of B cells. In some embodiments, the antibody or the antigen-binding fragment thereof binds to IL-4R alpha at a KD less than 600 pM, preferably less than 350 pM. In some other embodiments, the antibody or the antigen-binding fragment thereof can inhibit IL-4-induced TF-1 cell proliferation.

According to a second aspect, this application provides a nucleotide molecule that encodes the antibody specifically binding to IL-4 receptor alpha or the antigen-binding fragment thereof.

According to a third aspect, this application provides an expression vector including the nucleotide molecule as already mentioned.

In some embodiments, the expression vector is pTT5, pUC57, pDR1, pcDNA3.1(+), pDHFF or pCHO 1.0, or the like.

According to a fourth aspect, this application provides a host cell including the expression vector as already mentioned. In some embodiments, the host cell is HEK293, COS, CHO, NS0, sf9, sf21, DH5u, BL21 (DE3) or TG1, or the like.

According to a fifth aspect, this application provides a method for preparing the antibody specifically binding to IL-4 receptor alpha or the antigen-binding fragment thereof according to the first aspect, the method includes the following steps:

a) culturing the host cell according to the fourth aspect under expression conditions that enable the host cell to produce the antibody or antigen-binding fragment thereof, thereby expressing the antibody or the antigen-binding fragment thereof; and b) separating and purifying the antibody or the antigen-binding fragment thereof expressed in the step a).

According to a sixth aspect, this application provides a pharmaceutical composition including the anti-IL-4 receptor alpha antibody or the antigen-binding fragment thereof according to the first aspect and pharmaceutically acceptable carriers.

In some embodiments, the composition is used for treating IL-4R alpha related diseases.

According to a seventh aspect, this application provides an application of the anti-IL-4 receptor alpha antibody or the antigen-binding fragment thereof according to the first aspect, or the composition according to the sixth aspect in the preparation of drugs for preventing or treating IL-4R alpha related diseases, such as immune-mediated inflammatory responses or inflammatory diseases.

In some embodiments, the immune-mediated inflammatory responses or inflammatory diseases include: asthma, allergy, atopic dermatitis, chronic sinusitis, eosinophilic esophagitis, nasal polyps, psoriasis, rheumatoid arthritis, psoriasis arthritis, ankylosing spondylitis, multiple sclerosis, uveitis, Behçet's uveitis, xerophthalmia and chronic spontaneous urticaria.

According to other aspects, this application provides a method for preventing or treating IL-4R alpha related diseases, the method includes administering the antibody or the antigen-binding fragment thereof according to the first aspect or the pharmaceutical composition according to the sixth aspect to an individual in need.

The anti-IL-4R alpha antibody or the antigen-binding fragment thereof according to the present invention can specifically bind to IL-4R alpha, and has one or more of the following effects: blocking the binding of IL-4 or IL-13 to IL-4R alpha; inhibiting IL-4 or IL-13 induced cell line (such as TF-1 cells) proliferation; and/or inhibiting IgE secretion of B cells. In vivo pharmacodynamic experiments fully show that the antibody according to the present invention can antagonize the occurrence of downstream Th2 responses by inhibiting IL-4 and IL-13 signaling pathways, has a strong asthma inhibition function, and takes effect quickly. The anti-IL-4R alpha antibody or the antigen-binding fragment thereof according to the present invention can be used for preventing or treating IL-4R alpha related diseases, such as immune-mediated inflammatory diseases.

DETAILED DESCRIPTION OF THE EMBODIMENTS

Figure 1:
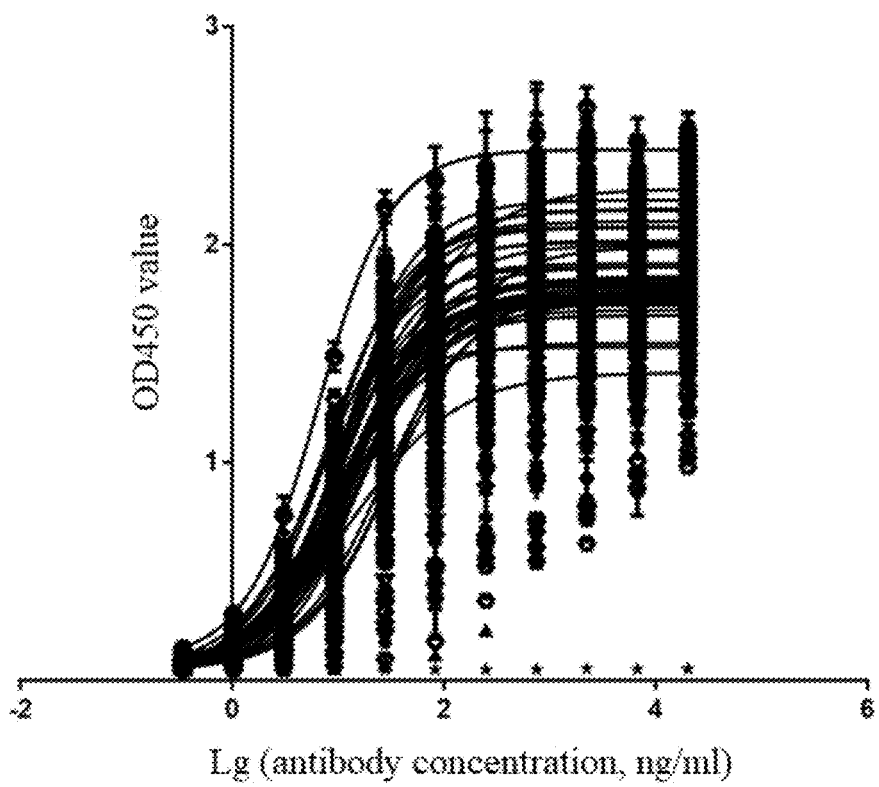
FIG. 1 shows the results of affinity of murine anti-hIL-4R alpha monoclonal antibodies for human IL-4R alpha.

This application provides a new anti-IL-4R alpha antibody specifically binding to IL-4R alpha, or an antigen-binding fragment thereof. In a preferred embodiment, the antibody or the antigen-binding fragment thereof according to this application binds to human IL-4R alpha with high affinity and inhibits the activity of IL-4R alpha. This application further provides polynucleotide encoding the antibody or an antigen-binding fragment thereof, a vector containing the polynucleotide, a host cell containing the polynucleotide or the vector, a method for preparing and purifying the antibody, and medical and biological applications of the antibody or the antigen-binding fragment thereof, such as preventing or treating IL-4R alpha related diseases or disorders. This application also covers a method for detecting IL-4R alpha and regulating the activity of IL-4R alpha by using the antibody or the antigen-binding fragment thereof.

To understand this application easily, some terms used herein are first defined.

As used herein, the term "antibody" refers to an immunoglobulin molecule containing four polypeptide chains, namely, two heavy chains (H) and two light chains (L) interconnected by disulfide bonds, and a multimer thereof (e.g., IgM). Each heavy chain contains a heavy chain variable region (VH) and a heavy chain constant region (CH). The heavy chain constant region contains three domains: CH1, CH2 and CH3. Each light chain contains a light chain variable region (VL) and a light chain constant region (CL). The light chain constant region contains a domain (CL1). The VH and VL regions can be further subdivided into hypervariable regions called complementarity determining regions (CDRs), interspersed with conserved regions called framework regions (FRs).

As used herein, the term "antigen-binding fragment" of the antibody refers to a portion or a segment of a complete antibody molecule responsible for binding an antigen. An antigen-binding domain may include a heavy chain variable region (VH), a light chain variable region (VL) or both. An antigen-binding fragment of the antibody can be prepared from a complete antibody molecule by using any suitable standard technology, including proteolytic digestion or recombinant genetic engineering technology, or the like. Non-limiting examples of the antigen-binding fragment include: an Fab fragment; an F(ab')2 fragment; an Fd fragment; an Fv fragment; a single chain Fv (scFv) molecule; a monodomain antibody; a dAb fragment and a minimum recognition unit (e.g., separated CDR) consisting of amino acid residues simulating the hypervariable region of the antibody. The term "antigen-binding fragment" also includes other engineered molecules, such as bi-antibody, tri-antibody, tetra-antibody and micro-antibody.

As used herein, the terms "heavy chain variable region (VH)" and "light chain variable region (VL)" refer to variable heavy chain and light chain regions of a single antibody, respectively, including FRI, 2, 3 and 4 and CDR 1, 2 and 3.

It is well known to those skilled in the biology field that complementarity determining regions (CDRs, usually referring to CDR1, CDR2 and CDR3) are variable regions that have the greatest influence on affinity and specificity of antibodies. Two common definitions are available to CDR sequences of VH or VL, namely, definitions by Kabat definition and Chothia, for example, see Kabat et al, "Sequences of Proteins of Immunological Interest", National Institutes of Health, Bethesda, Md. (1991); Al-Lazikani et al., J. Mol. Biol. 273:927-948 (1997); and Martin et al., Proc. Natl. Acad. Sci. USA 86:9268-9272 (1989). For a variable region sequence of a given antibody, CDR region sequences in VH and VL sequences can be determined based on the definitions by Kabat or Chothia. In the embodiments of this application, the CDR sequence is defined by Kabat. In this application, CDR1, CDR2 and CDR3 of the heavy chain variable region are referred to as HCDR1, HCDR2 and HCDR3, respectively; and CDR1, CDR2 and CDR3 of the light chain variable region are referred to as LCDR1, LCDR2 and LCDR3, respectively.

For the variable region sequence of the given antibody, a CDR region sequence in the variable region sequence can be analyzed in multiple ways, for example, the CDR region sequence can be determined by online software Abysis (www.abysis.org/).

As used herein, the term "specific binding" refers to a non-random binding reaction between two molecules, such as the binding of the antibody to an antigen epitope, such as the ability of the antibody to bind to a specific antigen with an affinity that is at least two times greater than its affinity for a nonspecific antigen. However, it should be understood that the antibody can specifically bind to two or more antigens related to sequences of the antibody. For example, the antibody according to the present invention can specifically bind to human and non-human (such as mice or non-human primates) IL-4R alpha.

As used herein, the term "monoclonal antibody" refers to an antibody obtained from a basically homogeneous antibody population, that is, antibodies that make up the population are identical except for the possible naturally occurring mutations in a small number of individuals. The monoclonal antibody described herein particularly includes a "chimeric" antibody, in which a part of the heavy chain and/or light chain is identical to or homologous with a corresponding sequence in an antibody from a specific species or belonging to a specific antibody class or subclass, while the rest of the heavy chain and/or light chain is identical to or homologous with a corresponding sequence in an antibody from another species or belonging to another antibody class or subclass; and the monoclonal antibody also includes fragments of such antibody, as long as they exhibit the desired bioactivity (see U.S. Pat. No. 4,816,567; and Morrison et al, Proc. Natl. Acad. Sci. USA 81:6851-6855 (1984)).

As used herein, the term "homology" is defined as the percentage of identical residues in amino acid or nucleotide sequence variants after sequence alignment and introduction of gaps, which can be up to the maximum percentage if required. Methods and computer programs for alignment are well known in the art. As used herein, "at least 80% homology" refers to any value from 80% to 100% homology, such as 85%, 90%, 95% and 99%.

As used herein, the term "IL-4R alpha related diseases" includes diseases and/or symptoms related to the activation of IL-4R alpha signaling pathways. Exemplary IL-4R alpha related diseases or disorders include immune-mediated inflammatory responses, such as allergic diseases and asthma.

As used herein, the terms "half life" and "serum half life" refer to the time spent in reducing the serum concentration of an antigen-binding protein according to the present disclosure by 50% in vivo.

According to a first aspect, this application provides an antibody specifically binding to IL-4R alpha or an antigen-binding fragment thereof, including a heavy chain variable region and/or a light chain variable region. The CDR, VH, VL, heavy chain and light chain amino acid sequences and corresponding nucleotide sequences applicable to the antibody disclosed in this application are listed in the following Tables 1 to 5. In some embodiments, the anti-IL-4R alpha antibody or the antigen-binding fragment thereof includes HCDR3, HCDR2 and/or HCDR1 sequences, which are independently selected from any of the HCDR3, HCDR2 or HCDR1 sequences shown in Table 1. In some embodiments, the anti-IL-4R alpha antibody according to this application can further include a light chain CDR, which is independently selected from any of the light chain CDR1, CDR2 or CDR3 sequences shown in Table 2. For example, the anti-IL-4R alpha antibody according to this application can include any of the heavy chain variable domains shown in Tables 3 and 4, being optionally paired with any of the light chain variable domains shown in Tables 3 and 4.

TABLE 1

Amino acid sequences of heavy chain CDRs of exemplary anti-IL-4R alpha antibodies

| Antibody number | Sequence number corresponding to HCDR1 (SEQ ID NO.) | Sequence number corresponding to HCDR2 (SEQ ID NO.) | Sequence number corresponding to HCDR3 (SEQ ID NO.) |
|---|---|---|---|
| 29 | 105 | 106 | 107 |
| 59 | 111 | 112 | 113 |
| 120 | 117 | 118 | 119 |
| 131 | 123 | 124 | 125 |
| 136 | 129 | 130 | 131 |
| 54 | 135 | 136 | 137 |
| 55 | 141 | 142 | 143 |
| 57 | 147 | 148 | 149 |
| 64 | 153 | 154 | 155 |
| 75 | 159 | 160 | 161 |
| 81 | 165 | 166 | 167 |
| 83 | 171 | 172 | 173 |
| 84 | 177 | 178 | 179 |
| 88 | 183 | 184 | 185 |
| 100 | 189 | 190 | 191 |
| 228 | 195 | 196 | 197 |
| 236 | 201 | 202 | 203 |

TABLE 2

Amino acid sequences of light chain CDRs of exemplary anti-IL-4R alpha antibodies

| Antibody number | Sequence number corresponding to LCDR1 (SEQ ID NO.) | Sequence number corresponding to LCDR2 (SEQ ID NO.) | Sequence number corresponding to LCDR3 (SEQ ID NO.) |
|---|---|---|---|
| 29 | 108 | 109 | 110 |
| 59 | 114 | 115 | 116 |
| 120 | 120 | 121 | 122 |
| 131 | 126 | 127 | 128 |
| 136 | 132 | 133 | 134 |
| 54 | 138 | 139 | 140 |
| 55 | 144 | 145 | 146 |
| 57 | 150 | 151 | 152 |
| 64 | 156 | 157 | 158 |
| 75 | 162 | 163 | 164 |
| 81 | 168 | 169 | 170 |
| 83 | 174 | 175 | 176 |
| 84 | 180 | 181 | 182 |
| 88 | 186 | 187 | 188 |
| 100 | 192 | 193 | 194 |
| 228 | 198 | 199 | 200 |
| 236 | 204 | 205 | 206 |

TABLE 3

Nucleotide sequences and amino acid sequences of heavy chain variable regions and light chain variable regions of exemplary anti-IL-4R alpha antibodies

| Antibody number | Nucleotide sequence of heavy chain variable region (SEQ ID NO.) | Nucleotide sequence of light chain variable region (SEQ ID NO.) | Amino acid sequence of heavy chain variable region (SEQ ID NO.) | Amino acid sequence of light chain variable region (SEQ ID NO.) |
|---|---|---|---|---|
| 29 | 1 | 3 | 2 | 4 |
| 59 | 5 | 7 | 6 | 8 |
| 120 | 9 | 11 | 10 | 12 |
| 131 | 13 | 15 | 14 | 16 |
| 136 | 17 | 19 | 18 | 20 |
| 54 | 21 | 23 | 22 | 24 |
| 55 | 25 | 27 | 26 | 28 |
| 57 | 29 | 31 | 30 | 32 |
| 64 | 33 | 35 | 34 | 36 |
| 75 | 37 | 39 | 38 | 40 |
| 81 | 41 | 43 | 42 | 44 |
| 83 | 45 | 47 | 46 | 48 |
| 84 | 49 | 51 | 50 | 52 |
| 88 | 53 | 55 | 54 | 56 |
| 100 | 57 | 59 | 58 | 60 |
| 228 | 61 | 63 | 62 | 64 |
| 236 | 65 | 67 | 66 | 68 |

TABLE 4

Nucleotide sequences and amino acid sequences of heavy chain variable regions and light chain variable regions of exemplary humanized anti-IL-4R alpha antibodies

| Antibody | Nucleotide sequence of heavy chain variable region (SEQ ID NO.) | Nucleotide sequence of light chain variable region (SEQ ID NO.) | Amino acid sequence of heavy chain variable region (SEQ ID NO.) | Amino acid sequence of light chain variable region (SEQ ID NO.) |
|---|---|---|---|---|
| 29-Hu | 69 | 72 | 70 | 73 |
| 59-Hu | 75 | 78 | 76 | 79 |
| 131-Hu | 81 | 84 | 82 | 85 |
| 136-Hu | 87 | 90 | 88 | 91 |
| 228-Hu | 93 | 96 | 94 | 97 |
| 236-Hu | 99 | 102 | 100 | 103 |

TABLE 5

Amino acid sequences of heavy chain and light chain
of exemplary anti-IL-4R alpha antibodies

| Antibody | Amino acid sequence of heavy chain (SEQ ID NO.) | Amino acid sequence of light chain (SEQ ID NO.) |
|---|---|---|
| 29-Hu | 71 | 74 |
| 59-Hu | 77 | 80 |
| 131-Hu | 83 | 86 |
| 136-Hu | 89 | 92 |
| 228-Hu | 95 | 98 |
| 236-Hu | 101 | 104 |

In some embodiments, the HCDR3 of the antibody or the antigen-binding fragment thereof disclosed herein is selected from an amino acid sequence as shown in SEQ ID NO: 107, 113, 119, 125, 131, 137, 143, 149, 155, 161, 167, 173, 179, 185, 191, 197 and 203. In some embodiments, the HCDR2 is selected from an amino acid sequence as shown in SEQ ID NO: 106, 112, 118, 124, 130, 136, 142, 148, 154, 160, 166, 172, 178, 184, 190, 196 and 202; and/or the HCDR1 is selected from an amino acid sequence as shown in SEQ ID NO: 105, 111, 117, 123, 129, 135, 141, 147, 153, 159, 165, 171, 177, 183, 189, 195 and 201.

In a specific embodiment, the HCDR3 is selected from an amino acid sequence as shown in SEQ ID NO: 107, 113, 119, 125 and 131. In another specific embodiment, the HCDR3 is selected from an amino acid sequence as shown in SEQ ID NO: 137, 143, 149, 155, 161, 167, 173, 179, 185, 191, 197 and 203. In a preferred embodiment, the HCDR3 is selected from an amino acid sequence as shown in 125, 131 and 203.

In a specific embodiment, the HCDR2 is selected from an amino acid sequence as shown in SEQ ID NO: 106, 112, 118, 124 and 130. In another specific embodiment, the HCDR2 is selected from an amino acid sequence as shown in SEQ ID NO: 136, 142, 148, 154, 160, 166, 172, 178, 184, 190, 196 and 202. In a preferred embodiment, the HCDR2 is selected from an amino acid sequence as shown in 124, 130 and 202.

In a specific embodiment, the HCDR1 is selected from an amino acid sequence as shown in SEQ ID NO: 105, 111, 117, 123 and 129. In another specific embodiment, the HCDR1 is selected from an amino acid sequence as shown in SEQ ID NO: 135, 141, 147, 153, 159, 165, 171, 177, 183, 189, 195 and 201. In a preferred embodiment, the HCDR1 is selected from an amino acid sequence as shown in 123, 129 and 201.

In some embodiments, the heavy chain variable region of the antibody disclosed herein includes an amino acid sequence selected from the group consisting of SEQ ID NO: 2, 6, 10, 14, 18, 22, 26, 30, 34, 38, 42, 46, 50, 54, 58, 62, 66, 70, 76, 82, 88, 94 and 100. In a specific embodiment, the heavy chain variable region includes an amino acid sequence selected from the group consisting of SEQ ID NO: 2, 6, 10, 14, 18, 22, 26, 30, 34, 38, 42, 46, 50, 54, 58, 62, 66, 70, 76, 82, 88, 94 and 100.

In some embodiments, the heavy chain variable region of the antibody disclosed herein includes an amino acid sequence having at least 80%, 90%, 91%, 92%, 93%, 94%, 95%, 96%, 97%, 98%, 99% homology with the sequence as shown in SEQ ID NO: 2, 6, 10, 14, 18, 22, 26, 30, 34, 38, 42, 46, 50, 54, 58, 62, 66, 70, 76, 82, 88, 94 or 100. In a preferred embodiment, the heavy chain variable region has more than 99% homology with the amino acid sequence as shown in SEQ ID NO: 82, 88 or 100.

The antibody or antigen-binding fragment thereof disclosed herein may further include a light chain variable region in addition to the heavy chain variable region.

In some embodiments, the light chain variable region includes a CDR3 (LCDR3) selected from an amino acid sequence as shown in SEQ ID NO: 110, 116, 122, 128 and 134, or selected from an amino acid sequence as shown in SEQ ID NO: 140, 146, 152, 158, 164, 170, 176, 182, 188, 194, 200 and 206. In a preferred embodiment, the LCDR3 is selected from an amino acid sequence as shown in SEQ ID NO: 128, 134 and 206.

In some embodiments, the LCDR2 is selected from an amino acid sequence as shown in SEQ ID NO: 109, 115, 121, 127 and 133, or selected from an amino acid sequence as shown in SEQ ID NO: 139, 145, 151, 157, 163, 169, 175, 181, 187, 193, 199 and 205. In a preferred embodiment, the LCDR2 is selected from an amino acid sequence as shown in SEQ ID NO: 127, 133 and 205.

In some embodiments, the LCDR1 is selected from an amino acid sequence as shown in SEQ ID NO: 108, 114, 120, 126, 132, 138, 144, 150, 156, 162, 168, 174, 180, 186, 192, 198 and 204, or selected from an amino acid sequence as shown in SEQ ID NO: 108, 114, 120, 126, 132, 138, 144, 150, 156, 162, 168, 174, 180, 186, 192, 198 and 204. In a preferred embodiment, the LCDR1 is selected from an amino acid sequence as shown in SEQ ID NO: 126, 132 and 204.

In some embodiments, the light chain variable region of the antibody disclosed herein includes an amino acid sequence selected from the group consisting of SEQ ID NO: 4, 8, 12, 16, 20, 24, 28, 32, 36, 40, 44, 48, 52, 56, 60, 64, 68, 73, 79, 85, 91, 97 and 103. In a specific embodiment, the light chain variable region includes an amino acid sequence selected from the group consisting of SEQ ID NO: 4, 8, 12, 16, 20, 24, 28, 32, 36, 40, 44, 48, 52, 56, 60, 64, 68, 73, 79, 85, 91, 97 and 103.

In some embodiments, the light chain variable region of the antibody disclosed herein includes an amino acid sequence having at least 80%, 90%, 91%, 92%, 93%, 94%, 95%, 96%, 97%, 98%, 99% homology with the sequence as shown in SEQ ID NO: 4, 8, 12, 16, 20, 24, 28, 32, 36, 40, 44, 48, 52, 56, 60, 64, 68, 73, 79, 85, 91, 97 or 103. In a preferred embodiment, the heavy chain variable region has more than 99% homology with the amino acid sequence as shown in SEQ ID NO: 85, 91 or 103.

In a specific embodiment, the antibody or antigen-binding fragment thereof disclosed herein comprises a heavy chain having at least 80% homology with an amino acid sequence selected from the group consisting of SEQ ID NO: 71, 77, 83, 89, 95 and 101, such as 90%, 91%, 92%, 93%, 94%, 95%, 96%, 97%, 98% and 99% homology. In a more specific embodiment, the heavy chain of the antibody includes an amino acid sequence selected from the group consisting of SEQ ID NO: 71, 77, 83, 89, 95 and 101. In a preferred embodiment, the heavy chain of the antibody has an amino acid sequence as shown in SEQ ID NO: 83, 89 or 101.

In a specific embodiment, the antibody disclosed herein includes a light chain having at least 80% homology with the sequence selected from the group consisting of SEQ ID NO: 74, 80, 86, 92, 98 and 104, such as 90%, 91%, 92%, 93%, 94%, 95%, 96%, 97%, 98% and 99% homology. In a more specific embodiment, the light chain of the antibody includes an amino acid sequence selected from the group consisting of SEQ ID NO: 74, 80, 86, 92, 98 and 104. In a preferred embodiment, the light chain of the antibody has an amino acid sequence as shown in SEQ ID NO: 86, 92 or 104.

In some embodiments, at least one amino acid can be subjected to substitution, deletion or addition on the corresponding specific amino acid sequences listed above in the heavy chain or heavy chain variable region, light chain or light chain variable region of the antibody disclosed herein, and a resulting variant still maintains the activity of binding IL-4R alpha.

In some embodiments, the number of amino acid substitution, deletion or addition is 1-30, preferably 1-20, and more preferably 1-10. In a preferred embodiment, the sequence variant differs from the original amino acid sequence by about 1, 2, 3, 4, 5, 6, 7, 8, 9, or 10 amino acid substitution, deletion or addition. In a more preferred embodiment, the sequence variant differs from the original amino acid sequence by about 1, 2, 3, 4 or 5 amino acid substitution, deletion or addition. In a specific embodiment, the amino acid substitution is conservative.

In a preferred embodiment, the antibody disclosed herein is an antibody 131-Hu, 136-Hu or 236-Hu, where the antibody 131-Hu has a heavy chain sequence as shown in SEQ ID NO: 83 and a light chain sequence as shown in SEQ ID NO: 86, with a CDR sequence the same as that of the antibody 131; the antibody 136-Hu has a heavy chain sequence as shown in SEQ ID NO: 89 and a light chain sequence as shown in SEQ ID NO: 92, with a CDR sequence the same as that of the antibody 136; and the antibody 236-Hu has a heavy chain sequence as shown in SEQ ID NO: 101 and a light chain sequence as shown in SEQ ID NO: 104, with a CDR sequence the same as that of the antibody 236.

In some embodiments, the antibody or the antigen-binding fragment thereof disclosed herein binds to the same epitope on IL-4 receptor alpha with an antibody 131-Hu, 136-Hu or 236-Hu, or competes with the antibody 131-Hu, 136-Hu or 236-Hu to bind to IL-4 receptor alpha.

In some embodiments, the antibody disclosed herein is a monoclonal antibody. In a specific embodiment, the antibody disclosed herein is a humanized antibody.

The antibody or the antigen-binding fragment thereof disclosed herein can specifically bind to IL-4R alpha. In a specific embodiment, the antibody or the antigen-binding fragment thereof specifically binds to human IL-4R alpha or mouse IL-4R alpha. In a preferred embodiment, the antibody or the antigen-binding fragment thereof specifically binds to human IL-4R alpha.

In some embodiments, the antibody or the antigen-binding fragment thereof binds to IL-4R alpha at a KD less than 600 pM. In a preferred embodiment, the antibody or the antigen-binding fragment thereof binds to IL-4R alpha (e.g., human IL-4R alpha) at a KD less than 350 pM.

In some embodiments, the antibody or the antigen-binding fragment thereof disclosed herein can inhibit IL-4-induced TF-1 cell proliferation. In some embodiments, the antibody or the antigen-binding fragment thereof disclosed herein can inhibit IgE secretion of B cells.

For example, the inventors of this application have conducted in vitro and in vivo biological experiments on the anti-hIL-4R alpha monoclonal antibody disclosed herein, with results showing that the antibody can bind to IL-4R alpha well.

Specifically, the inventors of this application have conducted affinity testing, experimental analysis on blocking the binding of IL-4/IL-13 to IL-4R alpha, in vitro cell function testing and other experiments on the anti-hIL-4R alpha monoclonal antibody. The results show that the anti-hIL-4R alpha monoclonal antibody disclosed herein can bind IL-4R alpha on cell surfaces, block the signal transduction between IL-4/IL-13 and IL-4R alpha, and inhibit the occurrence of inflammatory responses.

This application further provides a nucleotide molecule encoding the antibody or the antigen-binding fragment thereof disclosed herein, a vector containing the polynucleotide, a host cell containing the polynucleotide or the vector, and a method for preparing and purifying the antibody.

In some embodiments, the nucleotide molecule encoding the antibody or the antigen-binding fragment thereof is operably linked to a regulatory sequence that can be recognized by a host cell transfected with the vector.

In some embodiments, any suitable expression vector can be used in this application. For example, the expression vector can be one of pTT5, pUC57, pDRT, pcDNA3.1(+), pDHFF and pCHO 1.0. The expression vector may include a fusion DNA sequence linked with appropriate transcriptional and translational regulatory sequences.

In some embodiments, an available host cell is a cell containing the expression vector, which may be a eukaryotic cell. For example, a mammalian or insect host cell culture system can be used for the expression of the antibody or the antigen-binding fragment thereof according to this application. For example HEK293 cells, COS, CHO, NS0, sf9 and sf21 are applicable to the present invention. The host cell can also be a prokaryotic cell containing the expression vector, such as DH5 alpha, BL21 (DE3) or TGT.

In some embodiments, a method for preparing the anti-hIL-4R alpha monoclonal antibody disclosed herein includes the following steps: culturing the host cell under expression conditions to express the anti-hIL-4R alpha monoclonal antibody; and separating and purifying the expressed anti-hIL-4R alpha monoclonal antibody. A recombinant protein can be purified into an essentially homogeneous substance, such as a single band on SDS-PAGE, by the method.

In some embodiments, the anti-IL-4R alpha antibody disclosed herein can be separated and purified by affinity chromatography. Based on properties of an affinity column used, the anti-IL-4R alpha antibody binding to the affinity column can be eluted by a conventional method such as high salt buffer and pH changing.

In some embodiments, the humanized anti-hIL-4R alpha monoclonal antibody disclosed herein is obtained by the following method: immunizing Balb/c mice with an IL-4R alpha antigen prepared in the laboratory, fusing mouse spleen cells with hybridoma cells after a titer is higher through repeated immunization, and screening out hybridoma cell strains inhibiting IL-4 functional activity. More specifically, the inventors of this application have expressed an IL-4R alpha extracellular domain antigen, IL-4 and IL-13 respectively through a large number of experiments. On this basis, different adjuvants are mixed with the IL-4R alpha antigen to immunize mice, and then the mouse spleen cells are further fused with a hybridoma cell strain sp2/0. A positive cell strain is screened out from the fused hybridoma by using the IL-4R alpha extracellular domain antigen. After verifying that the positive cell strain blocks the binding of IL-4/IL-13 to IL-4R alpha and indeed inhibits the function of IL-4/IL-13, a target cell strain is obtained. After humanization of a target molecule, both light chain and heavy chain genes are cloned into a eukaryotic expression vector pCHO1.0. The expression vector is transfected into a CHO cell by lipofection, positive cell clones are screened with puromycin and methotrexate, and the screened high expression clones are propagated in a serum-free medium to separate or purify a humanized anti-hIL-4R alpha monoclonal antibody by a ProteinA affinity column.

In some other embodiments, a conventional technique in the art, such as PCR mutagenesis, can be used to further change a murine parental antibody to produce chimeric or humanized forms or other variant forms of the antibody. The parental antibody in this application can be mutated in a domain such as an antigen complementarity determining region (CDR) to produce a variant antibody that can be screened for the presence of target properties such as binding affinity (lower KD), IC50, specificity and priority binding. Preferably, the target properties in the variant antibody are improvements in properties in the parental antibody. Preferably, amino acids are substituted for the variant antibody, and at least 1, 2, 3, 4, 5, 6, 7, 8, 9 or 10 amino acid residues in molecules of the parental antibody are removed and different residues are inserted at corresponding positions. The most interesting site for alternative mutagenesis is one or more CDRs, but changes in a framework region (FR) are also considered. Conservative amino acid substitutions are preferred, non-conservative amino acid changes can also be introduced, and the obtained variant antibody can be used to screen target properties.

In some embodiments, the serum half-life of the antibody is prolonged by transforming an Fc region of the antibody. Identified mutation sites that can improve the binding ability of human FcRn to antibodies mainly include T250Q, M252Y, S254T, T256E, V308P, M428L, N434A and N434S. In this embodiment, the serum half-life of the antibody can be prolonged by mutation of amino acids at these sites.

This application provides a pharmaceutical composition, including the antibody or the antigen-binding fragment thereof disclosed herein and the pharmaceutically acceptable carrier. The anti-IL-4R alpha antibody disclosed herein, such as an anti-hIL-4R alpha monoclonal antibody, can be formulated into pharmacologic agents together with the pharmaceutically acceptable carrier to achieve more stable efficacy. In some embodiments, these agents can ensure the conformational integrity of an amino acid core sequence of the anti-IL-4R alpha antibody disclosed herein, such as the anti-hIL-4R alpha monoclonal antibody, while protecting multifunctional groups of proteins from degradation (including but not limited to aggregation, deamidation or oxidation). In some embodiments, liquid formulation can usually be kept stable at 2-8° C. for at least one year. In some embodiments, lyophilized formulation is kept stable at 30° C. for at least six months.

In some embodiments, formulation of the anti-IL-4R alpha antibody, such as the anti-hIL-4R alpha monoclonal antibody, can be suspensions, water injections, lyophilized formulation and the like commonly used in the pharmaceutical field, preferably water injections or lyophilized formulation. For a water injection or lyophilized formulation of the anti-IL-4R alpha antibody disclosed herein, such as the anti-hIL-4R alpha monoclonal antibody, pharmaceutically acceptable excipients include but are not limited to: surfactants, solution stabilizers, isotonic regulators and buffers or combinations thereof. In some embodiments, the surfactants include but are not limited to: nonionic surfactants such as polyoxyethylene sorbitan fatty acid ester (Tween 20 or 80), Poloxamer (e.g., Poloxamer 188), Triton, sodium dodecyl sulfate (SDS), sodium lauryl sulfate, tetradecyl, linoleic or octadecyl sarcosine, Pluronics and MONAQUAT™, which should be added in such an amount that can minimize granulation trend of the anti-hIL-4R alpha monoclonal antibody. In some embodiments, the solution stabilizers include but are not limited to one or a combination of: saccharides, such as reducing saccharides and non-reducing saccharides; amino acids, such as monosodium glutamate or histidine; alcohols, such as triols, higher sugar alcohols, propylene glycol and polyethylene glycol. An amount of the solution stabilizers added should be such that the final preparation formed keeps stable within the time considered stable by those skilled in the art. The isotonic regulators include but are not limited to: sodium chloride, mannitol or a combination thereof. The buffers include but are not limited to: Tris, histidine buffer, phosphate buffer or a combination thereof.

This application further provides a method for preventing or treating IL-4R alpha related diseases, including: administering an anti-IL-4R alpha antibody or a composition containing the anti-IL-4R alpha antibody such as an anti-hIL-4R alpha monoclonal antibody to an individual. In some embodiments, the effects on immune-mediated inflammatory responses are obvious after administration to animals including humans. Specifically, the anti-IL-4R alpha antibody disclosed herein can effectively prevent and/or treat immune-mediated inflammatory responses, and can be used as an anti-inflammatory drug.

This application further provides a use of the anti-IL-4R alpha antibody or the composition containing the anti-IL-4R alpha antibody in preparing drugs for preventing or treating IL-4R alpha related diseases or symptoms. In some embodiments, the IL-4R alpha related diseases or symptoms are immune-mediated inflammatory responses or immune-mediated inflammatory diseases.

In some embodiments, the immune-mediated inflammatory responses or immune-mediated inflammatory diseases include but are not limited to: asthma, allergy, atopic dermatitis, chronic sinusitis, eosinophilic esophagitis, nasal polyps, psoriasis, rheumatoid arthritis, psoriasis arthritsi, ankylosing spondylitis, multiple sclerosis, uveitis, Behçet's uveitis, xerophthalmia and chronic spontaneous urticaria. In addition to the inflammation-related diseases, the anti-IL-4R alpha antibody disclosed herein can also be used for preventing or treating multiple sclerosis, Crohn's disease, colitis, ulcerative colitis, systemic lupus erythematosus, graft-versus-host disease, or the like.

In some embodiments, the anti-IL-4R alpha antibody disclosed herein can be used as a drug for immune-mediated inflammatory responses. The drug for immune-mediated inflammatory responses as claimed in this application refers to a drug that can inhibit and/or treat immune-mediated inflammatory responses. For example, the drug can delay the development of symptoms related to immune-mediated inflammatory responses and/or reduce the severity of these symptoms. In some embodiments, the drug can alleviate concomitant symptoms of an existing inflammatory response and prevent the occurrence of other symptoms. In some embodiments, the drug can also reduce or prevent the metastasis of inflammatory responses.

When the anti-hIL-4R alpha monoclonal antibody and the composition thereof disclosed herein are administered to animals including humans, the dosage used varies with the ages and weights of patients, characteristics and seriousness of diseases, and routes of administration. Referring to results and comprehensive situations of animal experiments, and the total dosage used should not exceed a certain range. In a specific embodiment, a dose for intravenous injection is 1-1800 mg/day.

The dosage and frequency of application of the antibody or composition thereof may vary depending on prevention or treatment of diseases. In a preventive application, a composition containing the antibody according to this application or a mixture thereof is administered to a patient who has not been in a disease state yet to enhance resistance of the patient, and this amount is defined as a "preventive effective dose". In this use, the specific dose depends on health and systemic immunity of the patient. A relatively low dose is usually administered at a relatively infrequent interval over a long period of time. In a therapeutic application, relatively high doses are sometimes required at relatively short intervals until disease progression slows or stops, and preferably until the patient shows partial or complete improvement in disease symptoms. Thereafter, a preventive regimen can be administered to the patient. A person of ordinary skill in the art can easily master the specific dose and frequency based on actual needs.

In the specification and claims, the words "including", "comprising" and "containing" mean "including but not limited to", and are not intended to exclude other parts, additives, components or steps.

It should be understood that the features, characteristics, components or steps described in specific aspects, embodiments or examples of this application can be applied to any other aspects, embodiments or examples described herein unless there is a contradiction.

The above disclosure generally describes the present invention. The following specific examples are a further description of the present invention, and should not be construed as limiting the present invention. The examples do not include a detailed description of conventional methods.

Such methods are well known to a skilled person in the biology field, and have been described in many publications, such as Molecular Cloning Manual, and Antibody Technology Laboratory Manual published by Cold Spring Harbor Laboratory. Reagents without indication of sources are conventional reagents.

EXAMPLES

Example 1: Preparation of Soluble IL-4R Alpha Extracellular Domain Antigens with Fc Tag or Flag Tag, as Well as Reference Antibody Dupilumab and IL-4

An extracellular domain antigen sequence of human IL-4R alpha was derived from UniProt (UniProtKB-P24394). Codon optimization was carried out based on codon usage preference of *Cricetulus griseus*, and gene synthesis of N-terminal amino acid fragment at sites 26-232 was performed. The sequence was subcloned into a pUC57 vector to obtain pUC57-hIL4Rα-ECD. A constant region sequence of human IgG1 was synthesized based on a sequence of Secukinumab (see WHO Drug Information Vol. 23, No. 4, 2009, P342). The sequence was subcloned into a pUC57 vector to obtain pUC57-IgG1-CH. An hFc fragment or a Flag tag (DYKDDDDK, SEQ ID NO: 207) were inserted into a C-terminal of an hIL4R alpha-ECD fragment by PCR, and constructed on a pTT5 expression vector (stored in the laboratory) to obtain pTT5 (hIL4R alpha-ECD-hFc) and pTT5 (hIL4R alpha-ECD-Flag) for sequencing, and clones with correct sequences were selected for transfection.

An amino acid sequence of Dupilumab (IgG4, x) was from who.int (see WHO Drug Information Vol. 26, No. 4, 2012. P412). After codon optimization, a nucleotide sequence was synthesized and cloned into a pTT5 expression vector. Sequencing validation confirmed that a correct cloning vector labeled pTT5 (Dupilumab) was obtained. The pTT5 (Dupilumab) vector was transiently transfected into the HEK293E cell line. Cells were cultured in Freestyle293 medium containing 3 mM valproic acid for 5 days. Then Dupilumab antibody was purified from the cell culture supernatant by ProteinA affinity chromatography column (purchased from Pharmacia).

A human IL-4 sequence was derived from UniProt (UniProtKB-P05112). Codon optimization was carried out based on codon usage preference of *Cricetulus griseus*, and N-terminal amino acid fragment at sites 25-153 was synthesized. The sequence was subcloned into a pUC57 vector. A Flag tag (DYKDDDDK, SEQ ID NO: 207) was inserted into a C-terminal of an hIL4 fragment by PCR and constructed on a pTT5 expression vector to obtain pTT5 (hIL4-Flag) for sequencing, and clones with correct sequences were selected for transfection.

A plasmid was transfected into the HEK293E cell line (stored in the laboratory) by PEI. After cells were cultured in Freestyle293 medium containing 3 mM valproic acid (purchased from Gibco) for 5 days, a target protein was purified from the cell culture supernatant by ProteinA affinity chromatography column (purchased from Pharmacia) or Flag affinity chromatography beads (purchased from Sigma). The proteins were quantified by bicinchoninic acid (BCA), and the purified proteins were used for further analysis and research. The purified proteins were used for the following mouse immunization and further analysis and research.

Example 2: Immunization of hIL-4R Alpha-ECD-Fc

The hIL-4R alpha-ECD-Fc antigen in an amount of 100 g/mouse was diluted with normal saline to 75 μl and mixed with the same volume of Freund's Complete Adjuvant. After complete ultrasonic emulsification, 4-5-week-old Balb/c mice (purchased from Shanghai Lingchang Biotechnology Co., Ltd., animal production license number: SCXK (Shanghai) 2013-0018) were injected subcutaneously at multiple sites. Three weeks later, a protein in an amount of 50 g/mouse was diluted to 75 μl and mixed with the same volume of Freund's Incomplete Adjuvant. After complete ultrasonic emulsification, mice were injected subcutaneously at multiple sites, and the immunization was repeated two weeks later. One week after the third immunization, tails of all mice were cut off and blood was collected to separate serum, and the titer of serum antibody against hIL-4R was tested by ELISA coated with the hIL-4R alpha-Fc antigen. For mice with a serum antibody titer greater than 10,000, booster immunization was carried out one week after blood collection: tail vein injection of 10 μg antigen/100 μl normal saline/mouse.

The titer was tested by ELISA: an ELISA plate was coated with the hIL-4R alpha ECD-Fc antigen at a concentration of 1 μg/ml, 100 μl per well, and coated overnight at 4° C. The plates were washed twice with PBST (PBS containing 0.5% Tween-20) and then pat-dried. Each well was blocked with 200 μl of coating solution containing 1% BSA, blocked at room temperature for 4 h, pat-dried, and stored in a refrigerator at −20° C. for later use. During testing, 100 μl of mouse serum at different concentrations was added to each well of the ELISA plate, with two replicate wells, for incubation at room temperature for 1.5 h. The wells were washed with PBST for 3 times and then pat-dried. Then 100 μl of rabbit anti-mouse IgG labeled with HRP diluted with PBST by 1:10000 (purchased from Sigma) was added and the plates were incubated at room temperature for 1 h. The wells were washed with PBST for 3 times and then pat-dried. Then 100 μl of chromogenic solution was added to each well (an ELISA chromogenic solution A was mixed with a chromogenic solution B at a volume ratio of 1:1 before use) for a chromogenic reaction, and then 100 µl of 2M H2SO4 stopping solution was added to each well to terminate the reaction. The OD value of each well was immediately measured at 450 nm with a microplate reader (Molecular Device).

Example 3: Fusion and Screening of Hybridoma sp2/0 hybridoma cells (from the Cell Bank of the Committee on Type Culture Collection of Chinese Academy of Sciences, with a collection number of TCM-18) were cultured in a 5% CO2 incubator at 37° C., and the medium was changed one day before fusion. Three days after booster immunization, spleen cells were collected from mice for fusion. A fusion and screening method is described as follows: mouse spleen was ground and washed. Then spleen cells were counted and mixed with sp2/0 cells at a ratio of 10:1, and a resulting mixture was centrifuged at 1500 rpm for 7 min. A supernatant was washed off. Then 1 ml of PEG (1450) was added within 1 min, and shaken gently for 90 s, 5 ml of serum-free DMEM medium (purchased from Gibco) was added within 2.5 min, then another 5 ml of serum-free medium was added at one time to stop the reaction, a resulting mixture was allowed to stand for 5 min, and centrifuged at 1280 rpm for 8 min. With 2 million sp2/0 cells in a 96-well plate, the cells were uniformly inoculated into the 96-well plate, 200 µl per well. An HAT medium containing hypoxanthine (H), aminopterin (A) and thymidine (T) was used for screening, then half of the medium was changed every 3-4 days, and an HT medium was used on day 10. Ten days later, when hybridoma cells covered more than 10% of the bottom of the 96-well plate, the supernatant was tested by ELISA with the 96-well plate coated with the hIL-4R alpha-ECD-Fc antigen. The ELISA method was the same as that described in Example 2. Positive hybridomas were selected and cloned into a 24-well plate for propagation, and the propagated hybridomas were subcloned by limiting dilution to obtain hybridoma strains stably expressing a target antibody, and then a cell bank was built with preserved hybridoma strains.

Example 4: Blocking of Murine Anti-hIL-4R Alpha Monoclonal Antibodies on IL-4 Binding to hIL-4R Alpha ECD-Fc The blocking of murine anti-hIL-4R alpha monoclonal antibodies on IL-4 binding to hIL-4R alpha-ECD-Fc was investigated by ELISA. ELISA plates were coated with the hIL-4 protein, and after blocking, hIL-4R alpha-ECD-Fc and hybridoma cell culture supernatants of the murine anti-hIL-4R alpha monoclonal antibodies from 300 µl subclones were added, and finally an HRP-sheep anti-human IgG antibody was added for chromogenic testing. Cell strains that could block IL-4 binding to IL-4R alpha-ECD-Fc were preserved for the next round of subcloning.

Example 5: EC50 of Murine Anti-hIL-4R Alpha Monoclonal Antibodies Binding to Human IL-4R Alpha Optimized murine anti-hIL-4R alpha monoclonal antibodies were purified by a ProteinG affinity chromatography column and quantified by BCA. The EC50 of anti-hIL-4R alpha monoclonal antibodies binding to hIL-4R alpha was tested by ELISA. The testing method is as described in Example 3. An ELISA plate was coated with 1 µg/ml of hIL-4R alpha-ECD-Fc antigen, and then murine anti-hIL-4R alpha monoclonal antibodies at different concentrations were added for testing.

We analyzed 266 antibodies from preserved hybridomas, and representative experimental results were shown in FIG. 1. The EC50 data of some optimized antibodies were listed in Table 6. These antibodies had high affinity for human IL-4R alpha, and the EC50 was about 10 ng/ml.

TABLE 6

Affinity of exemplary murine anti-hIL-4R alpha monoclonal antibodies for human IL-4R alpha

| Antibody number | EC50 (ng/ml) |
|---|---|
| 29 | 7.6 |
| 54 | 9.9 |
| 55 | 8.9 |
| 57 | 7.9 |
| 59 | 11.7 |
| 64 | 10.6 |
| 75 | 12.9 |
| 81 | 9.6 |
| 83 | 12.3 |
| 84 | 12.2 |
| 88 | 9.1 |
| 100 | 12.0 |
| 120 | 10.0 |
| 131 | 13.8 |
| 136 | 11.3 |
| 228 | 13.1 |
| 236 | 11.5 |

Example 6: Inhibition of Murine Anti-hIL-4R Alpha Monoclonal Antibodies on hIL-4 or hIL-13-Induced TF-1 Cell Proliferation Hybridoma cell strains subjected to the third round of subcloning were propagated in serum-free media, and then cell supernatants were collected for antibody purification by ProteinG (purchased from GE) affinity columns. The purified antibodies were quantified and their functional activities were verified.

TF-1 cells are cytokine dependent cell strains separated from bone marrow of patients with human erythroid leukemia. Studies have shown that TF-1 cells grow well under the stimulation of hIL-4 or hIL-13, and therefore, TF-1 cells can become a better model for verifying functions of an IL-4 signaling pathway.

TF-1 cells (from ATCC, with collection number of CRL-2003) in a good growth state were counted, and resuspended with recombinant hIL-4 or hIL-13 (purchased from R&D Systems) at a final concentration of 20 ng/ml, then formed a 2×105/100 µl cell suspension. The medium is the RPMI1640 medium (purchased from Gibco) containing 10% fetal bovine serum (purchased from Sigma), 100 U/ml penicillin (purchased from Gibco) and 100 mg/ml streptomycin (purchased from Gibco), which is called RPMI-1640 complete medium. Murine anti-hIL-4R alpha monoclonal antibodies (20 µg/ml-3 ng/ml, serial dilution at a dilution ratio of 3, 9 different concentrations) at different concentrations were diluted with a medium solution, 100 µl per well, and added to 96-well flat cell culture plates (purchased from Corning), and then 100 µl of cell suspension was added to each well. Two replicate wells were set up in each group for incubation in 5% CO2 at 37° C. for 72 h. Then 20 µl of CCK-8 solution (purchased from Dojindo) was added to each well for continuing culture for 8 h. After the solution was mixed well, the OD value of each well was measured at 450 nm with a microplate reader, and a cell proliferation ratio was calculated.

Figure 2:
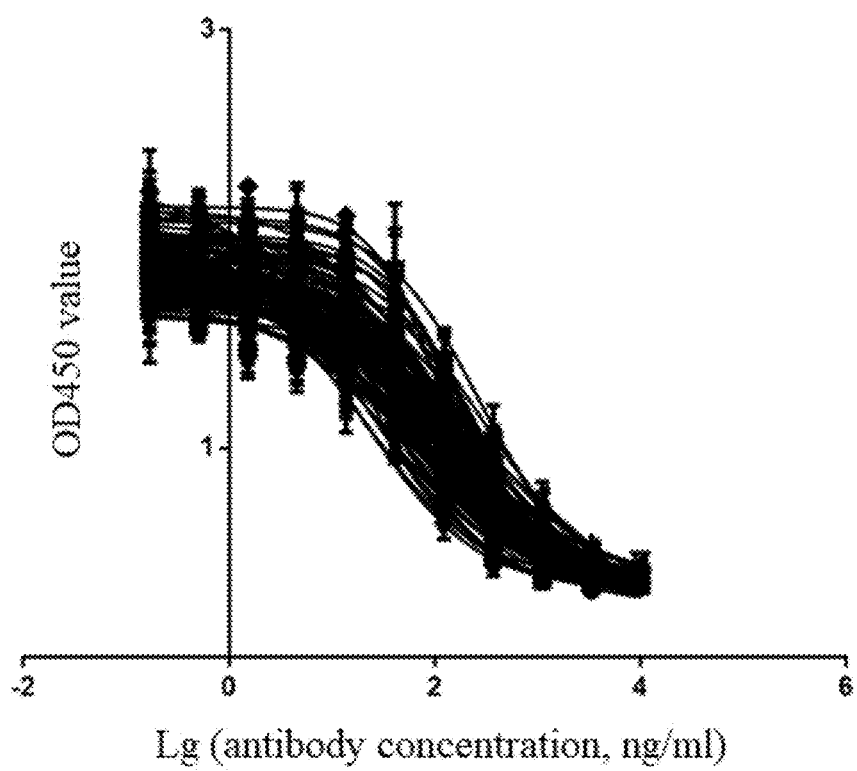
FIG. 2 shows the results of inhibiting human IL-4-induced TF-1 cell proliferation by murine anti-hIL-4R alpha monoclonal antibodies.

We analyzed the functional activity of the above 266 murine anti-hIL-4R alpha monoclonal antibodies in inhibiting IL-4-induced TF-1 cell proliferation (FIG. 2), and data on 17 optimized antibodies were shown in Table 7.

TABLE 7

Inhibition of IL-4-induced TF-1 proliferation by exemplary murine anti-hIL-4R alpha monoclonal antibodies

| Antibody number | IC50 (ng/ml) |
| --- | --- |
| 29 | 65.3 |
| 54 | 57.0 |
| 55 | 19.0 |
| 57 | 23.6 |
| 59 | 43.7 |
| 64 | 43.7 |
| 75 | 29.0 |
| 81 | 24.6 |
| 83 | 36.6 |
| 84 | 31.3 |
| 88 | 67.2 |
| 100 | 53.7 |
| 120 | 59.7 |
| 131 | 47.1 |
| 136 | 49.6 |
| 228 | 34.2 |
| 236 | 22.4 |

Example 7: Sequencing of Murine Anti-hIL-4R Alpha Monoclonal Antibodies

Total RNA of each hybridoma cell strain was extracted by Trizol (purchased from Sangon Biotech (Shanghai)), and mRNA was reversely transcribed into cDNA by a reverse transcription kit (purchased from Takara). Light chain variable region and heavy chain variable region genes of murine anti-hIL-4R alpha monoclonal antibodies were amplified by PCR with primers reported in the literature, and then PCR products were cloned into a pGEM-T vector, and variable region gene sequences were sequenced and analyzed. Based on results of various functional experiments and early development analysis, we finally selected 17 antibodies listed in Table 2 as leading antibodies, and sequenced to obtain nucleotide sequences of light and heavy chain variable regions. The transformed amino acid sequences were blasted in GenBank, and all sequences were consistent with the characteristics of mouse IgG variable region genes. Further sequence analysis showed that CDR sequences of light and heavy chains of antibodies 54, 55, 57, 64, 75, 81, 83, 84, 88, 100, 228 and 236 were highly similar, with differences in only a few amino acids, and CDR sequences of light and heavy chains of antibodies 29, 59, 120, 131 and 136 were highly similar. A nucleotide sequence of a heavy chain variable region of antibody 29 is shown in SEQ ID NO: 1, and an amino acid sequence of the heavy chain variable region is shown in SEQ ID NO: 2; a nucleotide sequence of a light chain variable region of antibody 29 is shown in SEQ ID NO: 3, and an amino acid sequence of the light chain variable region is shown in SEQ ID NO: 4. A nucleotide sequence of a heavy chain variable region of antibody 59 is shown in SEQ ID NO: 5, and an amino acid sequence of the heavy chain variable region is shown in SEQ ID NO: 6; a nucleotide sequence of a light chain variable region of antibody 59 is shown in SEQ ID NO: 7, and an amino acid sequence of the light chain variable region is shown in SEQ ID NO: 8. A nucleotide sequence of a heavy chain variable region of antibody 120 is shown in SEQ ID NO: 9, and an amino acid sequence of the heavy chain variable region is shown in SEQ ID NO: 10; a nucleotide sequence of a light chain variable region of antibody 120 is shown in SEQ ID NO: 11, and an amino acid sequence of the light chain variable region is shown in SEQ ID NO: 12. A nucleotide sequence of a heavy chain variable region of antibody 131 is shown in SEQ ID NO: 13, and an amino acid sequence of the heavy chain variable region is shown in SEQ ID NO: 14; a nucleotide sequence of a light chain variable region of antibody 131 is shown in SEQ ID NO: 15, and an amino acid sequence of the light chain variable region is shown in SEQ ID NO: 16. A nucleotide sequence of a heavy chain variable region of antibody 136 is shown in SEQ ID NO: 17, and an amino acid sequence of the heavy chain variable region is shown in SEQ ID NO: 18; a nucleotide sequence of a light chain variable region of antibody 136 is shown in SEQ ID NO: 19, and an amino acid sequence of the light chain variable region is shown in SEQ ID NO: 20. A nucleotide sequence of a heavy chain variable region of antibody 54 is shown in SEQ ID NO: 21, and an amino acid sequence of the heavy chain variable region is shown in SEQ ID NO: 22; a nucleotide sequence of a light chain variable region of antibody 54 is shown in SEQ ID NO: 23, and an amino acid sequence of the light chain variable region is shown in SEQ ID NO: 24. A nucleotide sequence of a heavy chain variable region of antibody 55 is shown in SEQ ID NO: 25, and an amino acid sequence of the heavy chain variable region is shown in SEQ ID NO: 26; a nucleotide sequence of a light chain variable region of antibody 55 is shown in SEQ ID NO: 27, and an amino acid sequence of the light chain variable region is shown in SEQ ID NO: 28. A nucleotide sequence of a heavy chain variable region of antibody 57 is shown in SEQ ID NO: 29, and an amino acid sequence of the heavy chain variable region is shown in SEQ ID NO: 30; a nucleotide sequence of a light chain variable region of antibody 57 is shown in SEQ ID NO: 31, and an amino acid sequence of the light chain variable region is shown in SEQ ID NO: 32. A nucleotide sequence of a heavy chain variable region of antibody 64 is shown in SEQ ID NO: 33, and an amino acid sequence of the heavy chain variable region is shown in SEQ ID NO: 34; a nucleotide sequence of a light chain variable region of antibody 64 is shown in SEQ ID NO: 35, and an amino acid sequence of the light chain variable region is shown in SEQ ID NO: 36. A nucleotide sequence of a heavy chain variable region of antibody 75 is shown in SEQ ID NO: 37, and an amino acid sequence of the heavy chain variable region is shown in SEQ ID NO: 38; a nucleotide sequence of a light chain variable region of antibody 75 is shown in SEQ ID NO: 39, and an amino acid sequence of the light chain variable region is shown in SEQ ID NO: 40. A nucleotide sequence of a heavy chain variable region of antibody 81 is shown in SEQ ID NO: 41, and an amino acid sequence of the heavy chain variable region is shown in SEQ ID NO: 42; a nucleotide sequence of a light chain variable region of antibody 81 is shown in SEQ ID NO: 43, and an amino acid sequence of the light chain variable region is shown in SEQ ID NO: 44. A nucleotide sequence of a heavy chain variable region of antibody 83 is shown in SEQ ID NO: 45, and an amino acid sequence of the heavy chain variable region is shown in SEQ ID NO: 46; a nucleotide sequence of a light chain variable region of antibody 83 is shown in SEQ ID NO: 47, and an amino acid sequence of the light chain variable region is shown in SEQ ID NO: 48. A nucleotide sequence of a heavy chain variable region of antibody 84 is shown in SEQ ID NO: 49, and an amino acid sequence of the heavy chain variable region is shown in SEQ ID NO: 50; a nucleotide sequence of a light chain variable region of antibody 84 is shown in SEQ ID NO: 51, and an amino acid sequence of the light chain variable region is shown in SEQ ID NO: 52. A nucleotide sequence of a heavy chain variable region of antibody 88 is shown in SEQ ID NO: 53, and an amino acid sequence of the heavy chain variable region is shown in SEQ ID NO: 54; a nucleotide sequence of a light chain variable region of antibody 88 is shown in SEQ ID NO: 55, and an amino acid sequence of the light chain variable region is shown in SEQ ID NO: 56. A nucleotide sequence of a heavy chain variable region of antibody 100 is shown in SEQ ID NO: 57, and an amino acid sequence of the heavy chain variable region is shown in SEQ ID NO: 58; a nucleotide sequence of a light chain variable region of antibody 100 is shown in SEQ ID NO: 59, and an amino acid sequence of the light chain variable region is shown in SEQ ID NO: 60. A nucleotide sequence of a heavy chain variable region of antibody 228 is shown in SEQ ID NO: 61, and an amino acid sequence of the heavy chain variable region is shown in SEQ ID NO: 62; a nucleotide sequence of a light chain variable region of antibody 228 is shown in SEQ ID NO: 63, and an amino acid sequence of the light chain variable region is shown in SEQ ID NO: 64. A nucleotide sequence of a heavy chain variable region of antibody 236 is shown in SEQ ID NO: 65, and an amino acid sequence of the heavy chain variable region is shown in SEQ ID NO: 66; a nucleotide sequence of a light chain variable region of antibody 236 is shown in SEQ ID NO: 67, and an amino acid sequence of the light chain variable region is shown in SEQ ID NO: 68.

Example 8: Humanization of Anti-hIL-4R Alpha Monoclonal Antibodies

Based on results of sequence analysis, antibodies 29, 59, 131, 136, 228 and 236 were selected to construct chimeric antibodies and humanized antibodies. The chimeric antibodies were constructed by intercepting heavy chain variable regions and light chain variable regions of murine antibodies, and connecting these regions with light and heavy chain constant regions of human IgG4 (from Dupilumab antibody) by overlapping PCR.

Amino acid sequences of light chain variable regions and heavy chain variable regions of murine anti-hIL-4R alpha monoclonal antibodies were analyzed based on Kabat rule, and three CDRs and four FRs were determined. Taking antibody 136 for example, amino acid sequences of a heavy chain complementarity determining regions of the antibody were HCDR1: DYGMH (SEQ ID NO: 129), HCDR2: YISSGSTTIYYADTVKG (SEQ ID NO: 130) and HCDR3: ISTVVAKRYAMDY (SEQ ID NO: 131), and amino acid sequences of a light chain complementarity determining regions were LCDR1: RASQDISNYLN (SEQ ID NO: 132), LCDR2: YTSRLHS (SEQ ID NO: 133) and LCDR3: QQINALPLT (SEQ ID NO: 134).

Based on the comparison of homology between NCBI IgBlast and human IgG Germline sequences, IGHV3-48*01 was selected as a heavy chain CDR grafting template, and a heavy chain CDR region of the murine anti-hIL-4R alpha monoclonal antibody 136 was grafted into a framework region of IGHV3-48*01 to construct a heavy chain CDR grafting antibody. Similarly, based on the comparison of homology with human IgG Germline sequences, IGKV1-33*01 was selected as a light chain CDR grafting template, and a light chain CDR region of the murine anti-hIL-4R alpha monoclonal antibody 136 was grafted into a framework region of IGKV1-33*01 to construct a light chain CDR grafting antibody, and the obtained antibody was defined as 136-Gr (136-Grafting). On this basis, some amino acid sites in the framework region were subjected to reverse mutation. During the reverse mutation, amino acid sequences were encoded by Kabat, and locations of the sites were indicated by Kabat codes. Preferably, for a light chain variable region sequence, F at site 73 of a Kabat code was reverted to murine L, and L at site 96 of CDR3 was mutated into F. There was no reverse mutation in the heavy chain variable region. The variable region gene sequences were optimized and synthesized by Sangon Biotech based on codon usage preference of Cricetulus griseus. The synthesized humanized variable region sequence was linked to a human IgG4 constant region, and this antibody was defined as a humanized antibody (136-Humanization, 136-Hu) of antibody 136.

Based on the same principle, the other five antibodies were humanized. Transiently expressed vectors of humanized heavy chains and light chains were constructed by a pTT5 vector (purchased from NRC Biotechnology Research Institute), then the plasmids were transiently transfected by the HEK293 system (purchased from NRC Biotechnology Research Institute), and antibodies were expressed. HEK293 cells were cultured in a FreeStyle 293 Expression Medium (purchased from Gibco). Plasmids were transfected into the cells by PEI transfection. Five days later, a cell supernatant was collected and purified by ProteinA to obtain an antibody.

Finally, a humanized heavy chain variable region of antibody 29 has a gene sequence with a total length of 366 bp, encoding 122 amino acid residues, with a nucleotide sequence as shown in SEQ ID NO: 69 and an amino acid sequence as shown in SEQ ID NO: 70; and a humanized light chain variable region has a gene sequence with a total length of 321 bp, encoding 107 amino acid residues, with a nucleotide sequence as shown in SEQ ID NO: 72 and an amino acid sequence as shown in SEQ ID NO: 73. After the heavy and the light chain variable regions were linked to the constant region of human IgG4, a humanized 29-Hu heavy chain with 448 amino acids (with a sequence as shown in SEQ ID NO: 71) and a humanized 29-Hu light chain with 214 amino acids (with a sequence as shown in SEQ ID NO: 74) were finally obtained.

A humanized heavy chain variable region of antibody 59 has a gene sequence with a total length of 354 bp, encoding 118 amino acid residues, with a nucleotide sequence as shown in SEQ ID NO: 75 and an amino acid sequence as shown in SEQ ID NO: 76; and a humanized light chain variable region has a gene sequence with a total length of 318 bp, encoding 106 amino acid residues, with a nucleotide sequence as shown in SEQ ID NO: 78 and an amino acid sequence as shown in SEQ ID NO: 79. After the heavy and the light chain variable regions were linked to the constant region of human IgG4, a humanized 59-Hu heavy chain with 444 amino acids (with a sequence as shown in SEQ ID NO: 77) and a humanized 59-Hu light chain with 213 amino acids (with a sequence as shown in SEQ ID NO: 80) were finally obtained.

A humanized heavy chain variable region of antibody 131 has a gene sequence with a total length of 366 bp, encoding 122 amino acid residues, with a nucleotide sequence as shown in SEQ ID NO: 81 and an amino acid sequence as shown in SEQ ID NO: 82; and a humanized light chain variable region has a gene sequence with a total length of 321 bp, encoding 107 amino acid residues, with a nucleotide sequence as shown in SEQ ID NO: 84 and an amino acid sequence as shown in SEQ ID NO: 85. After the heavy and the light chain variable regions were linked to the constant region of human IgG4, a humanized 131-Hu heavy chain with 448 amino acids (with a sequence as shown in SEQ ID NO: 83) and a humanized 131-Hu light chain with 214 amino acids (with a sequence as shown in SEQ ID NO: 86) were finally obtained.

A humanized heavy chain variable region of antibody 136 has a gene sequence with a total length of 366 bp, encoding 122 amino acid residues, with a nucleotide sequence as shown in SEQ ID NO: 87 and an amino acid sequence as shown in SEQ ID NO: 88; and a humanized light chain variable region has a gene sequence with a total length of 321 bp, encoding 107 amino acid residues, with a nucleotide sequence as shown in SEQ ID NO: 90 and an amino acid sequence as shown in SEQ ID NO: 91. After the heavy and the light chain variable regions were linked to the constant region of human IgG4, a humanized 136-Hu heavy chain with 448 amino acids (with a sequence as shown in SEQ ID NO: 89) and a humanized 136-Hu light chain with 214 amino acids (with a sequence as shown in SEQ ID NO: 92) were finally obtained.

A humanized heavy chain variable region of antibody 228 has a gene sequence with a total length of 360 bp, encoding 120 amino acid residues, with a nucleotide sequence as shown in SEQ ID NO: 93 and an amino acid sequence as shown in SEQ ID NO: 94; and a humanized light chain variable region has a gene sequence with a total length of 318 bp, encoding 106 amino acid residues, with a nucleotide sequence as shown in SEQ ID NO: 96 and an amino acid sequence as shown in SEQ ID NO: 97. After the heavy and the light chain variable regions were linked to the constant region of human IgG4, a humanized 228-Hu heavy chain with 446 amino acids (with a sequence as shown in SEQ ID NO: 95) and a humanized 228-Hu light chain with 213 amino acids (with a sequence as shown in SEQ ID NO: 98) were finally obtained.

A humanized heavy chain variable region of antibody 236 has a gene sequence with a total length of 360 bp, encoding 120 amino acid residues, with a nucleotide sequence as shown in SEQ ID NO: 99 and an amino acid sequence as shown in SEQ ID NO: 100; and a humanized light chain variable region has a gene sequence with a total length of 318 bp, encoding 106 amino acid residues, with a nucleotide sequence as shown in SEQ ID NO: 102 and an amino acid sequence as shown in SEQ ID NO: 103. After the heavy and the light chain variable regions were linked to the constant region of human IgG4, a humanized 236-Hu heavy chain with 446 amino acids (with a sequence as shown in SEQ ID NO: 101) and a humanized 236-Hu light chain with 213 amino acids (with a sequence as shown in SEQ ID NO: 104) were finally obtained.

Example 9: Affinity of Humanized Anti-hIL-4R Alpha Monoclonal Antibodies for IL-4R Alpha The affinity of six purified humanized antibodies was detected by Biacore T200 (GE healthcare), with the reference antibody Dupilumab as a control. The specific experimental method was as follows: a Protein-A CM5 sensor chip (GE healthcare) was used, with FCT (Flow cell 1) as a reference channel, and FC2 (Flow cell 2) as a sample channel. Humanized antibodies or control antibody were captured in the FC2 channel, and then hIL-4R alpha-ECD-Flag at different concentrations was injected. Cycling conditions were as follows: an analyte was injected into all channels of FCs at 50 μl/min for 4 min, with a dissociation time of 20 min, and 6M guanidine hydrochloride (Sinopharm Chemical Reagent Co., Ltd.) was injected at a rate of 10 μl/min for 30 s for surface regeneration. Then, signal differences and affinity for interaction between captured antibodies and non-captured antibodies were calculated by Biacore T200 Evaluation Software Ver 1.0. As shown in Table 8, the affinity of humanized antibodies 136-Hu and 236-Hu for hIL-4R alpha-ECD-Flag was significantly higher than that of the reference antibody Dupilumab.

TABLE 8

Affinity of different humanized antibodies for IL-4R alpha

| Antibody | Ka (1/Ms) | Kd (1/s) | KD (pM) |
| --- | --- | --- | --- |
| Dupilumab | $4.456 \times 10^5$ | $1.797 \times 10^{-4}$ | 403.1 |
| 29-hu | $3.982 \times 10^5$ | $2.096 \times 10^{-4}$ | 526.5 |
| 59-hu | $1.136 \times 10^6$ | $2.84 \times 10^{-4}$ | 250 |
| 131-hu | $3.35 \times 10^5$ | $1.107 \times 10^{-4}$ | 330 |
| 136-hu | $6.354 \times 10^5$ | $9.801 \times 10^{-5}$ | 154.2 |
| 228-hu | $7.211 \times 10^5$ | $6.578 \times 10^{-4}$ | 912.1 |
| 236-hu | $1.475 \times 10^6$ | $2.555 \times 10^{-4}$ | 173.2 |

Figure 3:
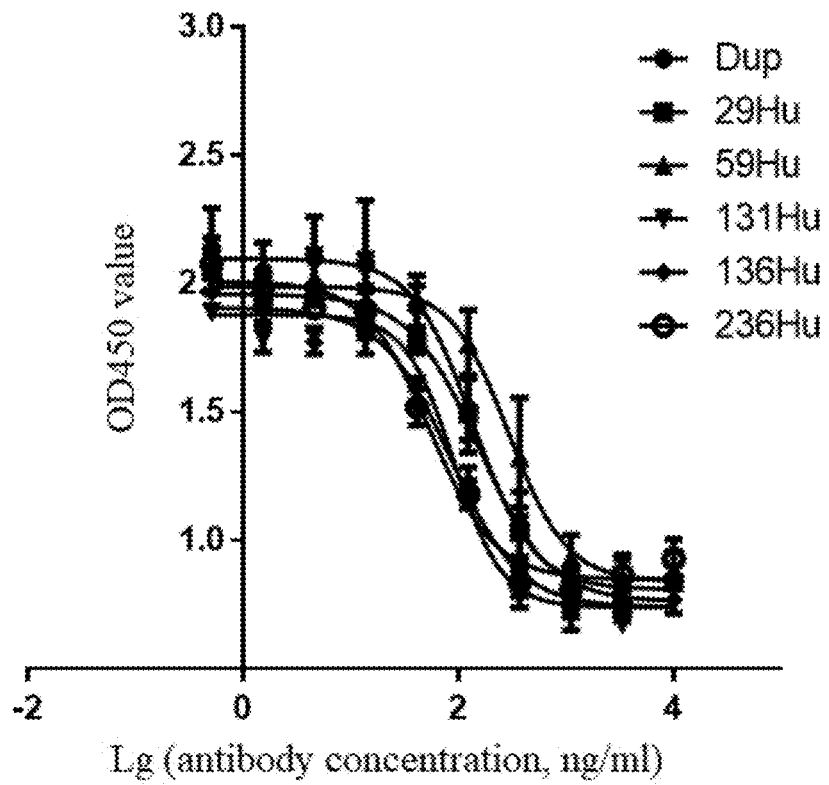
FIG. 3 shows the results of inhibiting human IL-4-induced TF-1 cell proliferation by a humanized anti-hIL-4R alpha monoclonal antibody.

Example 10: Inhibition of Humanized Anti-hIL-4R Alpha Monoclonal Antibodies on TF-1 Cell Proliferation The experiment on inhibition of TF-1 cell proliferation by humanized anti-hIL-4R alpha monoclonal antibodies was carried out with reference to Example 6. Results were shown in FIG. 3. As shown in Table 9, the inhibitory abilities of humanized antibodies 131-Hu, 136-Hu and 236-Hu on IL-4-mediated TF-1 cell proliferation were significantly higher than that of the reference antibody Dupilumab.

TABLE 9

Inhibition of different humanized antibodies on IL-4-induced TF-1 cell proliferation

| Antibody | IC50 (ng/ml) |
| --- | --- |
| Dupilumab | 137.9 |
| 29-hu | 155.9 |
| 59-hu | 295.5 |
| 131-hu | 90.6 |
| 136-hu | 84.3 |
| 236-hu | 54.6 |

Example 11: Inhibition of Humanized Anti-hIL-4R Alpha Monoclonal Antibodies on IgE Secretion of Peripheral Blood-Derived B Cells In the course of asthma, IL-4 and IL-13 induced IgM of B cells to transform into IgE. Then a large amount of IgE was secreted. After binding to receptors on surfaces of neutrophils, lymphocytes and mast cells, IgE activates immune responses that narrow respiratory airways and trigger an inflammatory response, resulting in aggravating asthma symptoms. Therefore, one of the functional activities of anti-hIL-4R alpha monoclonal antibodies was to inhibit IgE secretion of B cells. We verified this activity of humanized anti-hIL-4R alpha monoclonal antibodies.

Mononuclear cells were separated from fresh human peripheral blood (provided by Changhai Hospital) by Histopaque-1077 (purchased from Sigma). The cells were resuspended to form 5×105/ml cell suspension in an RPMI-1640 complete medium, and 100 μl of cell suspension was added to a 96-well cell culture plate. Meanwhile, 100 μl of 20 ng/ml recombinant hIL-4 and anti-hIL-4R alpha antibodies at different concentrations (20 µg/ml-3 ng/ml) were added for incubation in 5% CO2 at 37° C. for 14 days. Then, 100 µl of cell supernatant was pipetted to detect IgE concentration by ELISA.

Figure 4:
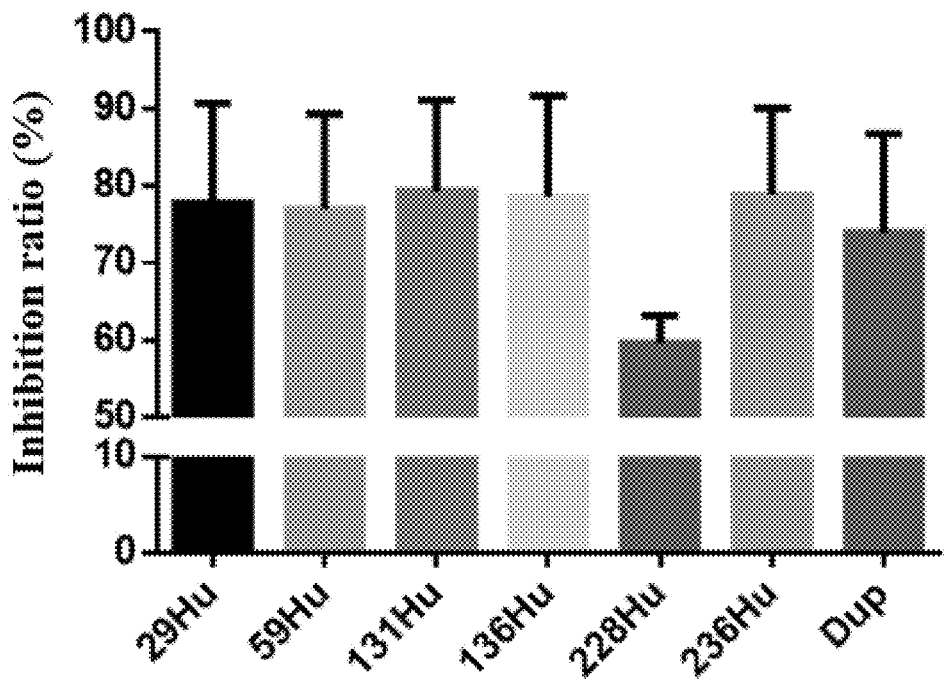
FIG. 4 shows the results of inhibiting IgE secretion of B cells from fresh peripheral blood by a humanized anti-hIL-4R alpha monoclonal antibody.

The ELISA assay method was described as follows: an ELISA plate (purchased from R&D Systems) was coated with mouse anti-human IgE at a concentration of 2.5 µg/ml, 100 µl per well, and coated overnight at 4° C. The plate was washed twice with PBST and then pat-dried. Each well was blocked at room temperature for 4 h with 200 µl of coating solution containing 1% BSA, and then pat-dried, and stored in a refrigerator at −20° C. for later use. During testing, human IgE standard compound (purchased from R&D Systems) at final concentrations of 100 ng/ml, 33 ng/ml, 11 ng/ml, 3.7 ng/ml, 1.2 ng/ml, 410 µg/ml, 130 µg/ml and 46 µg/ml respectively was prepared with a medium. Then the human IgE standard compound was added to the coated ELISA plate, 100 µl per well, with 2 replicate wells for each concentration; and 100 µl of cell supernatant was added to the coated ELISA plate for incubation at room temperature for 1.5 h. The wells were washed with PBST for 3 times and then pat-dried. To each well, 100 µl of biotinylated rat anti-human IgE (purchased from R&D Systems and diluted at a dilution ratio of 1000 with PBST containing 1% BSA) was added for incubation at room temperature for 1 h. The wells were washed with PBST for 3 times and then pat-dried. To each well, 100 µl of Streptavidin HRP (purchased from BD Pharmingen and diluted at a dilution ratio of 1000 with PBST containing 1% BSA) was added for incubation at room temperature for 1 h. Then 100 µl of chromogenic solution was added to each well (an ELISA chromogenic solution A was mixed with a chromogenic solution B at a volume ratio of 1:1 before use) for a chromogenic reaction, and then 100 µl of 2M H2SO4 stopping solution was added to each well to terminate the reaction. The OD value of each well was immediately measured at 450 nm with a microplate reader. Results showed that compared with Dupilumab, 131-Hu, 136-Hu and 236-Hu had higher inhibitory effects on IgE secretion of peripheral blood B cells, indicating that these antibodies had better functional activities than that of Dupilumab (FIG. 4).

Example 12: Pharmacokinetic Study on Humanized Anti-hIL-4R Alpha Monoclonal Antibodies in Cynomolgus Monkeys On the basis of humanized antibodies, Fc regions of the antibodies were modified. Mutation sites in Fc regions were mainly T250Q, M252Y, S254T, T256E, V308P, M428L, N434A and N434S. Half-life of antibody could be changed through changes in Fc, and longer half-life could reduce the frequency of administration.

Blood samples were collected at 0 h, 1 h, 4 h, 10 h, 24 h, 48 h, 72 h, 120 h, 168 h, 240 h, 336 h, 408 h, 504 h, 672 h, 840 h, 1008 h, 1176 h, 1344 h, 1512 h, 1680 h and 1848 h after a single administration to Cynomolgus monkeys for pharmacokinetic analysis. Serum concentrations of the antibodies were detected by the validated ELISA method. A quantitative range for assay in this study was 15.63-1,000.00 ng/mL, and standard samples at all concentration points were prepared from 100% serum of Cynomolgus monkeys. Pharmacokinetic parameters of an antibody in a non-mutated control group in an Fc region and a modified antibody in the Fc region after sc administration were shown in Table 10 and Table 11. There were two animals in each group, one male and one female, and the route of administration was subcutaneous injection (sc) at a dose of 5 mg/kg.

TABLE 10

Pharmacokinetic parameters of antibody in control group

| Parameter (unit) | Individual pharmacokinetic parameters | | Statistics All animals (n = 2) | CV |
|---|---|---|---|---|
| | 123 | 124 | Mean ± SD | % |
| $K_{el}$ (1/hr) | NA | 0.00258 | NA | NA |
| $t_{1/2}$ (hr) | NA | 268.75 | NA | NA |
| $T_{max}$ (hr) | 72 | 24 | 24~72 | 70.7 |
| $C_{max}$ (µg/mL) | 44.6 | 65.92 | 55.28 ± 15.05 | 27.2 |
| $AUC_{(0-t)}$ (hr · µg/mL) | 2639.085 | 28843.18 | 15741.13 ± 18529.09 | 117.7 |
| $AUC_{INF}$ (hr · µg/mL) | NA | 29064.18 | NA | NA |
| $AUC_{\%}$ (%) | NA | 0.76 | NA | NA |
| Vd (mL/kg) | NA | 66.701 | NA | NA |
| CL (mL/hr/kg) | NA | 0.172 | NA | NA |
| MRT (hr) | 41.492 | 355.289 | 198.39 ± 221.89 | 111.8 |

TABLE 11

Pharmacokinetic parameters of modified antibody in Fc region

| Parameter (unit) | Individual pharmacokinetic parameters | | Statistics All animals (n=2) | CV |
|---|---|---|---|---|
| | 127 | 128 | Mean ± SD | % |
| $K_{el}$ (1/hr) | 0.000656 | 0.000652 | 0.00065 ± 0.00 | 0.5 |
| $t_{1/2}$ (hr) | 1056.09 | 1063.86 | 1059.97 ± 5.49 | 0.5 |
| $T_{max}$ (hr) | 72 | 168 | 72~168 | 56.6 |
| $C_{max}$ (µg/mL) | 47.0 | 46.55 | 46.79 ± 0.34 | 0.7 |
| $AUC_{(0-t)}$ (hr · µg/mL) | 46806.50 | 54718.55 | 50762.52 ± 5594.67 | 11.0 |
| $AUC_{INF}$ (hr · µg/mL) | 68975.06 | 79997.09 | 74486.08 ± 7793.75 | 10.5 |
| $AUC_{\%}$ (%) | 32.14 | 31.60 | 31.87 ± 0.38 | 1.2 |
| Vd (mL/kg) | 110.45 | 95.93 | 103.19 ± 10.26 | 9.9 |
| CL (mL/hr/kg) | 0.0725 | 0.0625 | 0.0675 ± 0.0071 | 10.5 |
| MRT (hr) | 736.21 | 760.80 | 748.50 ± 17.38 | 2.3 |

Figure 5:
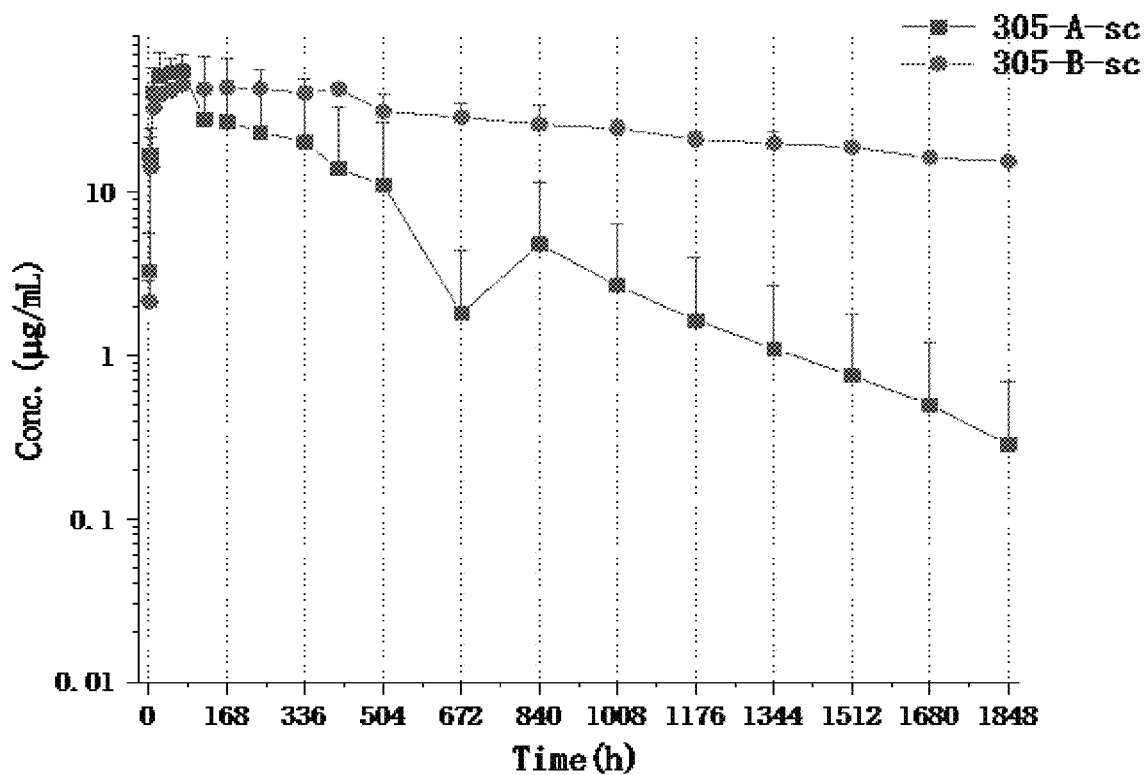
FIG. 5 shows the results of pharmacokinetic experiments on a humanized anti-hIL-4R alpha monoclonal antibody.

Compared with the control group, drug clearance of the modified antibody in the Fc region was relatively gentle after sc administration, and the serum half-life of the antibody was significantly prolonged (FIG. 5), in which 305-A-sc was the control group and 305-B-sc was the modified antibody in the Fc region. This experiment was entrusted to United-Power Pharma Tech Co., Ltd.

Example 13: Establishment of B-hIL-4/hIL-4RA Double Humanized Mouse Asthma Model and Efficacy Assessment of the Drug A target molecule was produced at pilot scale production and development of a formulation was conducted for the target molecule. The resulting 150 mg/ml stable product was named 305-B. For in vivo pharmacodynamic studies, IL-4/IL-4R alpha double humanized mice (B-hIL-4/hIL-4RA or B-hIL-4/IL4RA mice) were used. In these C57BL/6 background mice, murine IL-4 and IL-4R alpha were knocked out and replaced with humanized IL-4 and IL-4R alpha genes. Humanized mice behaved the same as normal mice, without any abnormality. The construction of humanized mice and the study on pharmacodynamics of 305-B in mouse asthma model were entrusted to Biocytogen Pharmaceuticals (Beijing) Co., Ltd.

An asthma model of mice sensitized by chicken Ovalbumin (OVA) was used in the experiment. Mice sensitized with OVA were challenged after aerosol inhalation of OVA, which triggered a Th2 immune response. An increase in eosinophil infiltration was observed in the lungs, and a significant increase in serum IgE concentration was observed. This model was used to evaluate the anti-allergic asthma function of the antibody. Dupilumab was used as a positive control, and 305-B was used as a test sample with a main component of humanized anti-hIL-4R alpha monoclonal antibody.

A total of 49 animals were randomly divided into 7 groups by weight, with 7 animals in each group. G1 was a PBS model group, G2 was a Dupilumab positive control (50 mg/kg) group, G3 was a test sample 305-B (0.5 mg/kg) group, G4 was a test sample 305-B (5 mg/kg) group, G5 was a test sample 305-B (25 mg/kg) group, G6 was a test sample 305-B (50 mg/kg) group, and G7 was a non-modeling Naïve group. All animals in the groups G1-G6 were sensitized by OVA: the mice were sensitized by intraperitoneal injection of OVA on day 0, 7 and 14, and stimulated by aerosol inhalation of OVA on day 21 to day 25. All animals in the groups were given drugs on day 20 and day 23.

Compared with the Naïve group, the serum IgE of the PBS model group increased significantly, and the percentage of eosinophils in white blood cells in bronchoalveolar lavage fluid increased significantly. Histopathological results showed that the infiltration of mixed inflammatory cells and eosinophils in lung tissues was significantly enhanced, and mucus secretion was significantly increased, suggesting that the modeling was successful.

Figure 6:
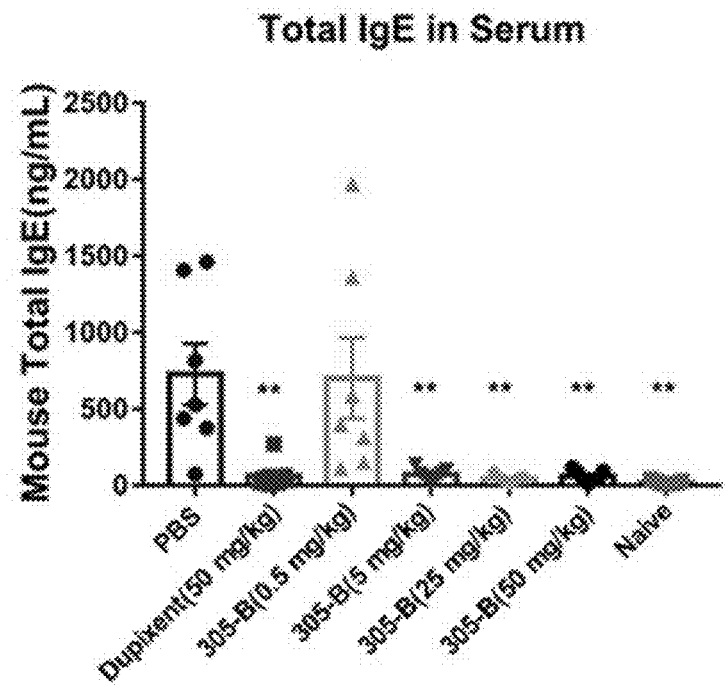
FIG. 6 shows inhibition of 305-B on serum IgE in model mice.
Figure 7:
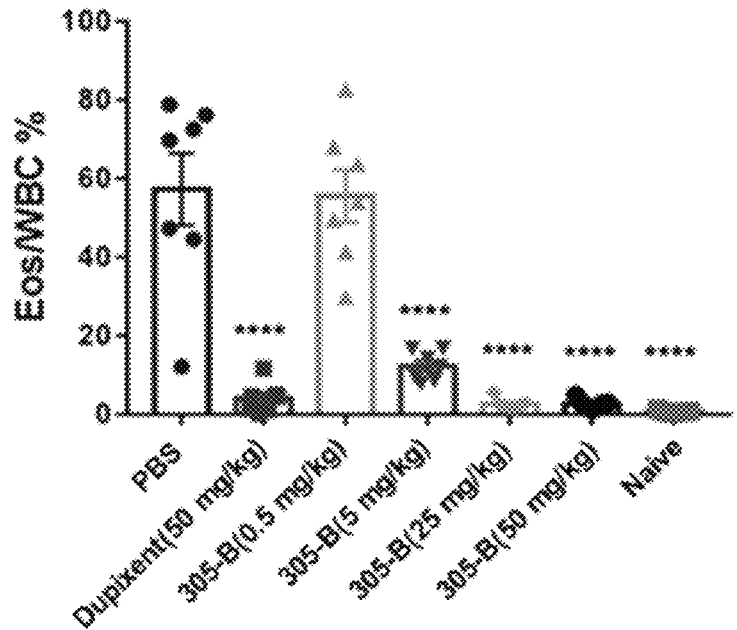
FIG. 7 shows the proportion of eosinophils to white blood cells in bronchoalveolar lavage fluid of animals in each model group.
Figure 8:
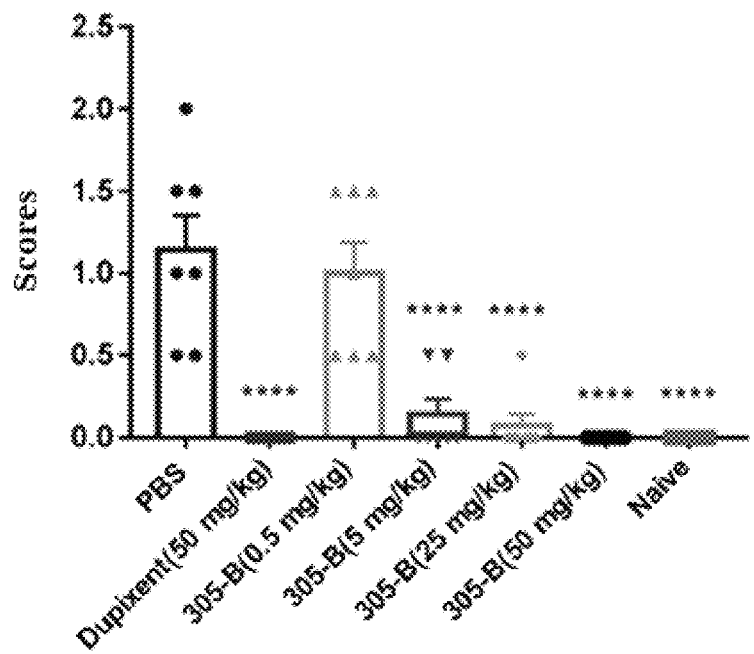
FIG. 8 shows eosinophil infiltration in lung tissues of animals in each model group.
Figure 9:
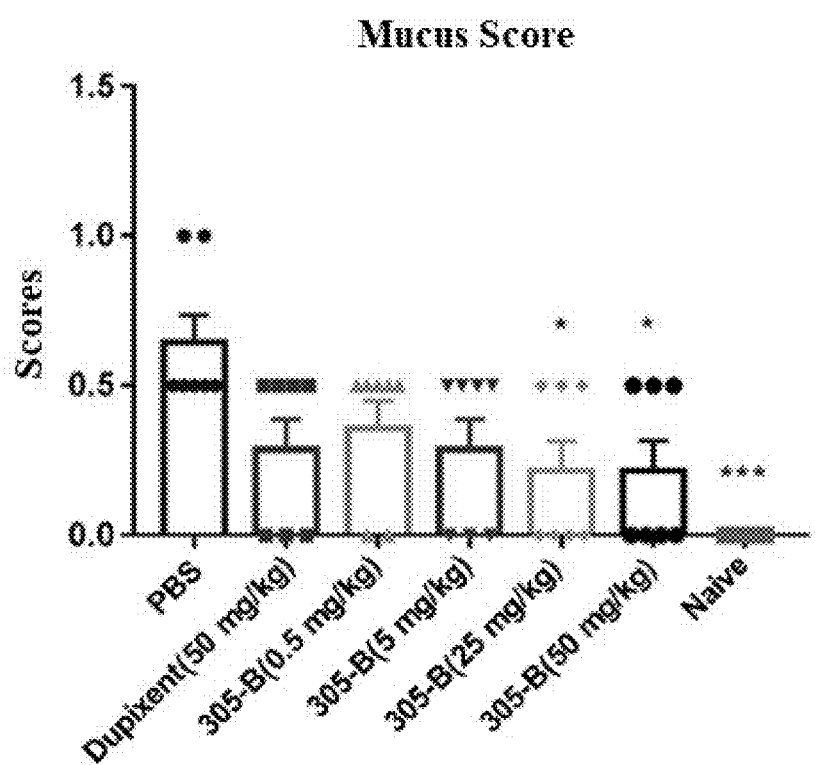
FIG. 9 shows mucus secretion in lung tissues of animals in each model group.

Compared with the PBS model group, the serum IgE of the test sample 305-B (0.5 mg/kg) group decreased significantly ($p<0.05$), and the serum IgE of the positive control Dupilumab (50 mg/kg) group and the test sample 305-B (5 mg/kg), (25 mg/kg) and (50 mg/kg) groups decreased significantly ($p<0.0001$), as shown in FIG. 6; except the 305-B (0.5 mg/kg) group, the percentage of eosinophils in white blood cells (Eos/WBC %) in each treated group decreased significantly ($p<0.0001$), as shown in FIG. 7; except for the 305-B (0.5 mg/kg) group, there was no obvious eosinophil infiltration in the lung tissues of each treated group, and eosinophil scores decreased significantly ($p<0.05$), as shown in FIG. 8; and mucus formation in the lungs was significantly improved ($p<0.05$) in the 305-B (25 mg/kg) and (50 mg/kg) groups, as shown in FIG. 9. For the above indicators, there was no significant difference between 305-B and Dupilumab at the same dose (50 mg/kg).

In conclusion, in asthma-like lung inflammation mainly characterized by Th2 immune responses, two therapeutic doses (25 mg/kg or 50 mg/kg) of 305-B could significantly reduce the level of IgE in serum and Eos/WBC % in an alveolar lavage fluid, reduce the degree of pulmonary eosinophil infiltration and reduce mucus secretion. This fully demonstrated that 305-B can antagonize the occurrence of downstream Th2 responses by inhibiting IL-4 and IL-13 signaling pathways, has a strong asthma inhibition function, and takes effect quickly. This inhibitory effect was dose-dependent. In terms of evaluation indicators, there was no significant difference between 305-B and Dupilumab at the same dose.

CONCLUSION

In affinity determination and analysis of various functional activities in vitro, the antibody according to the present invention shows consistent biological activities stronger than those of the control antibody Dupilumab. Results of pharmacodynamic studies in vivo show there is no significant difference between the antibody according to the present invention and the control antibody Dupilumab.

It can be understood that although this application is described in some form, this application is not limited to what is shown and described in the specification. It would be obvious to those skilled in the biology field that various changes can be made to the examples and/or a feature or parameter without departing from the scope of this application. These changes are within the scope set forth by this application.

SEQUENCE LISTING

```
Sequence total quantity: 207
SEQ ID NO: 1            moltype = DNA  length = 366
FEATURE                 Location/Qualifiers
source                  1..366
                        mol_type = other DNA
                        organism = Mus musculus
SEQUENCE: 1
gaagtgcagc tggtggaaag cggcggcggc ctggtgaaac cgggcggcag cctgaaactg   60
agctgcgcgg cgagcggctt tacctttagc gattatggca tgcattgggt gcgccaggcg  120
ccggaaaaag gcctggaatg ggtggcgtat attaacagcg gcagcagcaa aatttatcat  180
gcggataccg tgaaaggccg ctttaccatt agccgcgata acgcgaaaaa caccctgttt  240
ctgcagatga ccagcctgcg cagcgaagat accgcgatgt attattgcgc gcgctttccg  300
accgtggtgg cggcgcgcta tccgatggat tattgggcc  agggcaccag cgtgaccgtg  360
agcagc                                                             366

SEQ ID NO: 2            moltype = AA  length = 122
FEATURE                 Location/Qualifiers
source                  1..122
                        mol_type = protein
                        organism = Mus musculus
SEQUENCE: 2
EVQLVESGGG LVKPGGSLKL SCAASGFTFS DYGMHWVRQA PEKGLEWVAY INSGSSKIYH   60
ADTVKGRFTI SRDNAKNTLF LQMTSLRSED TAMYYCARFP TVVAARYPMD YWGQGTSVTV  120
SS                                                                 122

SEQ ID NO: 3            moltype = DNA  length = 321
FEATURE                 Location/Qualifiers
source                  1..321
```

```
                        mol_type = other DNA
                        organism = Mus musculus
SEQUENCE: 3
gatattcaga tgacccagac cccgagcagc ctgagcgcga gcctgggcga tcgcgtgacc   60
attagctgcc gcgcgagcca ggatattagc aactatctga actggtatca gcagaaaccg  120
gatggcaccg tgaaactgct gatttatttt accagccgcc tgcatagcgg cgtgccgagc  180
cgctttagcg gcggcggcag cggcaccgat tatagcctga ccattagcaa cctggaacag  240
gaagatattg cgacctattt ttgccagcag ggcaacaccc tgccgtatac ctttggcggc  300
ggcaccaaac tggaaattaa a                                            321

SEQ ID NO: 4           moltype = AA  length = 107
FEATURE                Location/Qualifiers
source                 1..107
                       mol_type = protein
                       organism = Mus musculus
SEQUENCE: 4
DIQMTQTPSS LSASLGDRVT ISCRASQDIS NYLNWYQQKP DGTVKLLIYF TSRLHSGVPS   60
RFSGGGSGTD YSLTISNLEQ EDIATYFCQQ GNTLPYTFGG GTKLEIK                107

SEQ ID NO: 5           moltype = DNA  length = 354
FEATURE                Location/Qualifiers
source                 1..354
                       mol_type = other DNA
                       organism = Mus musculus
SEQUENCE: 5
gaagtgcagc tggtggaaag cggcggcggc ctggtgaaac cgggcggcag cctgaaactg   60
agctgcgcgg cgagcggctt tacctttagc gattatggca ttcattgggt gcgccaggcg  120
ccggataaag gcctggaatg ggtggcgtat attcgcagcg atagcagcat tattcattat  180
gcggataccg tgaaaggccg ctttaccatt agccgcgata cgcgaaaaa caccctgttt   240
ctgcagatga ccagcctgcg cagcgaagat accgcgatgt attattgcac ccgcggccgc  300
gatcgcggct attttgatta ttggggccag ggcaccaccc tgaccgtgag cagc        354

SEQ ID NO: 6           moltype = AA  length = 118
FEATURE                Location/Qualifiers
source                 1..118
                       mol_type = protein
                       organism = Mus musculus
SEQUENCE: 6
EVQLVESGGG LVKPGGSLKL SCAASGFTFS DYGIHWVRQA PDKGLEWVAY IRSDSSIIHY   60
ADTVKGRFTI SRDNAKNTLF LQMTSLRSED TAMYYCTRGR DRGYFDYWGQ GTTLTVSS    118

SEQ ID NO: 7           moltype = DNA  length = 318
FEATURE                Location/Qualifiers
source                 1..318
                       mol_type = other DNA
                       organism = Mus musculus
SEQUENCE: 7
cagattgtgc tgacccagag cccggcgctg atgagcgcga gcccgggcga aaaagtgacc   60
atgacctgca gcgcgagcag cagcgtgagc tatatgtatt ggtatcagca gaaaccgcgc  120
agcagcccga aaccgtggat ttatctgacc agcaacctgg cgagcggcgt gccggcgcgc  180
tttagcggca gcggcagcgg caccagctat agcctgacca ttagcagcat ggaagcgaa   240
gatgcggcga cctattattg ccagcagtgg accagcattc cgtttacctt tggcagcggc  300
accaaactgg aaattaaa                                                318

SEQ ID NO: 8           moltype = AA  length = 106
FEATURE                Location/Qualifiers
source                 1..106
                       mol_type = protein
                       organism = Mus musculus
SEQUENCE: 8
QIVLTQSPAL MSASPGEKVT MTCSASSSVS YMYWYQQKPR SSPKPWIYLT SNLASGVPAR   60
FSGSGSGTSY SLTISSMEAE DAATYYCQQW TSIPFTFGSG TKLEIK                 106

SEQ ID NO: 9           moltype = DNA  length = 366
FEATURE                Location/Qualifiers
source                 1..366
                       mol_type = other DNA
                       organism = Mus musculus
SEQUENCE: 9
gaagtgcagc tggtggaaag cggcggcggc ctggtgaaac cgggcggcag cctgaaactg   60
agctgcgcgg cgagcggctt tacctttagc gattatggca tgcattgggt gcgccaggcg  120
ccggaaaaag gcctggaatg ggtggcgtat attagcagcg gcagcaccac catttattat  180
gcggataccg tgaaaggccg ctttaccatt agccgcgata cggcaaaaa caccctgttt   240
ctgcagatga ccagcctgcg cagcgaagat accgcgatgt attattgcgc gcgcattagc  300
accgtggtgg cgaaacgcta tgcgatggat tattgggc agggcaccag cgtgaccgtg  360
agcagc                                                             366

SEQ ID NO: 10          moltype = AA  length = 122
FEATURE                Location/Qualifiers
```

```
                                source          1..122
                                                mol_type = protein
                                                organism = Mus musculus
SEQUENCE: 10
EVQLVESGGG LVKPGGSLKL SCAASGFTFS DYGMHWVRQA PEKGLEWVAY ISSGSTTIYY        60
ADTVKGRFTI SRDNGKNTLF LQMTSLRSED TAMYYCARIS TVVAKRYAMD YWGQGTSVTV       120
SS                                                                     122

SEQ ID NO: 11                   moltype = DNA  length = 321
FEATURE                         Location/Qualifiers
source                          1..321
                                mol_type = other DNA
                                organism = Mus musculus
SEQUENCE: 11
gatattcaga tgacccagac cgcgagcagc ctgagcgcga gcctgggcga tcgcgtgacc        60
attagctgcc gcgcgagcca ggatattagc aactatctga actggtatca gcagaaaccg       120
gatggcaccg tgaaactgct gatttattat accagccgcc tgcatagcgg cgtgccgagc       180
cgctttagcg gcagcggcag cggcaccgat tatagcctga ccattagcaa cctggaacag       240
gaagatattg cgacctattt ttgccagcag attaacgcgc tgccgctgac ctttggcgcg       300
ggcaccaaac tggaactgaa a                                                 321

SEQ ID NO: 12                   moltype = AA   length = 107
FEATURE                         Location/Qualifiers
source                          1..107
                                mol_type = protein
                                organism = Mus musculus
SEQUENCE: 12
DIQMTQTASS LSASLGDRVT ISCRASQDIS NYLNWYQQKP DGTVKLLIYY TSRLHSGVPS        60
RFSGSGSGTD YSLTISNLEQ EDIATYFCQQ INALPLTFGA GTKLELK                    107

SEQ ID NO: 13                   moltype = DNA  length = 366
FEATURE                         Location/Qualifiers
source                          1..366
                                mol_type = other DNA
                                organism = Mus musculus
SEQUENCE: 13
gaagtgcagc tggtggaaag cggcggcggc ctggtgaaac cggcggcag cctgaaactg         60
agctgcgcgc cgagcggctt tacctttagc gattatggca tgcattgggt gcgccaggcg       120
ccggaaaaag gcctgaatg ggtggcgtat attagcagcg gcagcactt attatt             180
gcggataccg tgaaaggccg ctttaccatt agccgcgata cgcgaaaaa cacccctgttt       240
ctgcagatga ccagcctgcg cagcgaagat accgcgatgt attattgcgc gcgcattagc       300
accgtggtgg cgaaacgcta tgcgatggat tattgggcc agggcaccag cgtgaccgtg       360
agcagc                                                                 366

SEQ ID NO: 14                   moltype = AA   length = 122
FEATURE                         Location/Qualifiers
source                          1..122
                                mol_type = protein
                                organism = Mus musculus
SEQUENCE: 14
EVQLVESGGG LVKPGGSLKL SCAASGFTFS DYGMHWVRQA PEKGLEWVAY ISSGSSTIYY        60
ADTVKGRFTI SRDNAKNTLF LQMTSLRSED TAMYYCARIS TVVAKRYAMD YWGQGTSVTV       120
SS                                                                     122

SEQ ID NO: 15                   moltype = DNA  length = 321
FEATURE                         Location/Qualifiers
source                          1..321
                                mol_type = other DNA
                                organism = Mus musculus
SEQUENCE: 15
gatattcaga tgacccagac cgcgagcagc ctgagcgcga gcctgggcga tcgcgtgacc        60
attagctgcc gcgcgagcca ggatattagc aactatctga actggtatca gcagaaaccg       120
gatggcaccg tgaaactgct gatttattat accagccgcc tgcatagcgg cgtgccgagc       180
cgctttagcg gcagcggcag cggcaccgat tatagcctga ccattagcaa cctggaacag       240
gaagatattg cgacctattt ttgccaggaa gtgaacatgc tgccgctgac ctttggcgcg       300
ggcaccaaac tggaactgaa a                                                 321

SEQ ID NO: 16                   moltype = AA   length = 107
FEATURE                         Location/Qualifiers
source                          1..107
                                mol_type = protein
                                organism = Mus musculus
SEQUENCE: 16
DIQMTQTASS LSASLGDRVT ISCRASQDIS NYLNWYQQKP DGTVKLLIYY TSRLHSGVPS        60
RFSGSGSGTD YSLTISNLEQ EDIATYFCQE VNMLPLTFGA GTKLELK                    107

SEQ ID NO: 17                   moltype = DNA  length = 366
FEATURE                         Location/Qualifiers
source                          1..366
```

```
                        mol_type = other DNA
                        organism = Mus musculus
SEQUENCE: 17
gaagtgcagc tggtggaaag cggcggcggc ctggtgaaac cgggcggcag cctgaaactg   60
agctgcgcgg cgagcggctt tacctttagc gattatggca tgcattgggt gcgccaggcg  120
ccggaaaaag gcctggaatg ggtggcgtat attagcagcg gcagcaccac catttattat  180
gcggatacc  tgaaaggccg ctttaccatt agccgcgata acggcaaaaa cacccctgttt  240
ctgcagatga ccagcctgcg cagcgaagat accgcgatgt attattgcgc gcgcattagc  300
accgtggtgg cgaaacgcta tgcgatggat tattggggcc agggcaccag cgtgaccgtg  360
agcagc                                                              366

SEQ ID NO: 18            moltype = AA   length = 122
FEATURE                  Location/Qualifiers
source                   1..122
                         mol_type = protein
                         organism = Mus musculus
SEQUENCE: 18
EVQLVESGGG LVKPGGSLKL SCAASGFTFS DYGMHWVRQA PEKGLEWVAY ISSGSTTIYY   60
ADTVKGRFTI SRDNGKNTLF LQMTSLRSED TAMYYCARIS TVVAKRYAMD YWGQGTSVTV  120
SS                                                                 122

SEQ ID NO: 19            moltype = DNA   length = 321
FEATURE                  Location/Qualifiers
source                   1..321
                         mol_type = other DNA
                         organism = Mus musculus
SEQUENCE: 19
gatattcaga tgacccagac cgcgagcagc ctgagcgcga gcctgggcga tcgcgtgacc   60
attagctgcc gcgcgagcca ggatattagc aactatctga actggtatca gcagaaaccg  120
gatggcaccg tgaaactgct gatttattat accagcgcc  tgcatagcgg cgtgccgagc  180
cgctttagcg gcagcggcag cggcaccgat tatagcctga ccattagcaa cctgaacag   240
gaagatattg cgacctattt ttgccagcag attaacgcgc tgccgctgac ctttggcgcg  300
ggcaccaaac tggaactgaa a                                            321

SEQ ID NO: 20            moltype = AA   length = 107
FEATURE                  Location/Qualifiers
source                   1..107
                         mol_type = protein
                         organism = Mus musculus
SEQUENCE: 20
DIQMTQTASS LSASLGDRVT ISCRASQDIS NYLNWYQQKP DGTVKLLIYY TSRLHSGVPS   60
RFSGSGSGTD YSLTISNLEQ EDIATYFCQQ INALPLTFGA GTKLELK                107

SEQ ID NO: 21            moltype = DNA   length = 360
FEATURE                  Location/Qualifiers
source                   1..360
                         mol_type = other DNA
                         organism = Mus musculus
SEQUENCE: 21
gaagtgcagc tgcagcagag cggcccggaa ctggtgaaac cgggcgcgag cgtgaaaatt   60
ccgtgcaaag cgagcggcta tacctttacc gattataaca tggattgggt gaaacagagc  120
catggcaaaa gcctggaatg gattggcgat attaacccga caacggcaa  cattctgttt  180
aaccagaaat ttaaaggcaa agcgaccctg accgtggata aaagcagcag caccgcgtat  240
gtggaactgc gcagcctgac cagcgaagat accgcggtgt attattgcgg ccgcggcggc  300
ctgcgccgcc gcggctttat ggattattgg ggccagggca ccagcgtgac cgtgagcagc  360

SEQ ID NO: 22            moltype = AA   length = 120
FEATURE                  Location/Qualifiers
source                   1..120
                         mol_type = protein
                         organism = Mus musculus
SEQUENCE: 22
EVQLQQSGPE LVKPGASVKI PCKASGYTFT DYNMDWVKQS HGKSLEWIGD INPNNGNILF   60
NQKFKGKATL TVDKSSSTAY VELRSLTSED TAVYYCGRGG LRRRGFMDYW GQGTSVTVSS  120

SEQ ID NO: 23            moltype = DNA   length = 318
FEATURE                  Location/Qualifiers
source                   1..318
                         mol_type = other DNA
                         organism = Mus musculus
SEQUENCE: 23
cagattgtgc tgagccagag cccggcgatt ctgagcgcga gcccgggcga aaaagtgacc   60
atgacctgcc gcgcgagcag cagcgtgagc tatatgcatt ggtatcagca gaaacccggc  120
agcagcccga aacctggat  ttatgcgcg  agcaacctgg cgagcggcgt gccggcgcgc  180
tttagcggca gcgcagcgg  accagctat  agcctgacca ttagccgcgt ggaagcggaa  240
gatgcggcga cctattattg ccagcagtgg agcagcaacc cgccgacctt tggcggcggc  300
accaaactgg aaattaaa                                                318

SEQ ID NO: 24            moltype = AA   length = 106
```

| FEATURE | Location/Qualifiers |
|---|---|
| source | 1..106<br>mol_type = protein<br>organism = Mus musculus |

SEQUENCE: 24
```
QIVLSQSPAI LSASPGEKVT MTCRASSSVS YMHWYQQKPG SSPKPWIYAA SNLASGVPAR   60
FSGSGSGTSY SLTISRVEAE DAATYYCQQW SSNPPTFGGG TKLEIK                106
```

| SEQ ID NO: 25 | moltype = DNA length = 360 |
|---|---|
| FEATURE | Location/Qualifiers |
| source | 1..360<br>mol_type = other DNA<br>organism = Mus musculus |

SEQUENCE: 25
```
gatgtgcagc tgcagcagag cggcccggaa ctgctgaaaa cgggcgcgag cgtgaaaatt    60
ccgtgccagg cgagcggcta tacctttacc gattataaca tggattgggt gaaacagagc   120
catggcaaaa acctggaatg gattggcaac attaacccga caacggcgg caccttttat   180
aaccagaaat ttaaaggcaa agcgaccctg accgtggata accgcgtat                240
atggaactgc gcagcctgac cagcgaagat accgcggtgt attattgcgg ccgcggcggc   300
ctgcgccgcc gcggctttat ggattattgg ggccagggca ccagcgtgac cgtgagcagc   360
```

| SEQ ID NO: 26 | moltype = AA length = 120 |
|---|---|
| FEATURE | Location/Qualifiers |
| source | 1..120<br>mol_type = protein<br>organism = Mus musculus |

SEQUENCE: 26
```
DVQLQQSGPE LLKPGASVKI PCQASGYTFT DYNMDWVKQS HGKNLEWIGN INPNNGGTFY    60
NQKFKGKATL TVDKSSSTAY MELRSLTSED TAVYYCGRGG LRRRGFMDYW GQGTSVTVSS   120
```

| SEQ ID NO: 27 | moltype = DNA length = 318 |
|---|---|
| FEATURE | Location/Qualifiers |
| source | 1..318<br>mol_type = other DNA<br>organism = Mus musculus |

SEQUENCE: 27
```
cagattgtgc tgagccagag cccggcgatt ctgagcgcga gcccgggcga aaaagtgacc    60
atgacctgcc gcgcgagcag cagcgtgatt tatattcatt ggtatcagca gaaaccgggc   120
agcagcccga aacgtggat ttatgcggcg agcaacctgg cgagcggcgt gccggtgcgc   180
tttagcggca gcggcagcgg caccagctat agcctgacca ttagccgcgt ggaagcggaa   240
gatgcggcga cctattattg ccagcagtgg agcgtgaacc cgccgacctt tggcggcggc   300
accaaactgg aaattaaa                                                 318
```

| SEQ ID NO: 28 | moltype = AA length = 106 |
|---|---|
| FEATURE | Location/Qualifiers |
| source | 1..106<br>mol_type = protein<br>organism = Mus musculus |

SEQUENCE: 28
```
QIVLSQSPAI LSASPGEKVT MTCRASSSVI YIHWYQQKPG SSPKPWIYAA SNLASGVPVR    60
FSGSGSGTSY SLTISRVEAE DAATYYCQQW SVNPPTFGGG TKLEIK                 106
```

| SEQ ID NO: 29 | moltype = DNA length = 360 |
|---|---|
| FEATURE | Location/Qualifiers |
| source | 1..360<br>mol_type = other DNA<br>organism = Mus musculus |

SEQUENCE: 29
```
gaagtgcagc tgcagcagag cggcccggaa ctggtgaaaa cgggcgcgag cgtgaaaatt    60
ccgtgcaaag cgagcggcta tacctttacc gattataaca tggattgggt gaaacagagc   120
catggcaaaa gcctggaatg gattggcgat attaacccga caacggcaa cattctgttt   180
aaccagaaat ttaaaggcaa agcgaccctg accgtggata aaagcagcag caccgcgtat   240
gtggaactgc gcagcctgac cagcgaagat accgcggtgt attattgcgg ccgcggcggc   300
ctgcgccgcc gcggctttat ggattattgg ggccagggca ccagcgtgac cgtgagcagc   360
```

| SEQ ID NO: 30 | moltype = AA length = 120 |
|---|---|
| FEATURE | Location/Qualifiers |
| source | 1..120<br>mol_type = protein<br>organism = Mus musculus |

SEQUENCE: 30
```
EVQLQQSGPE LVKPGASVKI PCKASGYTFT DYNMDWVKQS HGKSLEWIGD INPNNGNILF    60
NQKFKGKATL TVDKSSSTAY VELRSLTSED TAVYYCGRGG LRRRGFMDYW GQGTSVTVSS   120
```

| SEQ ID NO: 31 | moltype = DNA length = 318 |
|---|---|
| FEATURE | Location/Qualifiers |
| source | 1..318<br>mol_type = other DNA<br>organism = Mus musculus |

```
SEQUENCE: 31
cagattgtgc tgagccagag cccggcgatt ctgagcgcga gcccgggcga aaaagtgacc    60
atgacctgcc gcgcgagcag cagcgtgagc tatatgcatt ggtatcagca gaaaccgggc   120
agcagcccga aaccgtggat ttatgcggcg agcaacctgg cgagcggcgt gccggcgcgc   180
tttagcggca gcggcagcgg caccagctat agcctgacca ttagccgcgt ggaagcggaa   240
gatgcggcga cctattattg ccagcagtgg agcagcaacc cgccgacctt tggcggcggc   300
accaaactgg aaattaaa                                                 318

SEQ ID NO: 32        moltype = AA   length = 106
FEATURE              Location/Qualifiers
source               1..106
                     mol_type = protein
                     organism = Mus musculus
SEQUENCE: 32
QIVLSQSPAI LSASPGEKVT MTCRASSSVS YMHWYQQKPG SSPKPWIYAA SNLASGVPAR    60
FSGSGSGTSY SLTISRVEAE DAATYYCQQW SSNPPTFGGG TKLEIK                  106

SEQ ID NO: 33        moltype = DNA   length = 360
FEATURE              Location/Qualifiers
source               1..360
                     mol_type = other DNA
                     organism = Mus musculus
SEQUENCE: 33
gaagtgcagc tgcagcagag cggcccggaa ctggtgaaaa cgggcgcgag cgtgaaaatt    60
agctgcaaag cgagcggcta cctttacc gattataaca tggattgggt gaaacagagc    120
catggcaaaa gcctggaatg gattggcacc accaacccga caacggcaa caccctgtat   180
aaccagaaat ttaaaggcaa agcgaccctg accgtggata aaagcagcag caccgcgtat   240
atggaactgc gcagcctgac cagcgaagat accgcggtgt attattgcgc gcgcggcggc   300
ctgcgccgcc gcggctttgt ggattattgg ggccagggca ccagcgtgac cgtgagcagc   360

SEQ ID NO: 34        moltype = AA   length = 120
FEATURE              Location/Qualifiers
source               1..120
                     mol_type = protein
                     organism = Mus musculus
SEQUENCE: 34
EVQLQQSGPE LVKPGASVKI SCKASGYTFT DYNMDWVKQS HGKSLEWIGT TNPNNGGTLY    60
NQKFKGKATL TVDKSSSTAY MELRSLTSED TAVYYCARGG LRRRGFVDYW GQGTSVTVSS   120

SEQ ID NO: 35        moltype = DNA   length = 318
FEATURE              Location/Qualifiers
source               1..318
                     mol_type = other DNA
                     organism = Mus musculus
SEQUENCE: 35
cagattgtgc tgagccagag cccggcgatt ctgagcgcga gcccgggcga aaaagtgacc    60
atgacctgcc gcgcgagcag cagcgtgaac tatctgcatt ggtatcagca gaaaccgggc   120
agcagcccga aaccgtggat ttatgcgacc agcaacctgg cgagcggcgt gccggcgcgc   180
tttagcggca gcggcagcgg caccagctat agcctgacca ttagccgcgt ggaagcggaa   240
gatgcggcga cctattattg ccagcagtgg agcagcaacc cgccgacctt tggcggcggc   300
accaaactgg aaattaaa                                                 318

SEQ ID NO: 36        moltype = AA   length = 106
FEATURE              Location/Qualifiers
source               1..106
                     mol_type = protein
                     organism = Mus musculus
SEQUENCE: 36
QIVLSQSPAI LSASPGEKVT MTCRASSSVN YLHWYQQKPG SSPKPWIYAT SNLASGVPAR    60
FSGSGSGTSY SLTISRVEAE DAATYYCQQW SSNPPTFGGG TKLEIK                  106

SEQ ID NO: 37        moltype = DNA   length = 360
FEATURE              Location/Qualifiers
source               1..360
                     mol_type = other DNA
                     organism = Mus musculus
SEQUENCE: 37
gaagtgcagc tgcagcagag cggcccggaa ctggtgaaaa cgggcgcgag cgtgaaaatt    60
cgctgcaaag cgagcggcta cctttacc gattataaca tggattgggt gaaacagagc    120
catggcaaaa gcctggaatg gattggcgat attaacccga caacggcaa cattctgttt   180
aaccagaaat ttaaaggcaa agcgaccctg accgtggata aaagcagcag caccgcgtat   240
gtggaactgc gcagcctgac cagcgaagat accgcggtgt attattgcgg ccgcggcggc   300
ctgcgccgcc gcggctttat ggattattgg ggccagggca ccagcgtgac cgtgagcagc   360

SEQ ID NO: 38        moltype = AA   length = 120
FEATURE              Location/Qualifiers
source               1..120
                     mol_type = protein
                     organism = Mus musculus
```

```
SEQUENCE: 38
EVQLQQSGPE LVKPGASVKI PCKASGYTFT DYNMDWVKQS HGKSLEWIGD INPNNGNILF     60
NQKFKGKATL TVDKSSSTAY VELRSLTSED TAVYYCGRGG LRRRGFMDYW GQGTSVTVSS    120

SEQ ID NO: 39              moltype = DNA   length = 318
FEATURE                    Location/Qualifiers
source                     1..318
                           mol_type = other DNA
                           organism = Mus musculus
SEQUENCE: 39
cagattgtgc tgagccagag cccggcgatt ctgagcgcga gcccgggcga aaaagtgacc     60
atgacctgcc gcgcgagcag cagcgtgagc tatatgcatt ggtatcagca gaaaccgggc    120
agcagcccga aaccgtggat ttatgcggcg agcaacctgg cgagcggcgt gccggcgcgc    180
tttagcggca gcggcagcgg caccagctat agcctgacca ttagccgcgt ggaagcggaa    240
gatgcggcga cctattattg ccagcagtgg agcagcaacc cgccgacctt tggcggcggc    300
accaaactgg aaattaaa                                                  318

SEQ ID NO: 40              moltype = AA   length = 106
FEATURE                    Location/Qualifiers
source                     1..106
                           mol_type = protein
                           organism = Mus musculus
SEQUENCE: 40
QIVLSQSPAI LSASPGEKVT MTCRASSSVS YMHWYQQKPG SSPKPWIYAA SNLASGVPAR     60
FSGSGSGTSY SLTISRVEAE DAATYYCQQW SSNPPTFGGG TKLEIK                   106

SEQ ID NO: 41              moltype = DNA   length = 360
FEATURE                    Location/Qualifiers
source                     1..360
                           mol_type = other DNA
                           organism = Mus musculus
SEQUENCE: 41
gatgtgcagc tgcagcagag cggcccggaa ctgctgaaaa cgggcgcgag cgtgaaaatt     60
ccgtgccagg cgagcggcta tacctttacc gattataaca tggattgggt gaaacagagc    120
catggcaaaa acctggaatg gattggcaac attaacccga caacggcgta caccttttat    180
aaccagaaat ttaaaggcaa agcgaccctg accgtggata aaagcagcag caccgcgtat    240
atggaactgc gcagcctgac cagcgaagat accgcggtgt attattgcgg ccgcggcggc    300
ctgcgccgcc gcggctttat ggattattgg ggccagggca ccagcgtgac cgtgagcagc    360

SEQ ID NO: 42              moltype = AA   length = 120
FEATURE                    Location/Qualifiers
source                     1..120
                           mol_type = protein
                           organism = Mus musculus
SEQUENCE: 42
DVQLQQSGPE LLKPGASVKI PCQASGYTFT DYNMDWVKQS HGKNLEWIGN INPNNGGTFY     60
NQKFKGKATL TVDKSSSTAY MELRSLTSED TAVYYCGRGG LRRRGFMDYW GQGTSVTVSS    120

SEQ ID NO: 43              moltype = DNA   length = 318
FEATURE                    Location/Qualifiers
source                     1..318
                           mol_type = other DNA
                           organism = Mus musculus
SEQUENCE: 43
cagattgtgc tgagccagag cccggcgatt ctgagcgcga gcccgggcga aaaagtgacc     60
atgacctgcc gcgcgagcag cagcgtgatt tatattcatt ggtatcagca gaaaccgggc    120
agcagcccga aaccgtggat ttatgcggcg agcaacctgg cgagcggcgt gccggcgcgc    180
tttagcggca gcggcagcgg caccagctat agcctgacca ttagccgcgt ggaagcggaa    240
gatgcggcga cctattattg ccagcagtgg agcgtgaacc cgccgacctt tggcggcggc    300
accaaactgg aaattaaa                                                  318

SEQ ID NO: 44              moltype = AA   length = 106
FEATURE                    Location/Qualifiers
source                     1..106
                           mol_type = protein
                           organism = Mus musculus
SEQUENCE: 44
QIVLSQSPAI LSASPGEKVT MTCRASSSVI YIHWYQQKPG SSPKPWIYAA SNLASGVPAR     60
FSGSGSGTSY SLTISRVEAE DAATYYCQQW SVNPPTFGGG TKLEIK                   106

SEQ ID NO: 45              moltype = DNA   length = 360
FEATURE                    Location/Qualifiers
source                     1..360
                           mol_type = other DNA
                           organism = Mus musculus
SEQUENCE: 45
gaagtgcagc tgcagcagag cggcccggaa ctggtgaaaa cgggcgcgag cgtgaaaatt     60
ccgtgcaaag cgagcggcta tacctttacc gattataaca tggattgggt gaaacagagc    120
cgcggcaaaa gcctggaatg gattggcacc attaacccga caacggcgta taccatgtat    180
```

```
aaccagaaat ttaaagataa agcgaccctg accgtggata aaagcagcac caccgcgtat    240
atggaactgc gcagcctgac cagcgaagat accgcggtgt attattgcgg ccgcggcggc    300
ctgcgccgcc gcggctttat ggattattgg ggccgcggca ccagcgtgac cgtgagcagc    360

SEQ ID NO: 46          moltype = AA   length = 120
FEATURE                Location/Qualifiers
source                 1..120
                       mol_type = protein
                       organism = Mus musculus
SEQUENCE: 46
EVQLQQSGPE LVKPGASVKI PCKASGYTFT DYNMDWVKQS RGKSLEWIGT INPNNGDTMY    60
NQKFKDKATL TVDKSSTTAY MELRSLTSED TAVYYCGRGG LRRRGFMDYW GRGTSVTVSS   120

SEQ ID NO: 47          moltype = DNA   length = 318
FEATURE                Location/Qualifiers
source                 1..318
                       mol_type = other DNA
                       organism = Mus musculus
SEQUENCE: 47
cagattgtgc tgagccagag cccggcgatt ctgagcgcga gcccgggcga aaaagtgacc    60
atgacctgcc gcgcgagcag cagcgtgatt tatattcatt ggtatcagca gaaaccgggc   120
agcagcccga aaccgtggat ttatgcgatt agcaacctgg cgagcggcgt gccggcgcgc   180
tttagcggca gcggcagcgg caccagctat tttctgacca ttagccgcgt ggaagtggaa   240
gatgcggcga cctattattg ccagcagtgg agcgtgaacc cgccgacctt tggcggcggc   300
accaaactgg aaattaaa                                                  318

SEQ ID NO: 48          moltype = AA   length = 106
FEATURE                Location/Qualifiers
source                 1..106
                       mol_type = protein
                       organism = Mus musculus
SEQUENCE: 48
QIVLSQSPAI LSASPGEKVT MTCRASSSVI YIHWYQQKPG SSPKPWIYAI SNLASGVPAR    60
FSGSGSGTSY FLTISRVEVE DAATYYCQQW SVNPPTFGGG TKLEIK                  106

SEQ ID NO: 49          moltype = DNA   length = 360
FEATURE                Location/Qualifiers
source                 1..360
                       mol_type = other DNA
                       organism = Mus musculus
SEQUENCE: 49
gatgtgcagc tgcagcagag cggccgcgaa ctgctgaaac gcggcgcgag cgtgaaaatt    60
ccgtgccagg cgagcggcta cccttttacc gattataaca tggattgggt gaaacagagc   120
catggcaaaa acctgaatg gattggcaac attaacccga caacggcgg cacctttttat   180
aaccagaaat ttaaaggcaa agcgaccctg accgtggata aaagcagcag caccgcgtat   240
atggaactgc gcagcctgac cagcgaagat accgcggtgt attattgcgg ccgcggcggc   300
ctgcgccgcc gcggctttat ggattattgg ggccagggca ccagcgtgac cgtgagcagc   360

SEQ ID NO: 50          moltype = AA   length = 120
FEATURE                Location/Qualifiers
source                 1..120
                       mol_type = protein
                       organism = Mus musculus
SEQUENCE: 50
DVQLQQSGRE LLKRGASVKI PCQASGYTFT DYNMDWVKQS HGKNLEWIGN INPNNGGTFY    60
NQKFKGKATL TVDKSSSTAY MELRSLTSED TAVYYCGRGG LRRRGFMDYW GQGTSVTVSS   120

SEQ ID NO: 51          moltype = DNA   length = 318
FEATURE                Location/Qualifiers
source                 1..318
                       mol_type = other DNA
                       organism = Mus musculus
SEQUENCE: 51
cagattgtgc tgagccagag cccggcgatt ctgagcgcga gcccgggcga aaaagtgacc    60
atgacctgcc gcgcgagcag cagcgtgatt tatattcatt ggtatcagca gaaaccgggc   120
agcagcccga aaccgtggat ttatgcggcg agcaacctgg cgagcggcgt gccggcgcgc   180
tttagcggca gcggcagcgg caccagctat agcctgacca ttagccgcgt ggaagcggaa   240
gatgcggcga cctattattg ccagcagtgg agcgtgaacc cgccgacctt tggcggcggc   300
accaaactgg aaattaaa                                                  318

SEQ ID NO: 52          moltype = AA   length = 106
FEATURE                Location/Qualifiers
source                 1..106
                       mol_type = protein
                       organism = Mus musculus
SEQUENCE: 52
QIVLSQSPAI LSASPGEKVT MTCRASSSVI YIHWYQQKPG SSPKPWIYAA SNLASGVPAR    60
FSGSGSGTSY SLTISRVEAE DAATYYCQQW SVNPPTFGGG TKLEIK                  106
```

-continued

```
SEQ ID NO: 53              moltype = DNA   length = 360
FEATURE                    Location/Qualifiers
source                     1..360
                           mol_type = other DNA
                           organism = Mus musculus
SEQUENCE: 53
gatgtgcagc tgcagcagag cggcccggaa ctgctgaaac cggcgcgag cgtgaaaatt    60
ccgtgccagg cgagcggcta taccttttacc gattataaca tggattgggt gaaacagagc  120
catggcaaaa acctgaatg gattggcacc attaacccga caacggcgg cacctttttat   180
aaccagaact ttaaaggcaa agcgaccctg accgtggata aaagcagcag caccgcgtgc   240
atggaactgc gcagcctgac cagcgatgat accgcggtgt attattgcgg ccgcggcggc   300
ctgcgccgcc gcggctttat ggattattgg ggccagggca ccagcgtgac cgtgagcagc   360

SEQ ID NO: 54              moltype = AA    length = 120
FEATURE                    Location/Qualifiers
source                     1..120
                           mol_type = protein
                           organism = Mus musculus
SEQUENCE: 54
DVQLQQSGPE LLKPGASVKI PCQASGYTFT DYNMDWVKQS HGKNLEWIGT INPNNGGTFY    60
NQNFKGKATL TVDKSSSTAC MELRSLTSDD TAVYYCGRGG LRRRGFMDYW GQGTSVTVSS   120

SEQ ID NO: 55              moltype = DNA    length = 318
FEATURE                    Location/Qualifiers
source                     1..318
                           mol_type = other DNA
                           organism = Mus musculus
SEQUENCE: 55
cagattgtgc tgagccagag cccggcgatt ctgagcgcga gcccgggcga aaaagtgacc    60
atgacctgcc gcgcgagcag cagcgtgatt tatattcatt ggtatcagca gaaaccgggc   120
agcagcccga aaccgtggat ttatgcggcg agcaacctgg cgagcggcgt gccggcgcgc   180
tttagcggca gcggcagcgg caccagctat agcctgacca ttagccgcgt ggaagcggaa   240
gatgcggcga cctattattg ccagcagtgg agcgtgaacc cgccgacctt tggcggcggc   300
accaaactgg aaattaaa                                                 318

SEQ ID NO: 56              moltype = AA    length = 106
FEATURE                    Location/Qualifiers
source                     1..106
                           mol_type = protein
                           organism = Mus musculus
SEQUENCE: 56
QIVLSQSPAI LSASPGEKVT MTCRASSSVI YIHWYQQKPG SSPKPWIYAA SNLASGVPAR    60
FSGSGSGTSY SLTISRVEAE DAATYYCQQW SVNPPTFGGG TKLEIK                  106

SEQ ID NO: 57              moltype = DNA    length = 360
FEATURE                    Location/Qualifiers
source                     1..360
                           mol_type = other DNA
                           organism = Mus musculus
SEQUENCE: 57
gatgtgcagc tgcagcagag cggcccggaa ctgctgaaac cggcgcgag cgtgaaaatt    60
ccgtgccagg cgagcggcta taccttttacc gattataaca tggattgggt gaaacagagc  120
catggcaaaa acctgaatg gattggcaac attaacccga caacggcgg cacctttttat   180
aaccagaaat ttaaaggcaa agcgaccctg accgtggata aaagcagcag caccgcgtat   240
atggaactgc gcagcctgac cagcgaagat accgcggtgt attattgcgg ccgcggcggc   300
ctgcgccgcc gcggctttct ggattattgg ggccagggca ccagcgtgac cgtgagcagc   360

SEQ ID NO: 58              moltype = AA    length = 120
FEATURE                    Location/Qualifiers
source                     1..120
                           mol_type = protein
                           organism = Mus musculus
SEQUENCE: 58
DVQLQQSGPE LLKPGASVKI PCQASGYTFT DYNMDWVKQS HGKNLEWIGN INPNNGGTFY    60
NQKFKGKATL TVDKSSSTAY MELRSLTSED TAVYYCGRGG LRRRGFLDYW GQGTSVTVSS   120

SEQ ID NO: 59              moltype = DNA    length = 318
FEATURE                    Location/Qualifiers
source                     1..318
                           mol_type = other DNA
                           organism = Mus musculus
SEQUENCE: 59
cagattgtgc tgagccagag cccggcgatt ctgagcgcga gcccgggcga aaaagtgacc    60
atgacctgcc gcgcgagcag cagcgtgatt tatattcatt ggtatcagca gaaaccgggc   120
agcagcccga aaccgtggat ttatgcggtg agcaacctgg cgagcggcgt gccggtgcgc   180
tttagcggca gcggcagcgg caccagctat agcctgacca ttagccgcgt ggaagcggaa   240
gatgcggcga cctattattg ccagcagtgg agcgtgaacc cgccgacctt tggcggcggc   300
accaaactgg aaattaaa                                                 318
```

-continued

```
SEQ ID NO: 60               moltype = AA   length = 106
FEATURE                     Location/Qualifiers
source                      1..106
                            mol_type = protein
                            organism = Mus musculus
SEQUENCE: 60
QIVLSQSPAI LSASPGEKVT MTCRASSSVI YIHWYQQKPG SSPKPWIYAV SNLASGVPVR    60
FSGSGSGTSY SLTISRVEAE DAATYYCQQW SVNPPTFGGG TKLEIK                  106

SEQ ID NO: 61               moltype = DNA   length = 360
FEATURE                     Location/Qualifiers
source                      1..360
                            mol_type = other DNA
                            organism = Mus musculus
SEQUENCE: 61
gatgtgcagc tgcagcagag cggcccggaa ctgctgaaaac cgggcgcgag cgtgaaaatt    60
ccgtgccagg cgagcggcta cctttacc gattataaca tggattgggt gaaacagagc    120
catggcaaaa acctggaatg gattggcaac attaacccga caacggcgg cacctttat    180
aaccagaaat ttaaaggcaa agcgaccctg accgtggata aaagcagcag caccgcgtat    240
atggaactgc gcagcctgac cagcgaagat accgcgtgt attattgcgg ccgcggcggc    300
ctgcgccgcc gcggctttat ggattattgg ggccagggca ccagcgtgac cgtgagcagc    360

SEQ ID NO: 62               moltype = AA   length = 120
FEATURE                     Location/Qualifiers
source                      1..120
                            mol_type = protein
                            organism = Mus musculus
SEQUENCE: 62
DVQLQQSGPE LLKPGASVKI PCQASGYTFT DYNMDWVKQS HGKNLEWIGN INPNNGGTFY    60
NQKFKGKATL TVDKSSSTAY MELRSLTSED TAVYYCGRGG LRRRGFMDYW GQGTSVTVSS   120

SEQ ID NO: 63               moltype = DNA   length = 318
FEATURE                     Location/Qualifiers
source                      1..318
                            mol_type = other DNA
                            organism = Mus musculus
SEQUENCE: 63
cagattgtgc tgagccagag cccggcgatt ctgagcgcga gcccgggcga aaaagtgacc    60
atgacctgcc gcgcgagcag cagcgtgatt tatattcatt ggtatcagca gaaaccgggc   120
agcagcccga aaccgtggat ttatgcggcg agcaacctgg cgagcggcgt gccggcgcgc   180
tttagcggca gcggcagcgg caccagctat agcctgacca ttagccgcgt ggaagcggaa    240
gatgcggcga cctattattg ccagcagtgg agcgtgaacc cgccgacctt tggcggcggc   300
accaaactgg aaattaaa                                                 318

SEQ ID NO: 64               moltype = AA   length = 106
FEATURE                     Location/Qualifiers
source                      1..106
                            mol_type = protein
                            organism = Mus musculus
SEQUENCE: 64
QIVLSQSPAI LSASPGEKVT MTCRASSSVI YIHWYQQKPG SSPKPWIYAA SNLASGVPAR    60
FSGSGSGTSY SLTISRVEAE DAATYYCQQW SVNPPTFGGG TKLEIK                  106

SEQ ID NO: 65               moltype = DNA   length = 360
FEATURE                     Location/Qualifiers
source                      1..360
                            mol_type = other DNA
                            organism = Mus musculus
SEQUENCE: 65
gaagtgcagc tgcagcagag cggcccggaa ctggtgaaaac cgggcgcgag cgtgaaaatt    60
ccgtgcaaag cgagcggcta cctttacc gattataacg tggattgggt gaaacagagc    120
catggccaga gcctggattg gattggcacc attaacccga caacggcgg cattctgagc    180
aaccagaaat ttaaaggcaa agcgaccctg accgtggata ccagcagcag caccgcgtat    240
atggaactgc gcagcctgac cagcgaagat accgcgtgt attattgcgg ccgcggcggc    300
ctgcgccgcc gcggctttat ggattattgg ggccagggca ccagcgtgac cgtgagcagc    360

SEQ ID NO: 66               moltype = AA   length = 120
FEATURE                     Location/Qualifiers
source                      1..120
                            mol_type = protein
                            organism = Mus musculus
SEQUENCE: 66
EVQLQQSGPE LVKPGASVKI PCKASGYTFT DYNVDWVKQS HGQSLDWIGT INPNNGGILS    60
NQKFKGKATL TVDTSSSTAY MELRSLTSED TAVYYCGRGG LRRRGFMDYW GQGTSVTVSS   120

SEQ ID NO: 67               moltype = DNA   length = 318
FEATURE                     Location/Qualifiers
source                      1..318
                            mol_type = other DNA
```

```
                         organism = Mus musculus
SEQUENCE: 67
cagattgtgc tgagccagag cccggcgatt ctgagcgcga gcccgggcga aaaagtgacc     60
atgacctgcc gcgcgagcag cagcgtgatt tatattcatt ggtattatca gaaagcgggc    120
agcagcccga aaccgtggat ttatgcggcg agcaacctgc cgagcggcgt gccgcaggcg    180
tttagcggca gcggcagcgg caccagctat agcctgacca ttagccgcgt ggaagcggaa    240
gatgcggcga cctattattg ccagcagtgg agcagcaacc cgccgacctt tggcggcggc    300
accaaactgg aaattaaa                                                  318

SEQ ID NO: 68           moltype = AA  length = 106
FEATURE                 Location/Qualifiers
source                  1..106
                        mol_type = protein
                        organism = Mus musculus
SEQUENCE: 68
QIVLSQSPAI LSASPGEKVT MTCRASSSVI YIHWYYQKAG SSPKPWIYAA SNLPSGVPAR     60
FSGSGSGTSY SLTISRVEAE DAATYYCQQW SSNPPTFGGG TKLEIK                   106

SEQ ID NO: 69           moltype = DNA  length = 366
FEATURE                 Location/Qualifiers
source                  1..366
                        mol_type = other DNA
                        organism = synthetic construct
SEQUENCE: 69
gaagtgcagc tggtggaaag cggcggcggc ctggtgcagc cgggcggcag cctgcgcctg     60
agctgcgcgg cgagcggctt tacctttagc gattatgcac tgcattgggt gcgccaggcg    120
ccgggcaaag cgctgaatg ggtggcgtat attaacagcg gcagcagcaa aatttatcat     180
gcggatacc tgaaaggccg ctttaccatt agccgcgata cgcgaaaaa cagcctgtat      240
ctgcagatga acagcctgcg cgcggaagat accgcggtgt attattgcg cgctttccg     300
accgtggtgg cggcgcgcta tccgatggat tattggggcc agggcaccct ggtgaccgtg    360
agcagc                                                               366

SEQ ID NO: 70           moltype = AA  length = 122
FEATURE                 Location/Qualifiers
source                  1..122
                        mol_type = protein
                        organism = synthetic construct
SEQUENCE: 70
EVQLVESGGG LVQPGGSLRL SCAASGFTFS DYGMHWVRQA PGKGLEWVAY INSGSSKIYH     60
ADTVKGRFTI SRDNAKNSLY LQMNSLRAED TAVYYCARFP TVVAARYPMD YWGQGTLVTV    120
SS                                                                   122

SEQ ID NO: 71           moltype = AA  length = 448
FEATURE                 Location/Qualifiers
source                  1..448
                        mol_type = protein
                        organism = synthetic construct
SEQUENCE: 71
EVQLVESGGG LVQPGGSLRL SCAASGFTFS DYGMHWVRQA PGKGLEWVAY INSGSSKIYH     60
ADTVKGRFTI SRDNAKNSLY LQMNSLRAED TAVYYCARFP TVVAARYPMD YWGQGTLVTV    120
SSASTKGPSV FPLAPCSRST SESTAALGCL VKDYFPEPVT VSWNSGALTS GVHTFPAVLQ    180
SSGLYSLSSV VTVPSSSLGT KTYTCNVDHK PSNTKVDKRV ESKYGPPCPP CPAPEFLGGP    240
SVFLFPPKPK DTLMISRTPE VTCVVVDVSQ EDPEVQFNWY VDGVEVHNAK TKPREEQFNS    300
TYRVVSVLTV LHQDWLNGKE YKCKVSNKGL PSSIEKTISK AKGQPREPQV YTLPPSQEEM    360
TKNQVSLTCL VKGFYPSDIA VEWESNGQPE NNYKTTPPVL DSDGSFFLYS RLTVDKSRWQ    420
EGNVFSCSVM HEALHNHYTQ KSLSLSLG                                       448

SEQ ID NO: 72           moltype = DNA  length = 321
FEATURE                 Location/Qualifiers
source                  1..321
                        mol_type = other DNA
                        organism = synthetic construct
SEQUENCE: 72
gatattcaga tgacccagag cccgagcagc ctgagcgcga gcgtgggcga tcgcgtgacc     60
attacctgcc gcgcgagcca ggatattagc aactatctga actggtatca gcagaaaccg    120
ggcaaagcgc cgaaactgct gatttatttt accagccgcc tgcatagcgg cgtgccgagc    180
cgctttagcg gcagcggcag cggcaccgat tatacc ctga ccattagcag cctgcagccg    240
gaagattttg cgacctatta ttgccagcag ggcaacaccc tgccgtatac ctttggccag    300
ggcaccaaac tggaaattaa a                                              321

SEQ ID NO: 73           moltype = AA  length = 107
FEATURE                 Location/Qualifiers
source                  1..107
                        mol_type = protein
                        organism = synthetic construct
SEQUENCE: 73
DIQMTQSPSS LSASVGDRVT ITCRASQDIS NYLNWYQQKP GKAPKLLIYF TSRLHSGVPS     60
RFSGSGSGTD YTLTISSLQP EDFATYYCQQ GNTLPYTFGQ GTKLEIK                  107
```

```
SEQ ID NO: 74            moltype = AA  length = 214
FEATURE                  Location/Qualifiers
source                   1..214
                         mol_type = protein
                         organism = synthetic construct
SEQUENCE: 74
DIQMTQSPSS LSASVGDRVT ITCRASQDIS NYLNWYQQKP GKAPKLLIYF TSRLHSGVPS   60
RFSGSGSGTD YTLTISSLQP EDFATYYCQQ GNTLPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 75            moltype = DNA  length = 354
FEATURE                  Location/Qualifiers
source                   1..354
                         mol_type = other DNA
                         organism = synthetic construct
SEQUENCE: 75
gaagtgcagc tggtggaaag cggcggcggc ctggtgcagc cgggcggcag cctgcgcctg   60
agctgcgcgg cgagcggctt tacctttagc gattatggca ttcattgggt gcgccaggcg  120
ccgggcaaag cctggaatgg gtgagctat attcgcagcg atagcagcat tattcattat  180
gcggatacct gaaaggccg ctttaccatt agccgcgata cgcgaaaaaa cagcctgtat  240
ctgcagatga cagcctgcg cgcggaagat accgcggtgt attattgcgc gcgcggccgc  300
gatcgcggct attttgatta ttggggccag ggcaccctgt gaccgtgag cagc         354

SEQ ID NO: 76            moltype = AA  length = 118
FEATURE                  Location/Qualifiers
source                   1..118
                         mol_type = protein
                         organism = synthetic construct
SEQUENCE: 76
EVQLVESGGG LVQPGGSLRL SCAASGFTFS DYGIHWVRQA PGKGLEWVSY IRSDSSIIHY   60
ADTVKGRFTI SRDNAKNSLY LQMNSLRAED TAVYYCARGR DRGYFDYWGQ GTLVTVSS   118

SEQ ID NO: 77            moltype = AA  length = 444
FEATURE                  Location/Qualifiers
source                   1..444
                         mol_type = protein
                         organism = synthetic construct
SEQUENCE: 77
EVQLVESGGG LVQPGGSLRL SCAASGFTFS DYGIHWVRQA PGKGLEWVSY IRSDSSIIHY   60
ADTVKGRFTI SRDNAKNSLY LQMNSLRAED TAVYYCARGR DRGYFDYWGQ GTLVTVSSAS  120
TKGPSVFPLA PCSRSTSEST AALGCLVKDY FPEPVTVSWN SGALTSGVHT FPAVLQSSGL  180
YSLSSVVTVP SSSLGTKTYT CNVDHKPSNT KVDKRVESKY GPPCPPCPAP EFLGGPSVFL  240
FPPKPKDTLM ISRTPEVTCV VVDVSQEDPE VQFNWYVDGV EVHNAKTKPR EEQFNSTYRV  300
VSVLTVLHQD WLNGKEYKCK VSNKGLPSSI EKTISKAKGQ PREPQVYTLP PSQEEMTKNQ  360
VSLTCLVKGF YPSDIAVEWE SNGQPENNYK TTPPVLDSDG SFFLYSRLTV DKSRWQEGNV  420
FSCSVMHEAL HNHYTQKSLS LSLG                                        444

SEQ ID NO: 78            moltype = DNA  length = 318
FEATURE                  Location/Qualifiers
source                   1..318
                         mol_type = other DNA
                         organism = synthetic construct
SEQUENCE: 78
gaaattgtgc tgacccagag cccggcgacc ctgagcctga gcccgggcga acgcgcgacc   60
ctgagctgca gcgcgagcag cagcgtgagc tatatgtatt ggtatcagca gaaaccgggc  120
caggcgccgc gcccgtggat ttatctgacc agcaacctgg cgagcggcgt gccggcgcgc  180
tttagcggca gcggcagcgg caccgatttt accctgacca ttagcagcct ggaaccggaa  240
gattttgcgg tgtattattg ccagcagtgg accagcattc cgtttacctt tggccagggc  300
accaaagtgg aaattaaa                                               318

SEQ ID NO: 79            moltype = AA  length = 106
FEATURE                  Location/Qualifiers
source                   1..106
                         mol_type = protein
                         organism = synthetic construct
SEQUENCE: 79
EIVLTQSPAT LSLSPGERAT LSCSASSSVS YMYWYQQKPG QAPRPWIYLT SNLASGVPAR   60
FSGSGSGTDF TLTISSLEPE DFAVYYCQQW TSIPFTFGQG TKVEIK                106

SEQ ID NO: 80            moltype = AA  length = 213
FEATURE                  Location/Qualifiers
source                   1..213
                         mol_type = protein
                         organism = synthetic construct
SEQUENCE: 80
EIVLTQSPAT LSLSPGERAT LSCSASSSVS YMYWYQQKPG QAPRPWIYLT SNLASGVPAR   60
FSGSGSGTDF TLTISSLEPE DFAVYYCQQW TSIPFTFGQG TKVEIKRTVA APSVFIFPPS  120
DEQLKSGTAS VVCLLNNFYP REAKVQWKVD NALQSGNSQE SVTEQDSKDS TYSLSSTLTL  180
```

```
SKADYEKHKV YACEVTHQGL SSPVTKSFNR GEC                          213

SEQ ID NO: 81            moltype = DNA  length = 366
FEATURE                  Location/Qualifiers
source                   1..366
                         mol_type = other DNA
                         organism = synthetic construct
SEQUENCE: 81
gaagtgcagc tggtggaaag cggcggcggc ctggtgcagc cgggcggcag cctgcgcctg    60
agctgcgcgg cgagcggctt tacctttagc gattatgcat gcattgggt gcgccaggcg   120
ccgggcaaag gcctggaatg ggtgagctat attagcagcg gcagcagcac catttattat   180
gcggatgccg tgaaaggccg ctttaccatt agccgcgata cgcgaaaaa cagcctgtat   240
ctgcagatga acagcctgcg cgcggaagat accgcggtgt attattgcgc gcgcattagc   300
accgtggtgg cgaaacgcta tgcgatggat tattgggggcc agggcacccct ggtgaccgtg   360
agcagc                                                            366

SEQ ID NO: 82            moltype = AA  length = 122
FEATURE                  Location/Qualifiers
source                   1..122
                         mol_type = protein
                         organism = synthetic construct
SEQUENCE: 82
EVQLVESGGG LVQPGGSLRL SCAASGFTFS DYAMHWVRQA PGKGLEWVSY ISSGSSTIYY    60
ADTVKGRFTI SRDNAKNSLY LQMNSLRAED TAVYYCARIS TVVAKRYAMD YWGQGTLVTV   120
SS                                                                122

SEQ ID NO: 83            moltype = AA  length = 448
FEATURE                  Location/Qualifiers
source                   1..448
                         mol_type = protein
                         organism = synthetic construct
SEQUENCE: 83
EVQLVESGGG LVQPGGSLRL SCAASGFTFS DYAMHWVRQA PGKGLEWVSY ISSGSSTIYY    60
ADTVKGRFTI SRDNAKNSLY LQMNSLRAED TAVYYCARIS TVVAKRYAMD YWGQGTLVTV   120
SSASTKGPSV FPLAPCSRST SESTAALGCL VKDYFPEPVT VSWNSGALTS GVHTFPAVLQ   180
SSGLYSLSSV VTVPSSSLGT KTYTCNVDHK PSNTKVDKRV ESKYGPPCPP CPAPEFLGGP   240
SVFLFPPKPK DTLMISRTPE VTCVVVDVSQ EDPEVQFNWY VDGVEVHNAK TKPREEQFNS   300
TYRVVSVLTV LHQDWLNGKE YKCKVSNKGL PSSIEKTISK AKGQPREPQV YTLPPSQEEM   360
TKNQVSLTCL VKGFYPSDIA VEWESNGQPE NNYKTTPPVL DSDGSFFLYS RLTVDKSRWQ   420
EGNVFSCSVM HEALHNHYTQ KSLSLSLG                                     448

SEQ ID NO: 84            moltype = DNA  length = 321
FEATURE                  Location/Qualifiers
source                   1..321
                         mol_type = other DNA
                         organism = synthetic construct
SEQUENCE: 84
gatattcaga tgacccagag cccgagcagc ctgagcgcga gcgtgggcga tcgcgtgacc    60
attacctgcc gcgcgagcca ggatattagc aactatctga actggtatca gcagaaaccg   120
ggcaaagcgc cgaaactgct gatttattat accagccgcc tgcatagcgg cgtgccgagc   180
cgctttagcg gcagcggcag cggcaccgat tttaccctga ccattagcag cctgcagccg   240
gaagatattg cgacctatta ttgccaggaa gtgaacatgc tgccgtttac ctttggccag   300
ggcaccaaag tggaaattaa a                                            321

SEQ ID NO: 85            moltype = AA  length = 107
FEATURE                  Location/Qualifiers
source                   1..107
                         mol_type = protein
                         organism = synthetic construct
SEQUENCE: 85
DIQMTQSPSS LSASVGDRVT ITCRASQDIS NYLNWYQQKP GKAPKLLIYY TSRLHSGVPS    60
RFSGSGSGTD FTLTISSLQP EDIATYYCQE VNMLPFTFGQ GTKVEIK                107

SEQ ID NO: 86            moltype = AA  length = 214
FEATURE                  Location/Qualifiers
source                   1..214
                         mol_type = protein
                         organism = synthetic construct
SEQUENCE: 86
DIQMTQSPSS LSASVGDRVT ITCRASQDIS NYLNWYQQKP GKAPKLLIYY TSRLHSGVPS    60
RFSGSGSGTD FTLTISSLQP EDIATYYCQE VNMLPFTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 87            moltype = DNA  length = 366
FEATURE                  Location/Qualifiers
source                   1..366
                         mol_type = other DNA
                         organism = synthetic construct
```

```
SEQUENCE: 87
gaagtgcagc tggtggaaag cggcggcggc ctggtgcagc cgggcggcag cctgcgcctg    60
agctgcgcgg cgagcggctt tacctttagc gattatggca tgcattgggt gcgccaggcg   120
ccgggcaaag gcctggaatg ggtgagctat attagcagcg gcagcaccac catttattat   180
gcggataccg tgaaaggccg ctttaccatt agccgcgata acgcgaaaaa cagcctgtat   240
ctgcagatga acagcctgcg cgcggaagat accgcggtgt attattgcgc gcgcattagc   300
accgtggtgg cgaaacgcta tgcgatggat tattgggccc agggcaccct ggtgaccgtg   360
agcagc                                                              366

SEQ ID NO: 88           moltype = AA  length = 122
FEATURE                 Location/Qualifiers
source                  1..122
                        mol_type = protein
                        organism = synthetic construct
SEQUENCE: 88
EVQLVESGGG LVQPGGSLRL SCAASGFTFS DYGMHWVRQA PGKGLEWVSY ISSGSTTIYY    60
ADTVKGRFTI SRDNAKNSLY LQMNSLRAED TAVYYCARIS TVVAKRYAMD YWGQGTLVTV   120
SS                                                                  122

SEQ ID NO: 89           moltype = AA  length = 448
FEATURE                 Location/Qualifiers
source                  1..448
                        mol_type = protein
                        organism = synthetic construct
SEQUENCE: 89
EVQLVESGGG LVQPGGSLRL SCAASGFTFS DYGMHWVRQA PGKGLEWVSY ISSGSTTIYY    60
ADTVKGRFTI SRDNAKNSLY LQMNSLRAED TAVYYCARIS TVVAKRYAMD YWGQGTLVTV   120
SSASTKGPSV FPLAPCSRST SESTAALGCL VKDYFPEPVT VSWNSGALTS GVHTFPAVLQ   180
SSGLYSLSSV VTVPSSSLGT KTYTCNVDHK PSNTKVDKRV ESKYGPPCPP CPAPEFLGGP   240
SVFLFPPKPK DTLMISRTPE VTCVVVDVSQ EDPEVQFNWY VDGVEVHNAK TKPREEQFNS   300
TYRVVSVLTV LHQDWLNGKE YKCKVSNKGL PSSIEKTISK AKGQPREPQV YTLPPSQEEM   360
TKNQVSLTCL VKGFYPSDIA VEWESNGQPE NNYKTTPPVL DSDGSFFLYS RLTVDKSRWQ   420
EGNVFSCSVL HEALHSHYTQ KSLSLSLG                                      448

SEQ ID NO: 90           moltype = DNA  length = 321
FEATURE                 Location/Qualifiers
source                  1..321
                        mol_type = other DNA
                        organism = synthetic construct
SEQUENCE: 90
gatattcaga tgacccagag cccgagcagc ctgagcgcga gcgtgggcga tcgcgtgacc    60
attacctgcc gcgcgagcca ggatattagc aactatctga actggtatca gcagaaaccg   120
ggcaaagcgc cgaaactgct gatttattat accagcgcc tgcatagcgg cgtgccgagc    180
cgctttagcg gcagcggcag cggcaccgat tttaccctgc ccattagcag cctgcagccg   240
gaagatattg cgacctatta ttgccagcag attaacgcgc tgccgtttac ctttggccag   300
ggcaccaaac tggaaattaa a                                             321

SEQ ID NO: 91           moltype = AA  length = 107
FEATURE                 Location/Qualifiers
source                  1..107
                        mol_type = protein
                        organism = synthetic construct
SEQUENCE: 91
DIQMTQSPSS LSASVGDRVT ITCRASQDIS NYLNWYQQKP GKAPKLLIYY TSRLHSGVPS    60
RFSGSGSGTD FTLTISSLQP EDIATYYCQQ INALPFTFGQ GTKLEIK                 107

SEQ ID NO: 92           moltype = AA  length = 214
FEATURE                 Location/Qualifiers
source                  1..214
                        mol_type = protein
                        organism = synthetic construct
SEQUENCE: 92
DIQMTQSPSS LSASVGDRVT ITCRASQDIS NYLNWYQQKP GKAPKLLIYY TSRLHSGVPS    60
RFSGSGSGTD FTLTISSLQP EDIATYYCQQ INALPFTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 93           moltype = DNA  length = 360
FEATURE                 Location/Qualifiers
source                  1..360
                        mol_type = other DNA
                        organism = synthetic construct
SEQUENCE: 93
caggtgcagc tggtgcagag cggcgcggaa gtgaaaaaac cgggcgcgag cgtgaaagtg    60
agctgcaaag cgagcggcta tacctttacc gattataaca tggattgggt gcgccaggcg   120
ccgggcagag aactggaatg gattggcaac attaacccga caacggcgg cacctttat    180
aaccagaaat ttaaaggccg cgcgaccctg accgtggata aaagcgcgag caccgcgtat   240
atggaactga gcagcctgcg cagcgaagat accgcggtgt attattgcgc gcggcggc    300
ctgcgccgcc gcggctttat ggattattgg ggccagggca ccctggtgac cgtgagcagc   360
```

```
SEQ ID NO: 94            moltype = AA   length = 120
FEATURE                  Location/Qualifiers
source                   1..120
                         mol_type = protein
                         organism = synthetic construct
SEQUENCE: 94
QVQLVQSGAE VKKPGASVKV SCKASGYTFT DYNMDWVRQA PGQNLEWIGN INPNNGGTFY    60
NQKFKGRATL TVDKSASTAY MELSSLRSED TAVYYCARGG LRRRGFMDYW GQGTLVTVSS   120

SEQ ID NO: 95            moltype = AA   length = 446
FEATURE                  Location/Qualifiers
source                   1..446
                         mol_type = protein
                         organism = synthetic construct
SEQUENCE: 95
QVQLVQSGAE VKKPGASVKV SCKASGYTFT DYNMDWVRQA PGQNLEWIGN INPNNGGTFY    60
NQKFKGRATL TVDKSASTAY MELSSLRSED TAVYYCARGG LRRRGFMDYW GQGTLVTVSS   120
ASTKGPSVFP LAPCSRSTSE STAALGCLVK DYFPEPVTVS WNSGALTSGV HTFPAVLQSS   180
GLYSLSSVVT VPSSSLGTKT YTCNVDHKPS NTKVDKRVES KYGPPCPPCP APEFLGGPSV   240
FLFPPKPKDT LMISRTPEVT CVVVDVSQED PEVQFNWYVD GVEVHNAKTK PREEQFNSTY   300
RVVSVLTVLH QDWLNGKEYK CKVSNKGLPS SIEKTISKAK GQPREPQVYT LPPSQEEMTK   360
NQVSLTCLVK GFYPSDIAVE WESNGQPENN YKTTPPVLDS DGSFFLYSRL TVDKSRWQEG   420
NVFSCSVMHE ALHNHYTQKS LSLSLG                                       446

SEQ ID NO: 96            moltype = DNA   length = 318
FEATURE                  Location/Qualifiers
source                   1..318
                         mol_type = other DNA
                         organism = synthetic construct
SEQUENCE: 96
gaaattgtgc tgacccagag cccggcgacc ctgagcctga gcccgggcga acgcgcgacc    60
ctgagctgcc gcgcgagcag cagcgtgatt tatattcatt ggtatcagca gaaaccgggc   120
cagagcccgc gcccgtggat ttatgcggcg agcaacctgg cgagcggcgt gccggcgcgc   180
tttagcggca gcggcagcgg caccgattat accctgacca ttagccgcct ggaaccggaa   240
gattttgcgg tgtattattg ccagcagtgg agcgtgaacc cgccgacctt tggccaggc   300
accaaactgg aaattaaa                                                318

SEQ ID NO: 97            moltype = AA   length = 106
FEATURE                  Location/Qualifiers
source                   1..106
                         mol_type = protein
                         organism = synthetic construct
SEQUENCE: 97
EIVLTQSPAT LSLSPGERAT LSCRASSSVI YIHWYQQKPG QSPRPWIYAA SNLASGVPAR    60
FSGSGSGTDY TLTISRLEPE DFAVYYCQQW SVNPPTFGQG TKLEIK                  106

SEQ ID NO: 98            moltype = AA   length = 213
FEATURE                  Location/Qualifiers
source                   1..213
                         mol_type = protein
                         organism = synthetic construct
SEQUENCE: 98
EIVLTQSPAT LSLSPGERAT LSCRASSSVI YIHWYQQKPG QSPRPWIYAA SNLASGVPAR    60
FSGSGSGTDY TLTISRLEPE DFAVYYCQQW SVNPPTFGQG TKLEIKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GEC                                213

SEQ ID NO: 99            moltype = DNA   length = 360
FEATURE                  Location/Qualifiers
source                   1..360
                         mol_type = other DNA
                         organism = synthetic construct
SEQUENCE: 99
caggtgcagc tggtgcagag cggcgcggaa gtgaaaaaac cgggcgcgag cgtgaaagtg    60
agctgcaaag cgagcggcta cctttaccg gattataacg tggattgggt gcgccaggcg   120
ccgggccagg gcctggaatg gattggcacc attaacccga caacggcgg cattctgagc   180
aaccagaaat ttaaaggccg cgtgaccatt accgtggata ccagcgcgag caccgcgtat   240
atggaactga gcagcctgcg cagcgaagat accgcggtgt attattgcgg ccgcggcggc   300
ctgcgccgcc gcggctttat ggattattgg ggccagggca ccctgtgac cgtgagcagc   360

SEQ ID NO: 100           moltype = AA   length = 120
FEATURE                  Location/Qualifiers
source                   1..120
                         mol_type = protein
                         organism = synthetic construct
SEQUENCE: 100
QVQLVQSGAE VKKPGASVKV SCKASGYTFT DYNVDWVRQA PGQGLEWIGT INPNNGGILS    60
NQKFKGRVTI TVDTSASTAY MELSSLRSED TAVYYCGRGG LRRRGFMDYW GQGTLVTVSS   120
```

```
SEQ ID NO: 101           moltype = AA  length = 446
FEATURE                  Location/Qualifiers
source                   1..446
                         mol_type = protein
                         organism = synthetic construct
SEQUENCE: 101
QVQLVQSGAE VKKPGASVKV SCKASGYTFT DYNVDWVRQA PGQGLEWIGT INPNNGGILS   60
NQKFKGRVTI TVDTSASTAY MELSSLRSED TAVYYCGRGG LRRRGFMDYW GQGTLVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLG                                      446

SEQ ID NO: 102           moltype = DNA  length = 318
FEATURE                  Location/Qualifiers
source                   1..318
                         mol_type = other DNA
                         organism = synthetic construct
SEQUENCE: 102
gaaattgtgc tgacccagag cccggcgacc ctgagcctga gcccgggcga acgcgcgacc   60
ctgagctgcc gcgcgagcag cagcgtgatt tatattcatt ggtatcagca gaaaccgggc  120
caggcgccgc gcccgtggat ttatgcggcg agcaacctgc cgagcggcgt gccggcgcgc  180
tttagcggca gcggcagcgg caccgatttt accctgacca ttagcagcct ggaaccggaa  240
gattttgcgg tgtattattg ccagcagtgg agcagcaacc cgccgacctt tggccagggc  300
accaaagtgg aaattaaa                                                318

SEQ ID NO: 103           moltype = AA  length = 106
FEATURE                  Location/Qualifiers
source                   1..106
                         mol_type = protein
                         organism = synthetic construct
SEQUENCE: 103
EIVLTQSPAT LSLSPGERAT LSCRASSSVI YIHWYQQKPG QAPRPWIYAA SNLPSGVPAR   60
FSGSGSGTDF TLTISSLEPE DFAVYYCQQW SSNPPTFGQG TKVEIK                 106

SEQ ID NO: 104           moltype = AA  length = 213
FEATURE                  Location/Qualifiers
source                   1..213
                         mol_type = protein
                         organism = synthetic construct
SEQUENCE: 104
EIVLTQSPAT LSLSPGERAT LSCRASSSVI YIHWYQQKPG QAPRPWIYAA SNLPSGVPAR   60
FSGSGSGTDF TLTISSLEPE DFAVYYCQQW SSNPPTFGQG TKVEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 105           moltype = AA  length = 5
FEATURE                  Location/Qualifiers
source                   1..5
                         mol_type = protein
                         organism = Mus musculus
SEQUENCE: 105
DYGMH                                                                5

SEQ ID NO: 106           moltype = AA  length = 17
FEATURE                  Location/Qualifiers
source                   1..17
                         mol_type = protein
                         organism = Mus musculus
SEQUENCE: 106
YINSGSSKIY HADTVKG                                                  17

SEQ ID NO: 107           moltype = AA  length = 15
FEATURE                  Location/Qualifiers
source                   1..15
                         mol_type = protein
                         organism = Mus musculus
SEQUENCE: 107
ARFPTVVAAR YPMDY                                                    15

SEQ ID NO: 108           moltype = AA  length = 11
FEATURE                  Location/Qualifiers
source                   1..11
                         mol_type = protein
                         organism = Mus musculus
SEQUENCE: 108
```

RASQDISNYL N                                                                                  11

SEQ ID NO: 109          moltype = AA  length = 7
FEATURE                 Location/Qualifiers
source                  1..7
                        mol_type = protein
                        organism = Mus musculus SEQUENCE: 109
FTSRLHS                                                                                        7

SEQ ID NO: 110          moltype = AA  length = 9
FEATURE                 Location/Qualifiers
source                  1..9
                        mol_type = protein
                        organism = Mus musculus SEQUENCE: 110
QQGNTLPYT                                                                                      9

SEQ ID NO: 111          moltype = AA  length = 5
FEATURE                 Location/Qualifiers
source                  1..5
                        mol_type = protein
                        organism = Mus musculus SEQUENCE: 111
DYGIH                                                                                          5

SEQ ID NO: 112          moltype = AA  length = 17
FEATURE                 Location/Qualifiers
source                  1..17
                        mol_type = protein
                        organism = Mus musculus SEQUENCE: 112
YIRSDSSIIH YADTVKG                                                                            17

SEQ ID NO: 113          moltype = AA  length = 11
FEATURE                 Location/Qualifiers
source                  1..11
                        mol_type = protein
                        organism = Mus musculus SEQUENCE: 113
TRGRDRGYFD Y                                                                                  11

SEQ ID NO: 114          moltype = AA  length = 10
FEATURE                 Location/Qualifiers
source                  1..10
                        mol_type = protein
                        organism = Mus musculus SEQUENCE: 114
SASSSVSYMY                                                                                    10

SEQ ID NO: 115          moltype = AA  length = 7
FEATURE                 Location/Qualifiers
source                  1..7
                        mol_type = protein
                        organism = Mus musculus SEQUENCE: 115
LTSNLAS                                                                                        7

SEQ ID NO: 116          moltype = AA  length = 9
FEATURE                 Location/Qualifiers
source                  1..9
                        mol_type = protein
                        organism = Mus musculus SEQUENCE: 116
QQWTSIPFT                                                                                      9

SEQ ID NO: 117          moltype = AA  length = 5
FEATURE                 Location/Qualifiers
source                  1..5
                        mol_type = protein
                        organism = Mus musculus SEQUENCE: 117
DYGMH                                                                                          5

SEQ ID NO: 118          moltype = AA  length = 17
FEATURE                 Location/Qualifiers
source                  1..17
                        mol_type = protein
                        organism = Mus musculus

| | | |
|---|---|---|
| SEQUENCE: 118 YISSGSTTIY YADTVKG | | 17 |
| SEQ ID NO: 119 FEATURE source | moltype = AA length = 15 Location/Qualifiers 1..15 mol_type = protein organism = Mus musculus | |
| SEQUENCE: 119 ARISTVVAKR YAMDY | | 15 |
| SEQ ID NO: 120 FEATURE source | moltype = AA length = 11 Location/Qualifiers 1..11 mol_type = protein organism = Mus musculus | |
| SEQUENCE: 120 RASQDISNYL N | | 11 |
| SEQ ID NO: 121 FEATURE source | moltype = AA length = 7 Location/Qualifiers 1..7 mol_type = protein organism = Mus musculus | |
| SEQUENCE: 121 YTSRLHS | | 7 |
| SEQ ID NO: 122 FEATURE source | moltype = AA length = 9 Location/Qualifiers 1..9 mol_type = protein organism = Mus musculus | |
| SEQUENCE: 122 QQINALPLT | | 9 |
| SEQ ID NO: 123 FEATURE source | moltype = AA length = 5 Location/Qualifiers 1..5 mol_type = protein organism = Mus musculus | |
| SEQUENCE: 123 DYGMH | | 5 |
| SEQ ID NO: 124 FEATURE source | moltype = AA length = 17 Location/Qualifiers 1..17 mol_type = protein organism = Mus musculus | |
| SEQUENCE: 124 YISSGSSTIY YADTVKG | | 17 |
| SEQ ID NO: 125 FEATURE source | moltype = AA length = 15 Location/Qualifiers 1..15 mol_type = protein organism = Mus musculus | |
| SEQUENCE: 125 ARISTVVAKR YAMDY | | 15 |
| SEQ ID NO: 126 FEATURE source | moltype = AA length = 11 Location/Qualifiers 1..11 mol_type = protein organism = Mus musculus | |
| SEQUENCE: 126 RASQDISNYL N | | 11 |
| SEQ ID NO: 127 FEATURE source | moltype = AA length = 7 Location/Qualifiers 1..7 mol_type = protein organism = Mus musculus | |
| SEQUENCE: 127 YTSRLHS | | 7 |
| SEQ ID NO: 128 FEATURE source | moltype = AA length = 9 Location/Qualifiers 1..9 mol_type = protein | |

```
organism = Mus musculus
SEQUENCE: 128
QEVNMLPLT                                                              9

SEQ ID NO: 129          moltype = AA   length = 5
FEATURE                 Location/Qualifiers
source                  1..5
                        mol_type = protein
                        organism = Mus musculus
SEQUENCE: 129
DYGMH                                                                  5

SEQ ID NO: 130          moltype = AA   length = 17
FEATURE                 Location/Qualifiers
source                  1..17
                        mol_type = protein
                        organism = Mus musculus
SEQUENCE: 130
YISSGSTTIY YADTVKG                                                    17

SEQ ID NO: 131          moltype = AA   length = 13
FEATURE                 Location/Qualifiers
source                  1..13
                        mol_type = protein
                        organism = Mus musculus
SEQUENCE: 131
ISTVVAKRYA MDY                                                        13

SEQ ID NO: 132          moltype = AA   length = 11
FEATURE                 Location/Qualifiers
source                  1..11
                        mol_type = protein
                        organism = Mus musculus
SEQUENCE: 132
RASQDISNYL N                                                          11

SEQ ID NO: 133          moltype = AA   length = 7
FEATURE                 Location/Qualifiers
source                  1..7
                        mol_type = protein
                        organism = Mus musculus
SEQUENCE: 133
YTSRLHS                                                                7

SEQ ID NO: 134          moltype = AA   length = 9
FEATURE                 Location/Qualifiers
source                  1..9
                        mol_type = protein
                        organism = Mus musculus
SEQUENCE: 134
QQINALPLT                                                              9

SEQ ID NO: 135          moltype = AA   length = 5
FEATURE                 Location/Qualifiers
source                  1..5
                        mol_type = protein
                        organism = Mus musculus
SEQUENCE: 135
DYNMD                                                                  5

SEQ ID NO: 136          moltype = AA   length = 17
FEATURE                 Location/Qualifiers
source                  1..17
                        mol_type = protein
                        organism = Mus musculus
SEQUENCE: 136
DINPNNGNIL FNQKFKG                                                    17

SEQ ID NO: 137          moltype = AA   length = 13
FEATURE                 Location/Qualifiers
source                  1..13
                        mol_type = protein
                        organism = Mus musculus
SEQUENCE: 137
GRGGLRRRGF MDY                                                        13

SEQ ID NO: 138          moltype = AA   length = 10
FEATURE                 Location/Qualifiers
source                  1..10
```

```
                            mol_type = protein
                            organism = Mus musculus
SEQUENCE: 138
RASSSVSYMH                                                              10

SEQ ID NO: 139              moltype = AA   length = 7
FEATURE                     Location/Qualifiers
source                      1..7
                            mol_type = protein
                            organism = Mus musculus
SEQUENCE: 139
AASNLAS                                                                  7

SEQ ID NO: 140              moltype = AA   length = 9
FEATURE                     Location/Qualifiers
source                      1..9
                            mol_type = protein
                            organism = Mus musculus
SEQUENCE: 140
QQWSSNPPT                                                                9

SEQ ID NO: 141              moltype = AA   length = 5
FEATURE                     Location/Qualifiers
source                      1..5
                            mol_type = protein
                            organism = Mus musculus
SEQUENCE: 141
DYNMD                                                                    5

SEQ ID NO: 142              moltype = AA   length = 17
FEATURE                     Location/Qualifiers
source                      1..17
                            mol_type = protein
                            organism = Mus musculus
SEQUENCE: 142
NINPNNGGTF YNQKFKG                                                      17

SEQ ID NO: 143              moltype = AA   length = 13
FEATURE                     Location/Qualifiers
source                      1..13
                            mol_type = protein
                            organism = Mus musculus
SEQUENCE: 143
GRGGLRRRGF MDY                                                          13

SEQ ID NO: 144              moltype = AA   length = 10
FEATURE                     Location/Qualifiers
source                      1..10
                            mol_type = protein
                            organism = Mus musculus
SEQUENCE: 144
RASSSVIYIH                                                              10

SEQ ID NO: 145              moltype = AA   length = 7
FEATURE                     Location/Qualifiers
source                      1..7
                            mol_type = protein
                            organism = Mus musculus
SEQUENCE: 145
AASNLAS                                                                  7

SEQ ID NO: 146              moltype = AA   length = 9
FEATURE                     Location/Qualifiers
source                      1..9
                            mol_type = protein
                            organism = Mus musculus
SEQUENCE: 146
QQWSVNPPT                                                                9

SEQ ID NO: 147              moltype = AA   length = 5
FEATURE                     Location/Qualifiers
source                      1..5
                            mol_type = protein
                            organism = Mus musculus
SEQUENCE: 147
DYNMD                                                                    5

SEQ ID NO: 148              moltype = AA   length = 17
FEATURE                     Location/Qualifiers
```

```
source                    1..17
                          mol_type = protein
                          organism = Mus musculus
SEQUENCE: 148
DINPNNGNIL FNQKFKG                                                    17

SEQ ID NO: 149            moltype = AA  length = 13
FEATURE                   Location/Qualifiers
source                    1..13
                          mol_type = protein
                          organism = Mus musculus
SEQUENCE: 149
GRGGLRRRGF MDY                                                        13

SEQ ID NO: 150            moltype = AA  length = 10
FEATURE                   Location/Qualifiers
source                    1..10
                          mol_type = protein
                          organism = Mus musculus
SEQUENCE: 150
RASSSVSYMH                                                            10

SEQ ID NO: 151            moltype = AA  length = 7
FEATURE                   Location/Qualifiers
source                    1..7
                          mol_type = protein
                          organism = Mus musculus
SEQUENCE: 151
AASNLAS                                                                7

SEQ ID NO: 152            moltype = AA  length = 9
FEATURE                   Location/Qualifiers
source                    1..9
                          mol_type = protein
                          organism = Mus musculus
SEQUENCE: 152
QQWSSNPPT                                                              9

SEQ ID NO: 153            moltype = AA  length = 5
FEATURE                   Location/Qualifiers
source                    1..5
                          mol_type = protein
                          organism = Mus musculus
SEQUENCE: 153
DYNMD                                                                  5

SEQ ID NO: 154            moltype = AA  length = 17
FEATURE                   Location/Qualifiers
source                    1..17
                          mol_type = protein
                          organism = Mus musculus
SEQUENCE: 154
TTNPNNGGTL YNQKFKG                                                    17

SEQ ID NO: 155            moltype = AA  length = 13
FEATURE                   Location/Qualifiers
source                    1..13
                          mol_type = protein
                          organism = Mus musculus
SEQUENCE: 155
ARGGLRRRGF VDY                                                        13

SEQ ID NO: 156            moltype = AA  length = 10
FEATURE                   Location/Qualifiers
source                    1..10
                          mol_type = protein
                          organism = Mus musculus
SEQUENCE: 156
RASSSVNYLH                                                            10

SEQ ID NO: 157            moltype = AA  length = 7
FEATURE                   Location/Qualifiers
source                    1..7
                          mol_type = protein
                          organism = Mus musculus
SEQUENCE: 157
ATSNLAS                                                                7

SEQ ID NO: 158            moltype = AA  length = 9
```

```
FEATURE                 Location/Qualifiers
source                  1..9
                        mol_type = protein
                        organism = Mus musculus
SEQUENCE: 158
QQWSSNPPT                                                               9

SEQ ID NO: 159          moltype = AA  length = 5
FEATURE                 Location/Qualifiers
source                  1..5
                        mol_type = protein
                        organism = Mus musculus
SEQUENCE: 159
DYNMD                                                                   5

SEQ ID NO: 160          moltype = AA  length = 17
FEATURE                 Location/Qualifiers
source                  1..17
                        mol_type = protein
                        organism = Mus musculus
SEQUENCE: 160
DINPNNGNIL FNQKFKG                                                     17

SEQ ID NO: 161          moltype = AA  length = 13
FEATURE                 Location/Qualifiers
source                  1..13
                        mol_type = protein
                        organism = Mus musculus
SEQUENCE: 161
GRGGLRRRGF MDY                                                         13

SEQ ID NO: 162          moltype = AA  length = 10
FEATURE                 Location/Qualifiers
source                  1..10
                        mol_type = protein
                        organism = Mus musculus
SEQUENCE: 162
RASSSVSYMH                                                             10

SEQ ID NO: 163          moltype = AA  length = 7
FEATURE                 Location/Qualifiers
source                  1..7
                        mol_type = protein
                        organism = Mus musculus
SEQUENCE: 163
AASNLAS                                                                 7

SEQ ID NO: 164          moltype = AA  length = 9
FEATURE                 Location/Qualifiers
source                  1..9
                        mol_type = protein
                        organism = Mus musculus
SEQUENCE: 164
QQWSSNPPT                                                               9

SEQ ID NO: 165          moltype = AA  length = 5
FEATURE                 Location/Qualifiers
source                  1..5
                        mol_type = protein
                        organism = Mus musculus
SEQUENCE: 165
DYNMD                                                                   5

SEQ ID NO: 166          moltype = AA  length = 17
FEATURE                 Location/Qualifiers
source                  1..17
                        mol_type = protein
                        organism = Mus musculus
SEQUENCE: 166
NINPNNGGTF YNQKFKG                                                     17

SEQ ID NO: 167          moltype = AA  length = 13
FEATURE                 Location/Qualifiers
source                  1..13
                        mol_type = protein
                        organism = Mus musculus
SEQUENCE: 167
GRGGLRRRGF MDY                                                         13
```

-continued

```
SEQ ID NO: 168         moltype = AA  length = 10
FEATURE                Location/Qualifiers
source                 1..10
                       mol_type = protein
                       organism = Mus musculus
SEQUENCE: 168
RASSSVIYIH                                                                10

SEQ ID NO: 169         moltype = AA  length = 7
FEATURE                Location/Qualifiers
source                 1..7
                       mol_type = protein
                       organism = Mus musculus
SEQUENCE: 169
AASNLAS                                                                    7

SEQ ID NO: 170         moltype = AA  length = 9
FEATURE                Location/Qualifiers
source                 1..9
                       mol_type = protein
                       organism = Mus musculus
SEQUENCE: 170
QQWSVNPPT                                                                  9

SEQ ID NO: 171         moltype = AA  length = 5
FEATURE                Location/Qualifiers
source                 1..5
                       mol_type = protein
                       organism = Mus musculus
SEQUENCE: 171
DYNMD                                                                      5

SEQ ID NO: 172         moltype = AA  length = 17
FEATURE                Location/Qualifiers
source                 1..17
                       mol_type = protein
                       organism = Mus musculus
SEQUENCE: 172
TINPNNGDTM YNQKFKD                                                        17

SEQ ID NO: 173         moltype = AA  length = 13
FEATURE                Location/Qualifiers
source                 1..13
                       mol_type = protein
                       organism = Mus musculus
SEQUENCE: 173
GRGGLRRRGF MDY                                                            13

SEQ ID NO: 174         moltype = AA  length = 10
FEATURE                Location/Qualifiers
source                 1..10
                       mol_type = protein
                       organism = Mus musculus
SEQUENCE: 174
RASSSVIYIH                                                                10

SEQ ID NO: 175         moltype = AA  length = 7
FEATURE                Location/Qualifiers
source                 1..7
                       mol_type = protein
                       organism = Mus musculus
SEQUENCE: 175
AISNLAS                                                                    7

SEQ ID NO: 176         moltype = AA  length = 9
FEATURE                Location/Qualifiers
source                 1..9
                       mol_type = protein
                       organism = Mus musculus
SEQUENCE: 176
QQWSVNPPT                                                                  9

SEQ ID NO: 177         moltype = AA  length = 5
FEATURE                Location/Qualifiers
source                 1..5
                       mol_type = protein
                       organism = Mus musculus
SEQUENCE: 177
DYNMD                                                                      5
```

-continued

```
SEQ ID NO: 178            moltype = AA   length = 17
FEATURE                   Location/Qualifiers
source                    1..17
                          mol_type = protein
                          organism = Mus musculus
SEQUENCE: 178
NINPNNGGTF YNQKFKG                                                    17

SEQ ID NO: 179            moltype = AA   length = 13
FEATURE                   Location/Qualifiers
source                    1..13
                          mol_type = protein
                          organism = Mus musculus
SEQUENCE: 179
GRGGLRRRGF MDY                                                        13

SEQ ID NO: 180            moltype = AA   length = 10
FEATURE                   Location/Qualifiers
source                    1..10
                          mol_type = protein
                          organism = Mus musculus
SEQUENCE: 180
RASSSVIYIH                                                            10

SEQ ID NO: 181            moltype = AA   length = 7
FEATURE                   Location/Qualifiers
source                    1..7
                          mol_type = protein
                          organism = Mus musculus
SEQUENCE: 181
AASNLAS                                                                7

SEQ ID NO: 182            moltype = AA   length = 9
FEATURE                   Location/Qualifiers
source                    1..9
                          mol_type = protein
                          organism = Mus musculus
SEQUENCE: 182
QQWSVNPPT                                                              9

SEQ ID NO: 183            moltype = AA   length = 5
FEATURE                   Location/Qualifiers
source                    1..5
                          mol_type = protein
                          organism = Mus musculus
SEQUENCE: 183
DYNMD                                                                  5

SEQ ID NO: 184            moltype = AA   length = 17
FEATURE                   Location/Qualifiers
source                    1..17
                          mol_type = protein
                          organism = Mus musculus
SEQUENCE: 184
TINPNNGGTF YNQNFKG                                                    17

SEQ ID NO: 185            moltype = AA   length = 13
FEATURE                   Location/Qualifiers
source                    1..13
                          mol_type = protein
                          organism = Mus musculus
SEQUENCE: 185
GRGGLRRRGF MDY                                                        13

SEQ ID NO: 186            moltype = AA   length = 10
FEATURE                   Location/Qualifiers
source                    1..10
                          mol_type = protein
                          organism = Mus musculus
SEQUENCE: 186
RASSSVIYIH                                                            10

SEQ ID NO: 187            moltype = AA   length = 7
FEATURE                   Location/Qualifiers
source                    1..7
                          mol_type = protein
                          organism = Mus musculus
SEQUENCE: 187
```

```
AASNLAS                                                                          7

SEQ ID NO: 188          moltype = AA  length = 9
FEATURE                 Location/Qualifiers
source                  1..9
                        mol_type = protein
                        organism = Mus musculus SEQUENCE: 188
QQWSVNPPT                                                                        9

SEQ ID NO: 189          moltype = AA  length = 5
FEATURE                 Location/Qualifiers
source                  1..5
                        mol_type = protein
                        organism = Mus musculus SEQUENCE: 189
DYNMD                                                                            5

SEQ ID NO: 190          moltype = AA  length = 17
FEATURE                 Location/Qualifiers
source                  1..17
                        mol_type = protein
                        organism = Mus musculus SEQUENCE: 190
NINPNNGGTF YNQKFKG                                                              17

SEQ ID NO: 191          moltype = AA  length = 13
FEATURE                 Location/Qualifiers
source                  1..13
                        mol_type = protein
                        organism = Mus musculus SEQUENCE: 191
GRGGLRRRGF LDY                                                                  13

SEQ ID NO: 192          moltype = AA  length = 10
FEATURE                 Location/Qualifiers
source                  1..10
                        mol_type = protein
                        organism = Mus musculus SEQUENCE: 192
RASSSVIYIH                                                                      10

SEQ ID NO: 193          moltype = AA  length = 7
FEATURE                 Location/Qualifiers
source                  1..7
                        mol_type = protein
                        organism = Mus musculus SEQUENCE: 193
AVSNLAS                                                                          7

SEQ ID NO: 194          moltype = AA  length = 9
FEATURE                 Location/Qualifiers
source                  1..9
                        mol_type = protein
                        organism = Mus musculus SEQUENCE: 194
QQWSVNPPT                                                                        9

SEQ ID NO: 195          moltype = AA  length = 5
FEATURE                 Location/Qualifiers
source                  1..5
                        mol_type = protein
                        organism = Mus musculus SEQUENCE: 195
DYNMD                                                                            5

SEQ ID NO: 196          moltype = AA  length = 17
FEATURE                 Location/Qualifiers
source                  1..17
                        mol_type = protein
                        organism = Mus musculus SEQUENCE: 196
NINPNNGGTF YNQKFKG                                                              17

SEQ ID NO: 197          moltype = AA  length = 13
FEATURE                 Location/Qualifiers
source                  1..13
                        mol_type = protein
                        organism = Mus musculus
```

-continued

```
SEQUENCE: 197
GRGGLRRRGF MDY                                                          13

SEQ ID NO: 198         moltype = AA   length = 10
FEATURE                Location/Qualifiers
source                 1..10
                       mol_type = protein
                       organism = Mus musculus
SEQUENCE: 198
RASSSVIYIH                                                              10

SEQ ID NO: 199         moltype = AA   length = 7
FEATURE                Location/Qualifiers
source                 1..7
                       mol_type = protein
                       organism = Mus musculus
SEQUENCE: 199
AASNLAS                                                                 7

SEQ ID NO: 200         moltype = AA   length = 9
FEATURE                Location/Qualifiers
source                 1..9
                       mol_type = protein
                       organism = Mus musculus
SEQUENCE: 200
QQWSVNPPT                                                               9

SEQ ID NO: 201         moltype = AA   length = 5
FEATURE                Location/Qualifiers
source                 1..5
                       mol_type = protein
                       organism = Mus musculus
SEQUENCE: 201
DYNVD                                                                   5

SEQ ID NO: 202         moltype = AA   length = 17
FEATURE                Location/Qualifiers
source                 1..17
                       mol_type = protein
                       organism = Mus musculus
SEQUENCE: 202
TINPNNGGIL SNQKFKG                                                      17

SEQ ID NO: 203         moltype = AA   length = 13
FEATURE                Location/Qualifiers
source                 1..13
                       mol_type = protein
                       organism = Mus musculus
SEQUENCE: 203
GRGGLRRRGF MDY                                                          13

SEQ ID NO: 204         moltype = AA   length = 10
FEATURE                Location/Qualifiers
source                 1..10
                       mol_type = protein
                       organism = Mus musculus
SEQUENCE: 204
RASSSVIYIH                                                              10

SEQ ID NO: 205         moltype = AA   length = 7
FEATURE                Location/Qualifiers
source                 1..7
                       mol_type = protein
                       organism = Mus musculus
SEQUENCE: 205
AASNLPS                                                                 7

SEQ ID NO: 206         moltype = AA   length = 9
FEATURE                Location/Qualifiers
source                 1..9
                       mol_type = protein
                       organism = Mus musculus
SEQUENCE: 206
QQWSSNPPT                                                               9

SEQ ID NO: 207         moltype = AA   length = 8
FEATURE                Location/Qualifiers
source                 1..8
                       mol_type = protein
```

| | organism = synthetic construct | |
|---|---|---|
| SEQUENCE: 207 | | |
| DYKDDDDK | | 8 |

What is claimed is:

1. An antibody specifically binding to interleukin-4 receptor alpha or an antigen-binding fragment thereof, comprising a heavy chain variable region and a light chain variable region, wherein the heavy chain variable region comprises an HCDR1 sequence, an HCDR2 sequence and an HCDR3 sequence, the light chain variable region comprises an LCDR1, an LCDR2 and an LCDR3 sequence, and wherein, the HCDR1 sequence, HCDR2 sequence, HCDR3 sequence, LCDR1 sequence, LCDR2 sequence and LCDR3 sequence respectively comprise the amino acid sequences of SEQ ID NOs: 129-134.

2. The antibody or the antigen-binding fragment thereof according to claim 1, wherein the heavy chain variable region comprises the amino acid sequence of SEQ ID NO: 88, and the light chain variable region comprises the amino acid sequence of SEQ ID NO: 91; or the heavy chain variable region comprises the amino acid sequence of SEQ ID NO: 18, and the light chain variable region comprises the amino acid sequence of SEQ ID NO: 20.

3. The antibody or the antigen-binding fragment thereof according to claim 1, wherein the heavy chain variable region comprises the amino acid sequence of SEQ ID NO: 88, and the light chain variable region comprises the amino acid sequence of SEQ ID NO: 91.

4. The antibody or the antigen-binding fragment thereof according to claim 3, wherein the antibody or the antigen-binding fragment thereof comprises a heavy chain sequence comprising the amino acid sequence of SEQ ID NO: 89, and a light chain sequence comprising the amino acid sequence of SEQ ID NO: 92.

5. The antibody or the antigen-binding fragment thereof according to claim 3, wherein the antigen-binding fragment is selected from a group consisting of an Fab fragment, an Fab' fragment, an F(ab')2 fragment, an Fv fragment, and an scFv fragment.

6. The antibody or the antigen-binding fragment thereof according to claim 1, wherein the antibody or the antigen-binding fragment thereof binds to interleukin-4 receptor alpha at a KD less than 600 pM.

7. The antibody or the antigen-binding fragment thereof according to claim 1, wherein the antibody or the antigen-binding fragment thereof specifically binds to human interleukin-4 receptor alpha or mouse interleukin-4 receptor alpha.

8. A pharmaceutical composition, comprising the antibody or the antigen-binding fragment thereof according to claim 1 and a pharmaceutically acceptable carrier.

9. The antibody or the antigen-binding fragment thereof according to claim 1, wherein the antibody or the antigen-binding fragment thereof binds to interleukin-4 receptor alpha at a KD less than 350 pM.

10. The antibody or the antigen-binding fragment thereof according to claim 1, wherein the antibody or the antigen-binding fragment thereof inhibits IL-4-induced TF-1 cell proliferation or inhibits IgE secretion of B cells.

* * * * *